US012226673B2

United States Patent
Velo

(10) Patent No.: US 12,226,673 B2
(45) Date of Patent: Feb. 18, 2025

(54) EXERTION-DRIVEN PHYSIOLOGICAL MONITORING AND PREDICTION METHOD AND SYSTEM

(71) Applicant: Salutron, Inc., Newark, CA (US)

(72) Inventor: Lino Velo, San Ramon, CA (US)

(73) Assignee: Salutron, Inc., Newark, CA (US)

( * ) Notice: Subject to any disclaimer, the term of this patent is extended or adjusted under 35 U.S.C. 154(b) by 695 days.

(21) Appl. No.: 17/319,298

(22) Filed: May 13, 2021

(65) Prior Publication Data

US 2022/0142511 A1 May 12, 2022

Related U.S. Application Data

(60) Provisional application No. 63/111,468, filed on Nov. 9, 2020.

(51) Int. Cl.
*A63B 24/00* (2006.01)
*A01K 15/02* (2006.01)
(Continued)

(52) U.S. Cl.
CPC ........ *A63B 24/0062* (2013.01); *A01K 15/027* (2013.01); *A61B 5/0205* (2013.01);
(Continued)

(58) Field of Classification Search
CPC ............ A63B 2230/04; A63B 2220/89; A63B 2220/805; A63B 2220/833; A63B 2220/808; A63B 2024/0065; A61B 5/222
See application file for complete search history.

(56) References Cited

U.S. PATENT DOCUMENTS 10,503,268 B2   12/2019   Yuen et al.
10,512,406 B2   12/2019   Martinez
(Continued)

FOREIGN PATENT DOCUMENTS

WO   WO2016096454 A1   6/2016

OTHER PUBLICATIONS

Restriction Requirement dated Mar. 23, 2023, U.S. Appl. No. 17/319,304, filed May 13, 2021.
(Continued)

*Primary Examiner* — Lynsey C Eiseman
*Assistant Examiner* — Amanda L Steinberg
(74) *Attorney, Agent, or Firm* — Pearl Cohen Zedek Latzer Baratz LLP

(57) ABSTRACT

Automated systems and methods are presented for determining the physiological response of human or suitable animal subjects to physical exertion. The methods and systems can include monitoring sensors that capture the motion of the subject along with corresponding physiological data, and can track such motion for the duration of a period of physical exertion. The system is able to acquire an initial stream of physiological data from the subject during a range of physical exertion activities that are representative of the events intended to be monitored with the proposed method and system, enabling a corresponding dynamic physiological response model to be created. The motion tracking system and physiological response model can then be used to predict the physiological response to physical exertion events under a prescribed framework, including applications during real-time event monitoring.

19 Claims, 32 Drawing Sheets

(51) Int. Cl.
- *A61B 5/00* (2006.01)
- *A61B 5/0205* (2006.01)
- *A61B 5/024* (2006.01)
- *A61B 5/22* (2006.01)
- *A63B 22/02* (2006.01)
- *A63B 22/06* (2006.01)

(52) U.S. Cl.
CPC .............. *A61B 5/024* (2013.01); *A61B 5/222* (2013.01); *A61B 5/6801* (2013.01); *A61B 5/7275* (2013.01); *A61B 5/7475* (2013.01); *A61B 2503/10* (2013.01); *A61B 2562/0219* (2013.01); *A63B 22/02* (2013.01); *A63B 22/0605* (2013.01); *A63B 2024/0065* (2013.01); *A63B 2220/805* (2013.01); *A63B 2220/808* (2013.01); *A63B 2220/833* (2013.01); *A63B 2220/89* (2013.01); *A63B 2230/04* (2013.01)

(56) References Cited

U.S. PATENT DOCUMENTS

| | | | |
|---|---|---|---|
| 10,617,308 B2 | 4/2020 | Presura et al. | |
| 10,617,311 B2 | 4/2020 | Li | |
| 2015/0196213 A1* | 7/2015 | Pandia | A61B 5/7278 600/509 |
| 2015/0327804 A1 | 11/2015 | Lefever et al. | |
| 2016/0058372 A1* | 3/2016 | Raghuram | A61B 5/681 600/595 |
| 2016/0361597 A1* | 12/2016 | Cole | A63B 23/03583 |
| 2017/0188894 A1* | 7/2017 | Chang | A61B 5/1121 |
| 2017/0337033 A1* | 11/2017 | Duyan | G06F 1/163 |
| 2018/0028075 A1* | 2/2018 | Presura | A61B 5/681 |
| 2018/0253740 A1* | 9/2018 | Ackland | A61B 5/02055 |
| 2018/0296157 A1 | 10/2018 | Bleich et al. | |
| 2019/0209049 A1 | 7/2019 | Granlund | |
| 2020/0151595 A1* | 5/2020 | Jayalath | A63B 21/0442 |
| 2020/0275845 A1 | 9/2020 | Kawakami | |
| 2020/0398112 A1 | 12/2020 | Lu et al. | |
| 2021/0068689 A1 | 3/2021 | Ochs et al. | |
| 2022/0079452 A1* | 3/2022 | Rao | A61B 5/0833 |

OTHER PUBLICATIONS

Response to Office Action dated Nov. 8, 2023, U.S. Appl. No. 17/319,304, filed May 13, 2021.
Brage, S., et al., "Reliability and validity of the combined heart rate and movement sensor Actiheart," European Journal of Clinical Nutrition, Feb. 2005, 10 pages.
U.S. Appl. No. 17/319,304, filed May 13, 2021.
U.S. Appl. No. 17/319,293, filed May 13, 2021.
Non-final Office Action dated Aug. 9, 2023, U.S. Appl. No. 17/319,304, filed May 13, 2021.
Response to Restriction Requirement dated May 22, 2023, U.S. Appl. No. 17/319,304, filed May 13, 2021.
Restriction Requirement dated Apr. 15, 2024, U.S. Appl. No. 17/319,293, filed May 13, 2021.
Response to Office Action dated Apr. 29, 2024, U.S. Appl. No. 17/319,304, filed May 13, 2021.
Non-final Office Action dated Aug. 12, 2024, U.S. Appl. No. 17/319,304, filed May 13, 2021.
Final Office Action dated Jan. 29, 2024, U.S. Appl. No. 17/319,304, filed May 13, 2021.
Response to Restriction Requirement dated Jun. 3, 2024, U.S. Appl. No. 17/319,293, filed May 13, 2021.
Non-final Office Action dated Jun. 20, 2024, U.S. Appl. No. 17/319,293, filed May 13, 2021.
Response to Office Action dated Sep. 19, 2024, U.S. Appl. No. 17/319,293, filed May 13, 2021.
Response to Non-final Office Action dated Nov. 9, 2024, U.S. Appl. No. 17/319,304, filed May 13, 2021.
Final Office Action dated Dec. 11, 2024, U.S. Appl. No. 17/319,293, filed May 13, 2021.

* cited by examiner

EXERTION-DRIVEN PHYSIOLOGICAL MONITORING AND PREDICTION METHOD AND SYSTEM

PRIORITY

This application claims priority to U.S. Provisional Patent Application No. 63/111,468, entitled "Exertion-driven Physiological Monitoring and Prediction Method and System" and filed Nov. 9, 2020 by Lino Velo, which is incorporated by reference in its entirety.

BACKGROUND

The present technology relates to determining the physiological response to physical exertion.

Physical activity and exercise are critical for the health, fitness and quality of life of humans, enabling more efficient functioning of the organs of the body, including the brain, heart, lungs, and muscles among others. It may also help prevent or delay the onset of many health problems and diseases, including type 2 diabetes, cancer, and cardiovascular disease. It is thus important to be able to quantify the impact of various types and levels of physical activities on the physiological response of the human body in the short-term, as well as the mid-term and long-term. The physiological response of the cardiovascular system to physical activity is among the most researched fields in the health and fitness industries.

DETAILED DESCRIPTION

Figure 1A:
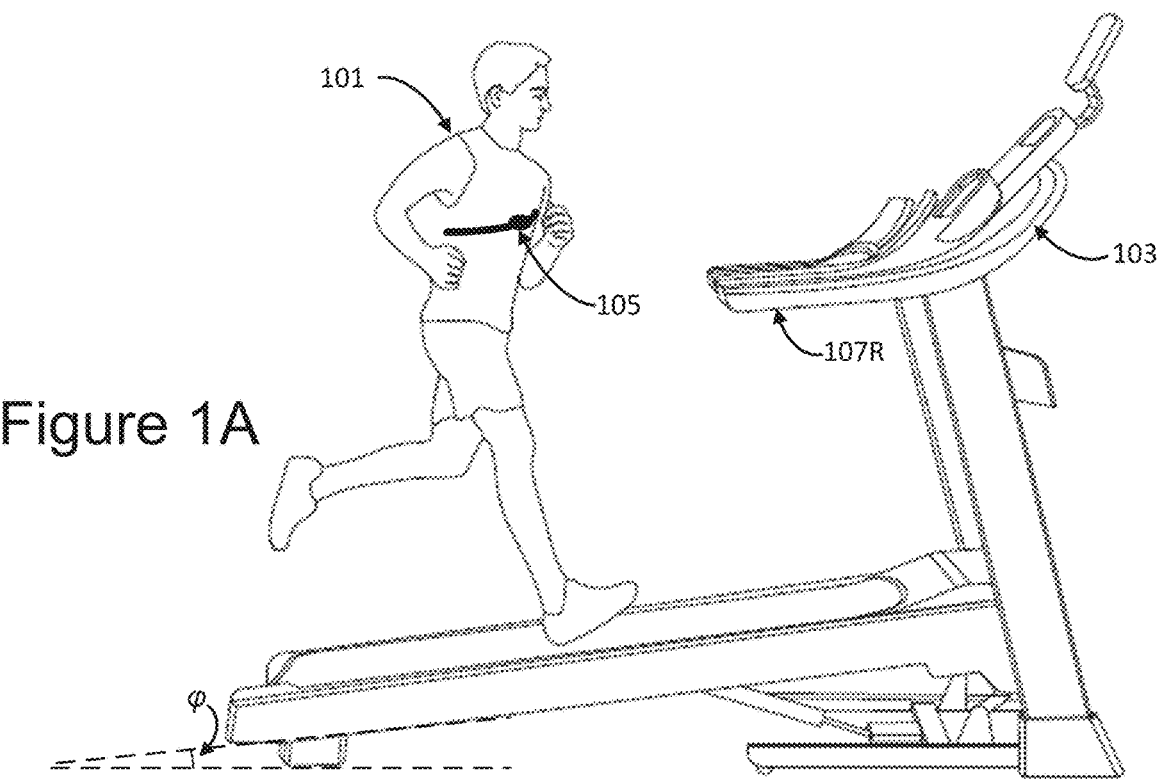
FIGS. 1A and 1B illustrate a subject exercising on a treadmill.

The following presents automated systems and methods for determining the physiological response of human or suitable animal subjects to physical exertion. The methods and systems can include monitoring sensors that capture the motion of the subject along with corresponding physiological data, and can track such motion for the duration of a period of physical exertion. In other aspects, the system is able to acquire an initial stream of physiological data from the subject during a range of physical exertion activities that are representative of the events intended to be monitored with the proposed method and system, enabling a corresponding dynamic physiological response model to be created. The motion tracking system and physiological response model can then be used to predict the physiological response to physical exertion events under a prescribed framework, including applications during real-time event monitoring.

Physical activity and exercise are critical for the health, fitness and quality of life of humans, enabling more efficient function of the organs of the body, including the brain, heart, lungs, and muscles among others. It may also help prevent or delay the onset of many health problems and diseases, including type 2 diabetes, cancer and cardiovascular disease. It is thus important to be able to quantify the impact of various types and levels of physical activities on the physiological response of the human body in the short-term, as well as the mid-term and long-term. The physiological response of the cardiovascular system to physical activity is among the most researched fields in the health and fitness industries.

Incorporating aerobic exercise such as brisk walking, jogging, running, hiking, swimming, and biking, strength training such as weightlifting, as well as incorporating routines aimed at improving balance and flexibility, are key activities that correlate with improved health outcomes, fitness and quality of life. Monitoring of physiological signals during all of these activities, such as heart rate, is thus highly valuable in order to best manage the impact and associated benefits of physical activity.

Various techniques have been historically developed to monitor heart rate, including electrocardiography (ECG), which measures the electrical activity of the heart, and more recently photoplethysmography (PPG), which uses optical signals to measure small volume changes in the microvascular blood vessels. Other techniques include ballistocardiography (BCG), which measures heart beats by monitoring ballistic forces generated by the heart, and imaging techniques, including imaging photoplethysmography (iPPG), which provides a non-contact estimation of heart rate by monitoring the elastic deformations on the subject's capillary vasculature on the skin subsurface induced by the PPG waveform.

Monitoring of heart rate using ECG technology during regular exercise on selected types of fitness equipment has become commonplace in the fitness industry. A very common method to monitor ECG-based heart rate is by using a chest strap, which is a device comprising electrodes to measure electrical impulses generated by the heart on a beat-to-beat basis. During a heartbeat, a feature in the ECG signal known as the QRS complex is used to create the timing associated with the beat. The QRS signal is the highest peak and most prominent feature of the ECG signal. Because of the proximity to the heart, chest straps tend to be very reliable, provided that a good contact between the electrodes and the chest is maintained. Proprietary algorithms are then used to compute a corresponding heart rate. Fitness enthusiasts have embraced this technology due to its accuracy and continuous acquisition capability. Wearing a chest strap, however, is also deemed to provide a level of discomfort that may reduce its appeal when monitoring heart rate.

An alternative ECG-based method is known as contact heart rate (CHR) monitoring technology, where a subject places both hands on corresponding conductive plates affixed to a fitness equipment instrumented with this technology, and the acquired ECG signal is monitored and used in the computation of heart rate. Good ECG signal integrity offers the opportunity to compute a highly accurate heart rate using this technology. In addition, one of the great benefits of fitness equipment instrumented with contact heart rate technology, is that the technology does not require the subject to wear a chest strap or any other device, and is always available.

Although these types of monitors can result in substantial heart rate accuracy, there are conditions arising from subjects with a smaller ECG QRS signal amplitude, that may reduce the ECG signal integrity used to track the heart beats. The quality of the ECG signal may also be affected by noise that can occasionally mitigate the accuracy of the signal extracted from the hands of human subjects. Moreover, the greatest limitation of this technology is related to the fact that users' comfort limits the length of time when hand contact is made with a given fitness equipment. While some fitness machines are more naturally conducive to keeping a hand grip, such as in the case of elliptical trainers and stationary/spin bikes, other machines, such as treadmills may be less conducive to holding a grip for extended periods of time, especially during faster speeds and lower incline levels.

Another heart rate monitoring method that has become quite prevalent is optical heart rate monitoring (OHRM) technology, based on PPG, which has been deployed in a mostly wrist-based wearable format. This technology offers a good level of accuracy for most users, but it also requires the subject to acquire an OHRM device, as well as wear it, while ensuring that the battery has enough charge throughout the training activity. Limitations may apply to individuals with hard-to-read optical signals, as well as from high noise levels arising from high intensity activities, among other sources.

Existing heart rate monitoring technologies can offer value as indicated above. One of the most salient benefits among these technologies is the relatively high signal quality often associated with ECG technology. There are also significant limitations associated with these technologies. In the case of chest strap technology, which can provide a highly accurate, continuous heart rate signal, this accuracy is typically hampered by the level of discomfort that many users associate with wearing the strap. In the case of contact heart rate technology, the signal is acquired by a comfortable grip of handlebars instrumented in many types of cardio fitness equipment. The heart rate signal is often highly accurate as well. The signal, however, is typically not amenable for continuous acquisition. OHRM technology, which may or may not provide the same level of accuracy as ECG-based technologies, also has the limitation, though arguably to a lesser extent than chest strap technology, as to the comfort level associated with having to wear the device during the monitored activity.

The following addresses many of these limitations, while providing a technology that can be used in conjunction with these existing technologies and partially replace or complement them on a variety of exercise settings, including the setting comprising fitness equipment instrumented with the proposed technology.

As mentioned above, physical activity and exercise are critical for the health, fitness and quality of life of humans, and thus the understanding of how to measure the intensity of the activity or exercise, and how it impacts heart rate and breathing is also critical. In particular, methods have been proposed to assess the relative intensity of physical activities, which can be categorized as having low intensity, such as walking at a normal pace, standing, and sitting; moderate intensity such as walking briskly, riding a bicycle at a moderate speed on a flat terrain, and ballroom dancing; and vigorous intensity such as jogging or running, swimming laps, and fast bicycling on even or uneven terrain.

A common method to measure physical activity intensity is known as the Borg scale, which is based on the correlation between heart rate and the subject's rating of perceived exertion (RPE), which estimates the level of effort and exertion, breathlessness and fatigue during a physical activity or exercise. The scale starts at a value of 6 and tops out at a value of 20 (with 6 corresponding to no exertion at all, and 20 corresponding to maximum effort). Using this range, subjects are asked to rate the perceived exertion for a particular activity, which is based on the subjective self-evaluation that correlates with the person's perceived heart rate, breathing rate, level of sweating and muscle fatigue. The scale was intended to be interpreted as a monitor of heart rate, which can be obtained by multiplying the perceived exertion level in this scale by a factor of 10. The "perceived heart rate" thus ranges from 60 to 200 bpm. Research has found a high correlation between RPE and heart rate.

The correlation between physical activity and exercise with actual heart rate is also important, as there are established guidelines as to the recommended target heart rate and estimated maximum heart rate for physical activity. The Centers for Disease Control and Prevention (CDC), which is the U.S. health protection agency, recognizes two types of aerobic activity based on activity intensity: moderate-intensity and vigorous-intensity activities. It also provides a specific guideline for what the target heart rate range should be for each of these two types of activities, based on the estimated age-related maximum heart rate for the individual. The target heart rate is recommended to be between 64% and 76%, and between 77% and 93% for moderate-intensity and vigorous-intensity activities, respectively. There is also a recommended prescription for how much of each of these activities individually, or combined, should be followed on a daily and weekly basis.

The following presents techniques to address the correlation between physical activity and heart rate and it is described below, based on an exemplary embodiment using a treadmill, which represents one of the most popular machines in both the commercial and home fitness industry.

In the following, the discussion will often be presented in the context of treadmill embodiments. Treadmills provide users with the option to select from a range of speeds that may typically reach up to 10 mph to 12 mph (16.1 kph to 19.3 kph), as well as a range of incline levels that can typically reach up to at least 15%. This makes the treadmill a convenient example to illustrate many the of concepts presented here, but it will be understood that the techniques described are more generally applicable and a number of alternate embodiments will also be provided.

Figure 1B:
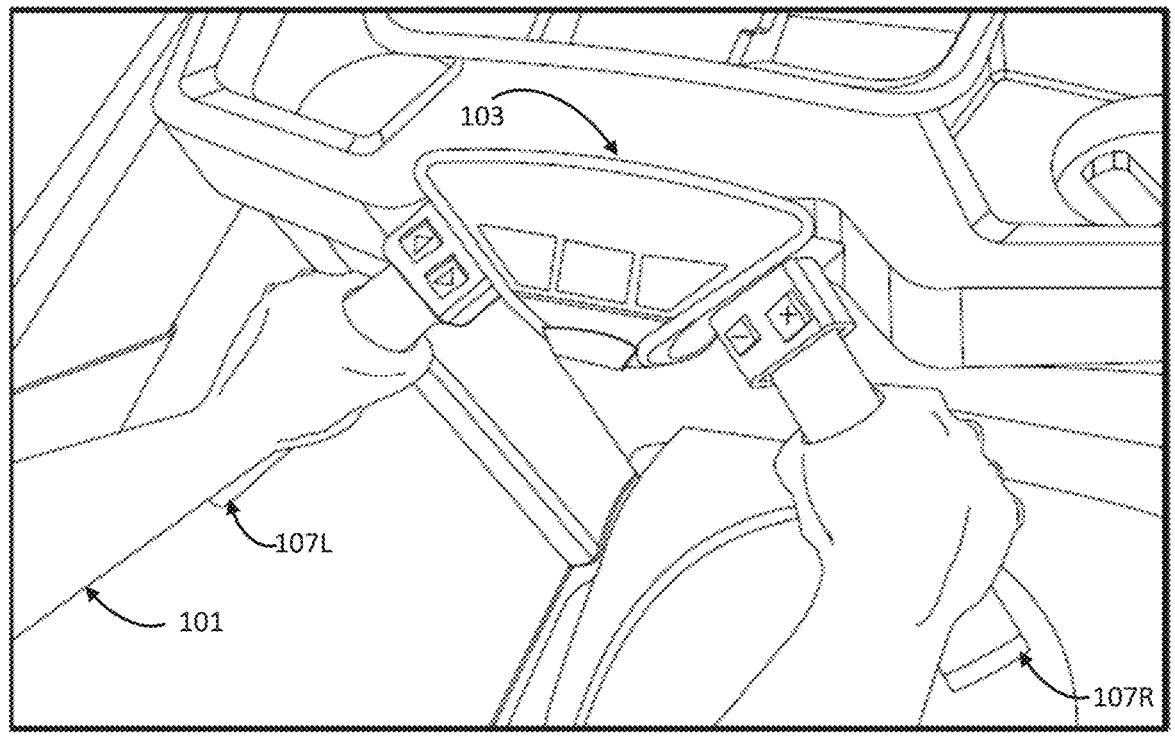

FIGS. 1A and 1B illustrate a subject 101 on a treadmill 103 adjusted to have an incline (p. A typical run on a treadmill may include a warm-up for 2 minutes at a pace of 2 mph, a 3 mile run at an average speed of 5 mph, which would take 36 minutes, and a cool-down for 3 minutes at 2 mph, for example. The total activity would thus take 41 minutes. FIG. 1A can be an illustration of a subject conducting a treadmill activity protocol, such as the exemplary protocol described here. To monitor heart rate, the user may wear a chest strap for the duration of the activity, as depicted at 105. Optionally, the subject may place the hands on the left and right conductive plates 107L and 107R of the handlebar commonly found on treadmills, which are used for contact heart rate monitoring, as illustrated in the detail of FIG. 1B. Other exercise equipment, such as a spin bike, can similarly incorporate such conductive plates into their handlebars or similar structures.

In the case when the user wears a chest strap during the treadmill run described in this example, the user is likely to have an accurate record of the heart rate during the entire exercise, but would have also been subjected to the possible discomfort of wearing the chest strap. A representative illustration of the subject's heart rate during this treadmill exercise protocol is illustrated in FIG. 2.

Figure 2:
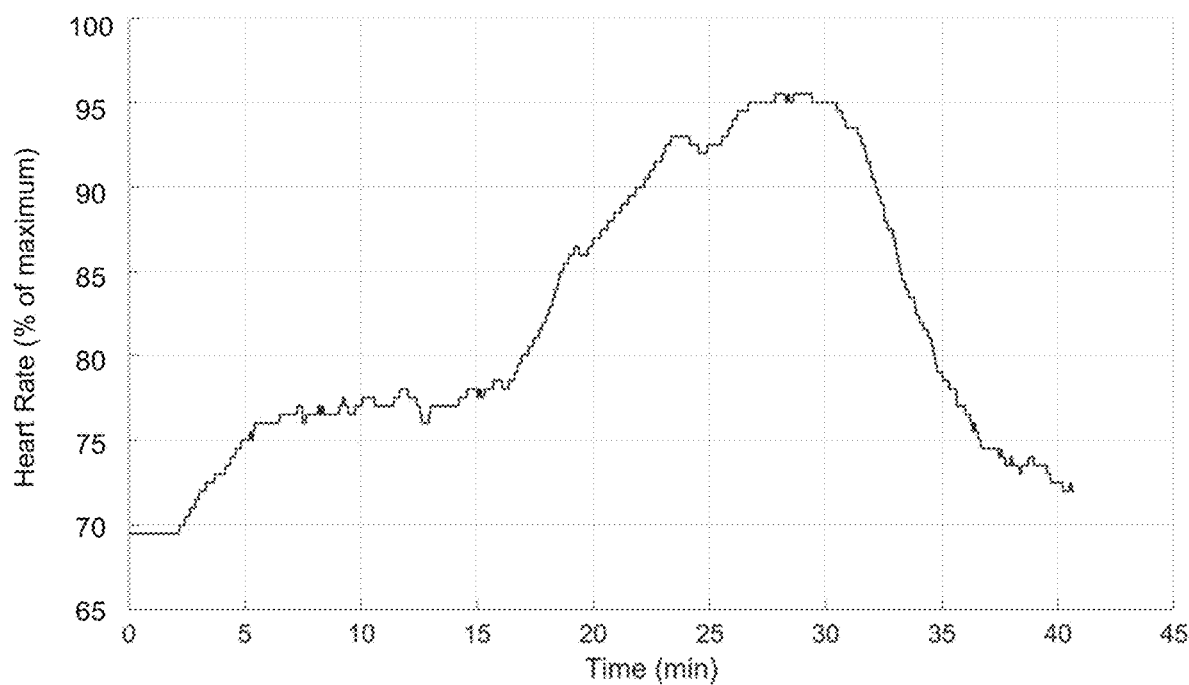
FIG. 2 illustrates a subject's heart rate during a treadmill exercise protocol using a continuous heart rate monitor, such as a chest strap monitor.

FIG. 2 illustrates a subject's heart rate during a treadmill exercise protocol using a continuous heart rate monitor, such as a chest strap monitor. The graph of FIG. 2 shows the subject's heart rate as a percentage of maximum heart rate over the 41 minute exemplary active described above, with two minutes of warm-up at 2 mph where the heart rate stays near the initial heart rate, followed by 36 minutes at 5 mph during which the heart rate ramps up, levels off, and begins to drop, and then followed by 3 minutes of cool-down at 2 mph.

In the absence of a chest strap 105 or user worn heart rate monitor, the subject 101 can use the contact heart rate technology, such as the had grips 107L, 107R of FIG. 1B to monitor the heart rate. In this case, a typical subject 101 may hold onto the hand grips 107L, 107R for a portion or the entire warm-up period, hold onto the hand grips occasionally during the 3 mile run, such as 3 times for 30 seconds at the 0.5, 1.5 and 2.5 mile event markers, and for the first 2 minutes of the cool-down step, which is one example of protocol to be followed. In this example, the user is likely to have an accurate record of the heart rate during these periods, when hand contact is made onto the contact heart rate monitor, but without the possible discomfort of wearing the chest strap.

The initial 2 minute period (or portion thereof) of heart rate monitoring during warm-up would provide the subject with a valuable piece of information as to what the value of the resting heart rate prior to commencing the treadmill activity was. Conversely, if the subject had been engaged in a physical activity right before coming to the treadmill, then the heart rate monitored during the warm-up period may not correspond to a resting heart rate, but it would instead provide the subject's initial heart rate trajectory, prior to the 3 mile run on the treadmill. The three 30 second segments of data taken during the 3 mile run would provide the subject with information as to the trajectory of the heart rate, which is expected to be largely increasing during the continuous 36 minute run. The 2 minute period of heart rate data during the concluding cool-down period, would also provide the subject with knowledge as to the heart rate recovery after the 3 mile treadmill-run activity. These multiple data segments, when combined, provide valuable information related to the health and fitness of subjects.

Figure 3:
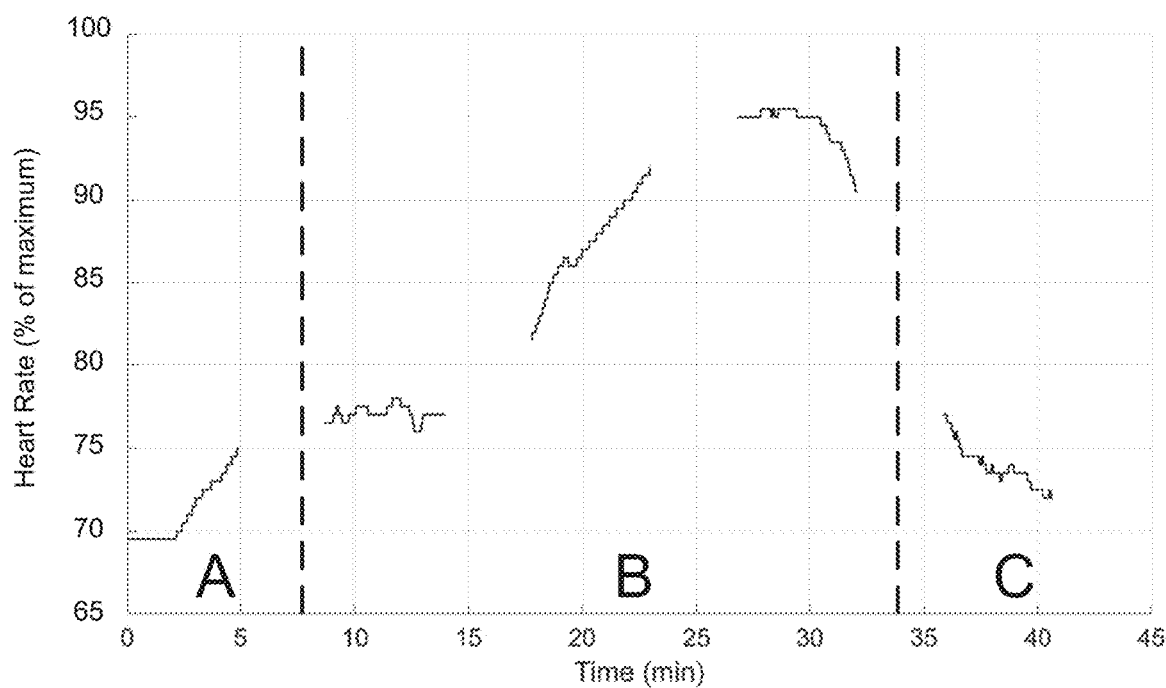
FIG. 3 illustrates a subject's heart rate during a treadmill exercise protocol using a non-continuous heart rate monitor, such as a contact heart rate monitor.

FIG. 3 illustrates a subject's heart rate during a treadmill exercise protocol using a non-continuous heart rate monitor, such as a contact heart rate monitor. FIG. 3 can correspond to the same subject's heart rate during the same treadmill exercise protocol as in FIG. 2, but where the heat rate data acquired is non-continuous. This protocol has the three portions of a 2 minute warm-up data segment (section A), the three 30 second data segments during the 3 mile run (section B), and the 2 minute cool-down data segment (section C). For the purpose of reference, this treadmill protocol will be labelled as "Treadmill_Protocol_1".

The heart rate behavior illustrated in FIGS. 2 and 3 is typical of a treadmill protocol such as Treadmill_Protocol_1; that is, during a resting heart rate phase, prior to the 3 mile run, it is expected that the heart rate of a subject would be constrained to vary within a small range, corresponding to a limited amount of variability related to the subject's specific state of equilibrium, also known as homeostasis. Some people will have a larger range of heart rate variation during a period of rest than others, but the heart rate would typically be constrained within a small range, such as of +/−5 beats per minute (bpm), for example. If the subject had started the treadmill protocol after completing a previous physical activity, the heart rate may be expected to potentially change within a larger range, as it would for example be the case, if the heart rate were to be dropping from values reached during the previous physical activity.

During the 3 mile run, however, the heart rate of the subject is expected to increase with a rate that is commensurate with the level of effort of the individual, in order to follow the 3 mile at 5 mph protocol step. For some individuals, the 5 mph level of exertion would be quite easy, especially for people with a high level of fitness, and who exercise under similar protocols frequently. For other individuals, this activity may be harder to accomplish. The intrinsic characteristics of the individual will also play a role in the particular behavior of the heart rate signal for this protocol. Finally, the current state of the individual may also impact the heart rate signal. This could be a result of any previous activity the subject may have been engaged in prior to pursuing this protocol, the level of readiness to accomplish the exercise that may be related, for instance, to the amount and quality of sleep in the day or days prior to this event, as well as the subject's emotional state. During the 2 minute cool-down period, the heart-rate value is expected to drop more or less rapidly, depending again on the intrinsic characteristics of the subject. Overall health and wellness may also play a role in how the heart-rate behavior responds to the exercise load and entire protocol.

In the above scenario of a subject conducting Treadmill_Protocol_1, it is expected that the general body motion sequence and associated level of effort employed by the subject would be highly correlated to the specific details of the protocol. Thus, a close adherence to a protocol, such as Treadmill_Protocol_1, could serve as a first indication of the level of effort a subject is carrying out. The closer a subject follows the protocol, the closer the expected response of the human body would be to such protocol. Further, if the subject were to repeat the same identical protocol on multiple occasions, it would be expected that a similar human body response would ensue. This approach, however, has some significant drawbacks. For example, an issue with the above method is that the initial heart rate is expected to be different on different occasions. Further, the prior history of the subject's body physiological state is not known.

The information related to the immediate period of time prior to carrying out a protocol, such as Treadmill_Protocol_1, can be incorporated into the determinations. Thus, not only the initial (instantaneous) value of the physiological state is required to be known, but also the initial dynamic variation of such state. In the particular case where the physiological state of interest is the heart rate of the subject, then we not only need to know the value of the initial heart rate, but also whether the heart rate is stable, or is for instance decreasing, as would be the case if the subject had just ended a prior physical activity. In the latter case, a correspondingly elevated heart rate would still be recovering toward a lower resting heart rate value as the subject approached the treadmill. Other scenarios could be entertained, but there is a need to understand this dynamic physiological state prior to creating a model to track the subject's exertion level. Once the subject commences the protocol, the physiological response of the subject will tend to be dominated by the protocol itself.

Another limitation of just using a protocol to predict the level of exertion of the subject comes from a combination of multiple factors that jointly would dominate a continuous minor or major departure from the expected exertion suggested by such protocol. One factor would be the level of readiness or lack thereof to carry out the protocol, which may be related to physical causes such as fatigue, illness or some minor injury, and which may limit full adherence to the protocol. A second factor may be psychological and may be related to stress or to lack of will or engagement in following the protocol as effectively as possible. Additional factors may be related to the inherent ability of the subject to follow the protocol due to the level of difficulty of the protocol itself for a given subject, which may limit how smoothly the protocol can be adhered to. All of these potential factors may require various levels of effort by a given individual to follow an otherwise identical protocol over multiple occasions. Thus, a real-time monitor that can sense the level of effort continuously can improve upon this situation.

One method of capturing the level of effort exerted using a protocol, such as Treadmill_Protocol_1, is by using a wearable device, which can be denoted here as a "human wearable device", that is capable of sensing the subject's physical activity. A very common sensor that can be used for this purpose is an inertial measurement unit (IMU) that can integrate measurement devices including accelerometers, gyroscopes, magnetometers and optionally, barometric pressure sensors.

Figure 4:
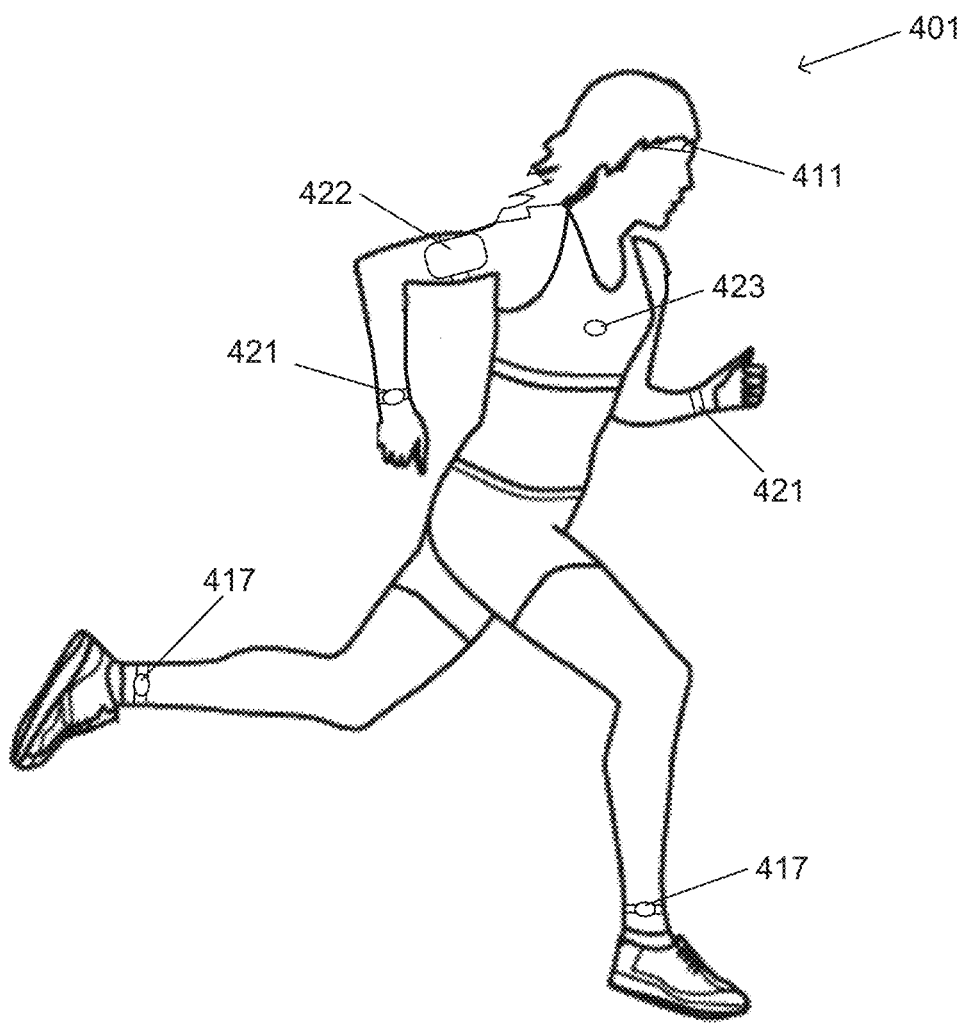
FIG. 4 illustrates examples of wearable devices that can serve as exertion monitors.

FIG. 4 illustrates examples of wearable devices that can serve to provide valuable information in the development of exertion monitors. FIG. 4 shows a subject 401, here a human, using a number of examples of a wearable device, which can be mounted on the subject's head, such as on a helmet, headband 411, ear/earlobe device, glasses, or on other body locations, including a chest patch 423, an arm band 422, a watch 421, a belt, a thigh/leg strap, a finger clamp, an ankle bracelet 417, a shoe, or other devices. During a physical activity protocol, each of these locations will yield different signal patterns depending on the specific motion of the body where the sensor is attached. The accelerometer signals, for example, would provide a measurement of the front-and-back, side-to-side, and up-and-down acceleration of the body movement at such location, which in this example are denoted as x-axis, y-axis and z-axis, respectively.

When an inertial measurement unit is mounted on the head 411 of the subject 401, for example, the three axes will closely be associated with the actual body movement, as the relative head motion is naturally limited during a protocol, such as Treadmill_Protocol_1 as used in this example. Accelerometer signals proceeding from a chest patch 423, for example, would also mimic the motion of the body. They may include, however, additional components in the accelerometer axes that are aligned with subject's front-to-back (x) axis and left-to-right (y) axis, as a result of a possible minor movement of the chest relative to the body. Accelerometer signals proceeding from sensors 421 mounted on the limbs will follow more complex patterns, which can also be analyzed to establish the effective level of effort of a subject carrying out Treadmill_Protocol_1. An accelerometer mounted on a waist belt, for example, would generate a potentially simpler signal to analyze in correspondence to body motion and associated level of effort.

Accelerometer signals from any of these body locations will be representative of the level of effort that takes place in real time, during the course of carrying out Treadmill_Protocol_1. Thus, the following of such protocol, while using a human wearable device instrumented with an IMU, will result in signals that will vary each time the identical protocol is carried out, corresponding with the subject's exact performance on each occasion. This is illustrated in FIGS. 5A-5D.

Figure 5A:
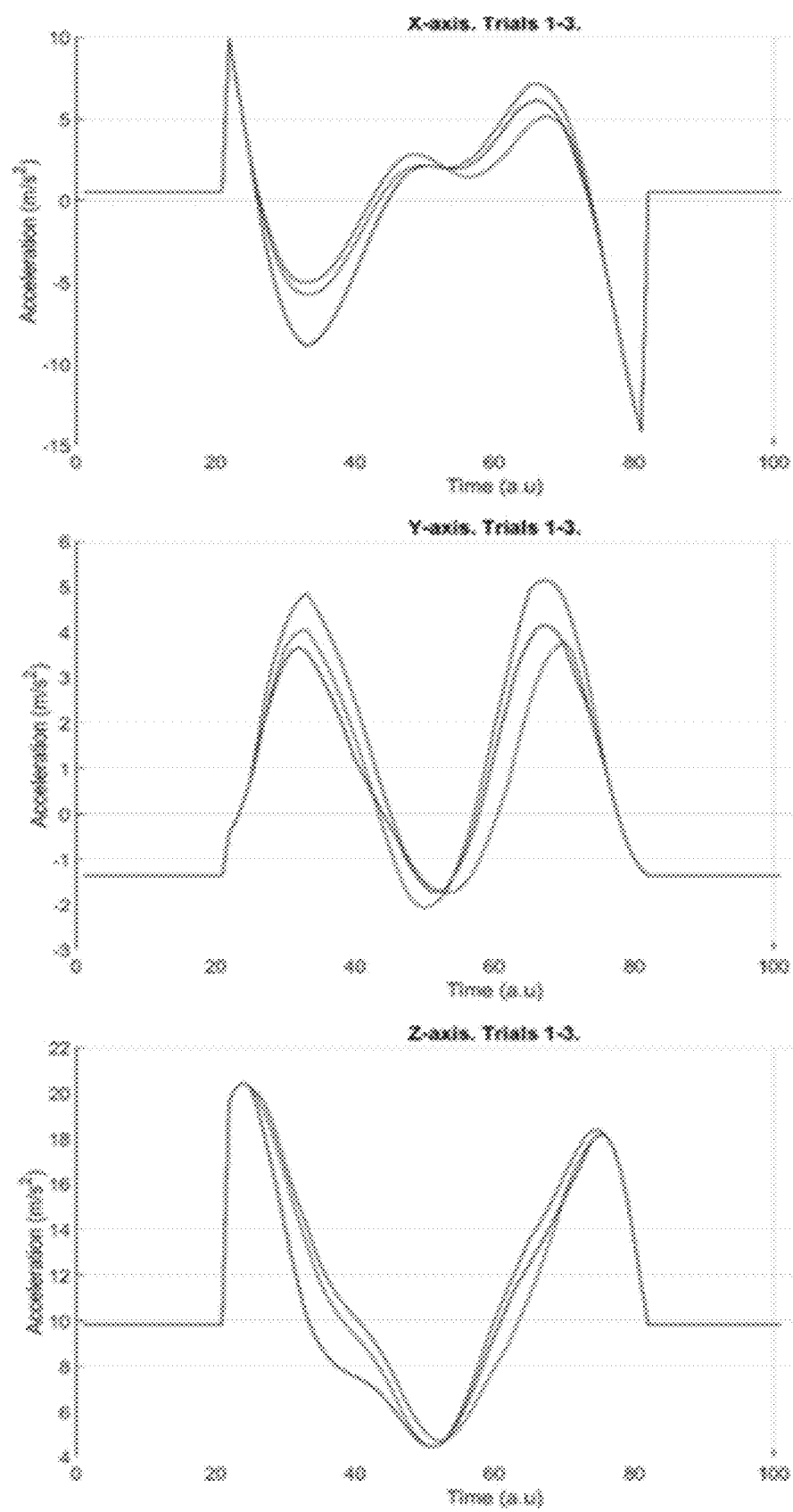
FIGS. 5A-5D each illustrate a set of signals from a wearable device instrumented with an inertial measurement unit (IMU) as a result of the subject's performance when a protocol is carried out.

FIGS. 5A-5D each illustrate a set of signals from a wearable device instrumented with an IMU as a result of the subject's performance when a protocol is carried out. FIG. 5A is data generated by a subject following the same protocol in three trials while using a wearable device instrumented with an IMU. This will result in accelerometer signals whose amplitude (vertical axes) over time (horizontal axes) will vary each time the protocol is carried out, as a result of variations in the subject's exact performance on each.

Figure 5B:
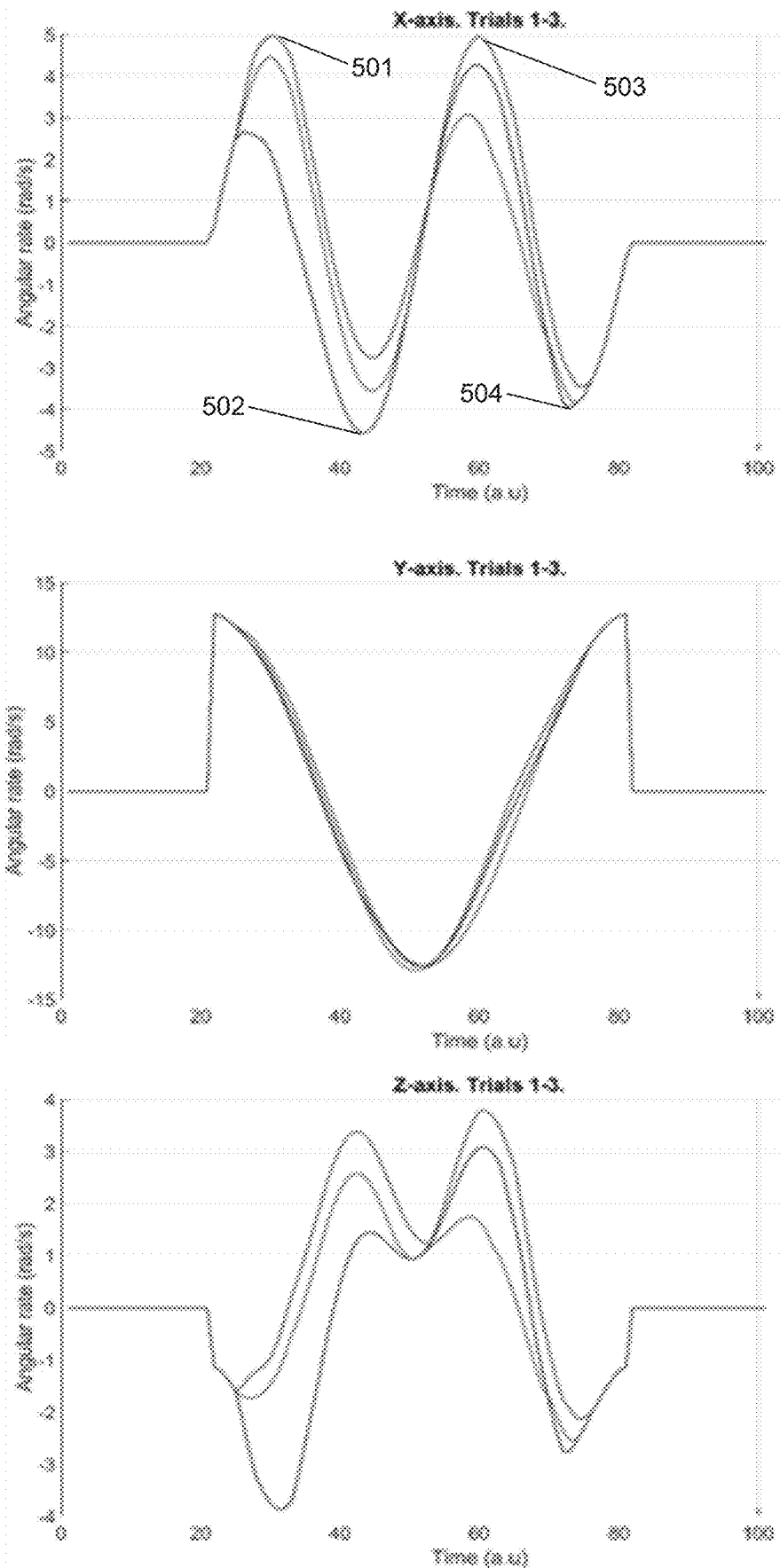

A similar characterization and discussion of the level of effort exerted by the subject can be conducted by analyzing gyroscope signals from similar IMU locations on a subject's body. As a result, the angular velocity around each axis can be monitored, and in turn the motion of the body where the IMU is mounted could be monitored and correlated with the subject's level of effort while carrying out Treadmill_Protocol_1, as illustrated in FIG. 5B. FIG. 5B again illustrates a subject following the same protocol while using a wearable device instrumented with an IMU. In FIG. 5B, the vertical axis corresponds to angular velocity of the gyroscope in degree per second and horizontal is time. During the protocol, the gyroscope's signals will vary each time the protocol is carried out as a result of variations in the subject's performance for each instance, but will typically exhibit recurrent features (labeled 501, 502, 503, 504) corresponding to, for example, the same point in the subject's stride while executing the protocol. Depending on the specific mounting location of the IMU, the signals from the gyroscope may yield a weaker correlation to the level of effort exerted by the subject when compared to the signals resulting from the accelerometer. Nonetheless, the combination of both accelerometer and gyroscope signals is likely to produce a closer representation of the subject's level of effort than using either of these signals alone.

Figure 5C:
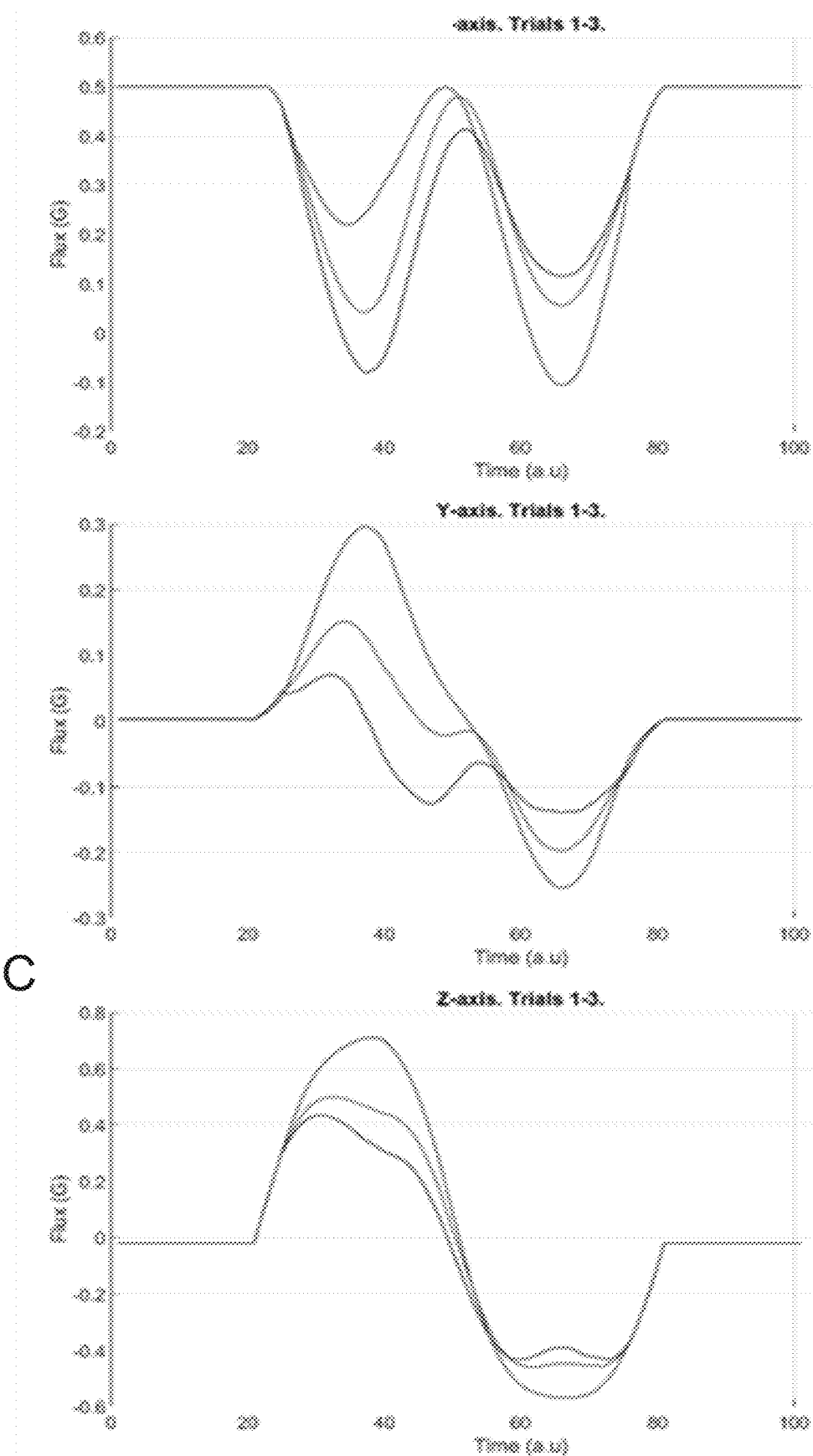

Another example of utilizing an IMU on a human wearable device to characterize the level of effort exerted by the subject could be conducted by analyzing magnetometer signals from similar IMU locations on the subject's body. The variability of the detected magnetic heading could be correlated, to some extent, with the level of effort exerted by the user. When combined with the information proceeding from the accelerometer, gyroscope, or both, for example, a closer representation of the subject's level of exertion could likely be attained. A typical signal from an IMU magnetometer is shown in FIG. 5C, displaying the information in each of the three axes, corresponding to three trials following the same protocol. The combination of all the data captured with the IMU can be used to compute roll, pitch and yaw characteristics of the motion over time. The graphs of FIG. 5C correspond to the same protocol as FIGS. 5A and 5B.

Figure 5D:
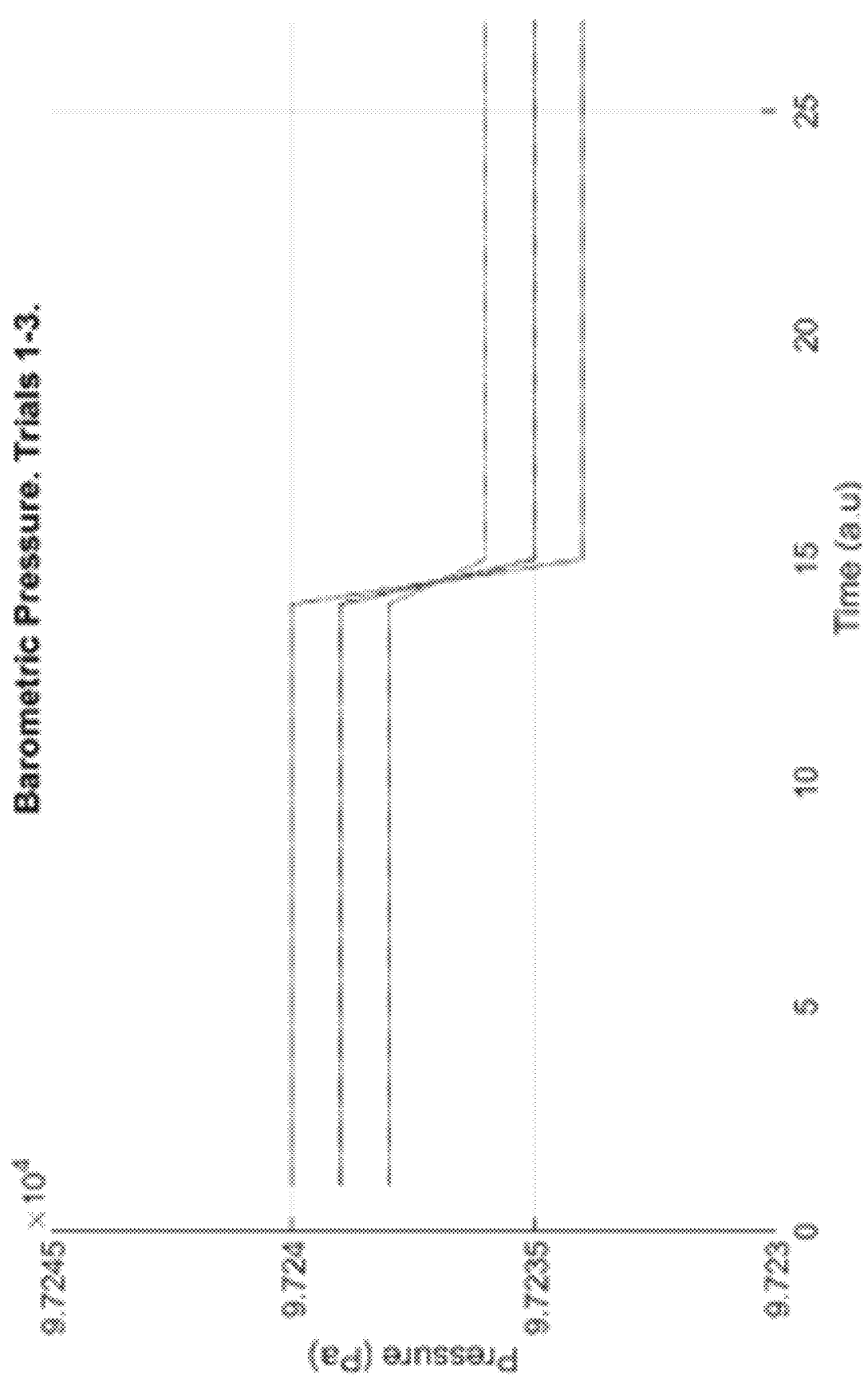

A further example that can be incorporated into some embodiments can include the use of a barometric pressure sensor within the IMU, which has been used to discriminate between sitting and standing body position transitions in studies of sedentary behavior. The additional relative-elevation signal variability induced by the small change in pressure that, when combined with the information from the accelerometer along with the gyroscope and the magnetometer, for example, would be expected to again result in a closer representation of the subject's level of exertion. A typical signal from an IMU barometric pressure sensor is shown in FIG. 5D for a signal obtained from a protocol that includes transitions alternating between sitting and standing. In FIG. 5D, the vertical axis illustrates the pressure (in Pascals) for a higher pressure, sitting phase with an average "before" pressure followed, after a pair of time gaps before and after standing (at the transition time at the broken line), by a lower pressure, standing phase with an "after" pressure. Such pressure variations can also be used when exercising over terrain that involves changes in altitude, such as climbing while running or hiking.

Depending on the embodiment, these metrics or a combination of these metrics can provide an improved ability to correlate the motion of the subject while carrying out Treadmill_Protocol_1 or other protocol and the real-time level of effort exerted by the subject.

As stated earlier, using a chest strap or other wearable device during an exercise activity may be deemed uncomfortable by many individuals. In some embodiments, rather than employ user wearable sensors to capture the level of effort exerted by a subject following a protocol, such as Treadmill_Protocol_1, while still using exertion monitors such as an inertial measurement unit (IMU), we can instead place the burden of providing the "physical activity" monitor on the exercise equipment, making the machine "wear" the sensor or sensors of the exertion monitors.

For example, the exertion monitors to measure physical activity can be incorporated into the exercise equipment, such as the treadmill of FIGS. 1A and 1B, a spin bike, or other exercise equipment, to remove the need for, or compliment the use of, the subject to use a human wearable device. Physical activity created by the subject, while on the fitness or exercise equipment, is transferred to some degree to the machine based on fundamental laws of physics. Thus, an exertion monitor incorporated into or placed on a treadmill, as the exemplary embodiment presented in this example, can reflect signals that are commensurate to the motion, and more importantly reflective of the level of effort deployed by the subject.

Figure 6A:
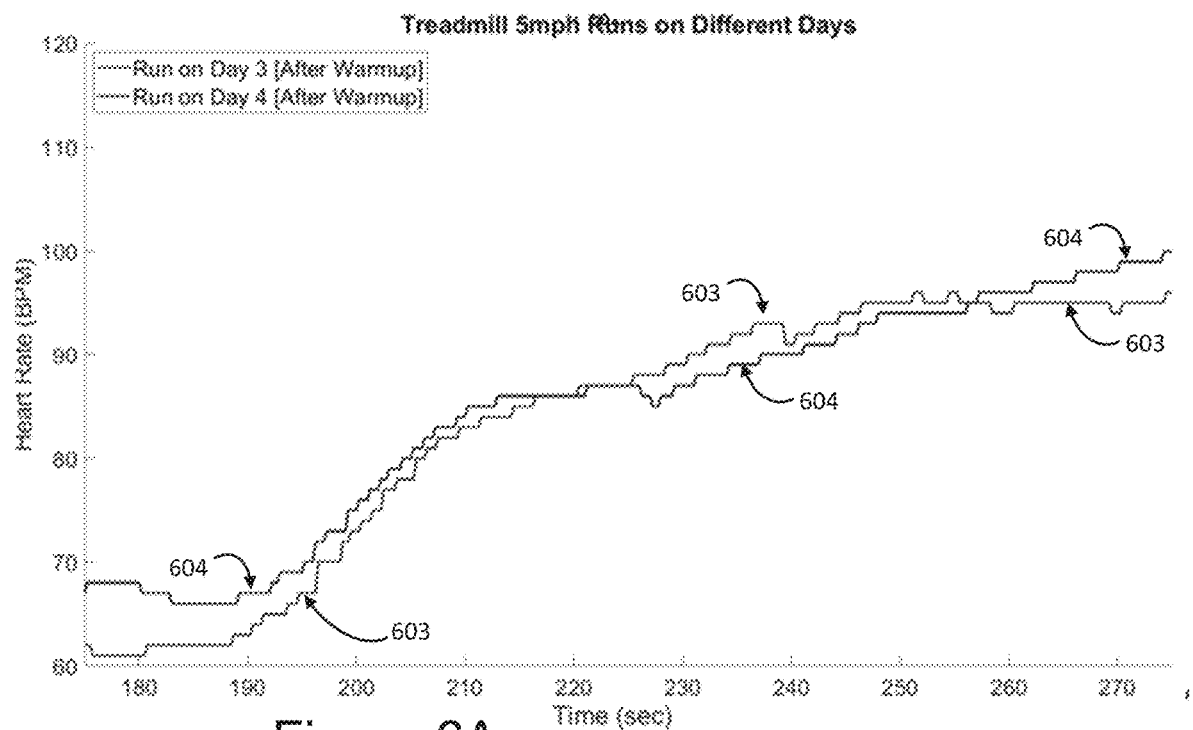
FIG. 6A illustrates heart rate signals for 5 mph runs after a warm-up for data collected on two different days.

FIG. 6A shows one application of this approach on a 100 second time window during the transition from a warm-up to a 5 mph run, such as described in Treadmill_Protocol_1. The protocol activity was pursued on two different days: Day 3 and Day 4. The subject was wearing a chest strap, which was used to create the data for this activity, where 603 corresponds to Day 3 heat rate data and 604 to Day 4 heart rate data. Different resting heart values 62 bpm (on Day 3) and 67 bpm (on Day 4) both yielded similar, although not identical results. The results on Day 3 show a slightly faster rise compared to the data from Day 4.

Figure 6B:
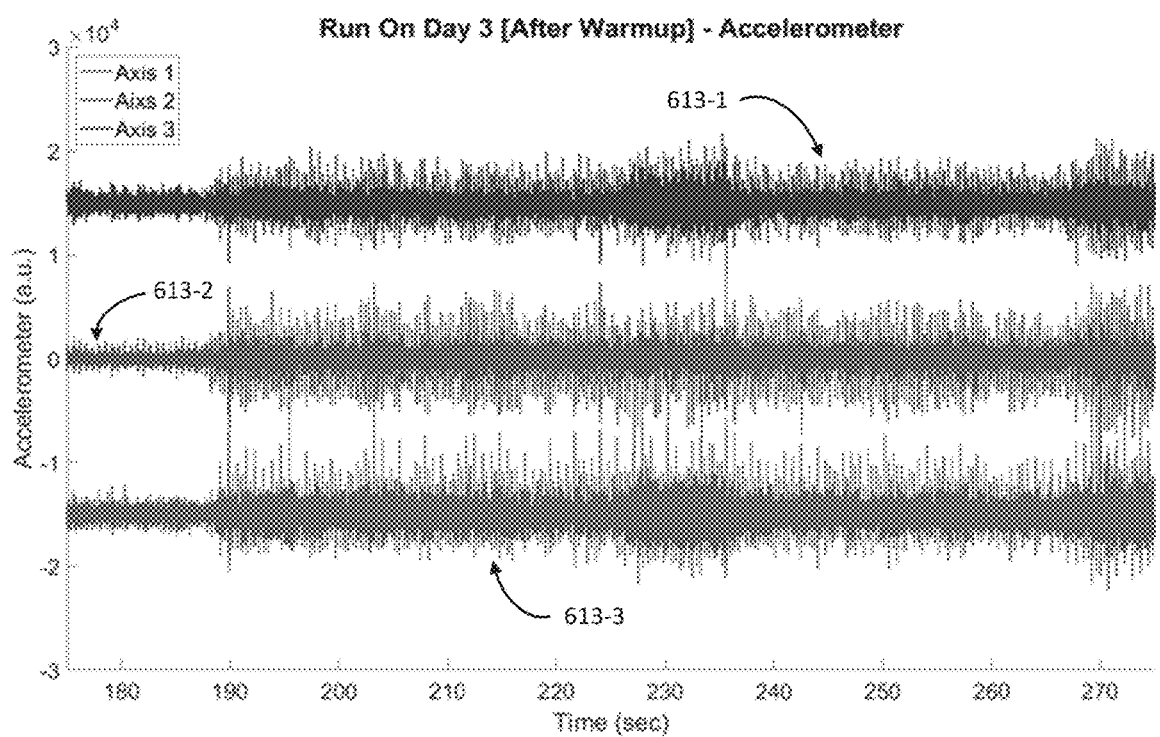
FIGS. 6B and 6C illustrate accelerometer signals for 5 mph runs after a warm-up for data collected on two different days along with data shown in FIG. 6A.
Figure 6C:
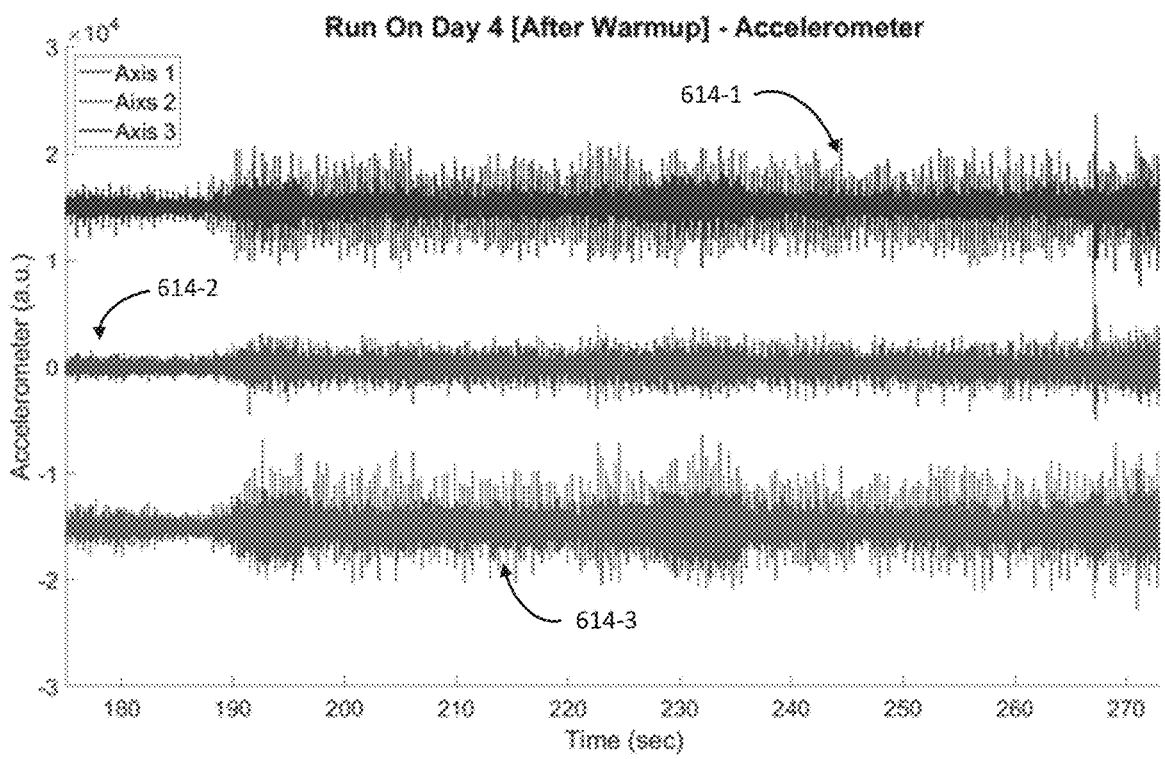

FIGS. 6B and 6C show IMU accelerometer data for the runs of FIG. 6A with the accelerometer recording the data directly from the treadmill, where FIG. 6B shows the Day 3 data for accelerometer axes 1, 2, and 3 respectively as 613-1, 613-2, and 613-3, and FIG. 6C shows the Day 4 data for accelerometer axes 1, 2, and 3 respectively as 614-1, 614-2, and 614-3, where the accelerometer data is in arbitrary units.

The raw data shown indicate a slightly more intense response on the accelerometer on Day 3, compared with the data collected on Day 4, corresponding with the higher heart rate response for Day 3, shown in FIG. 6A.

Figure 7A:
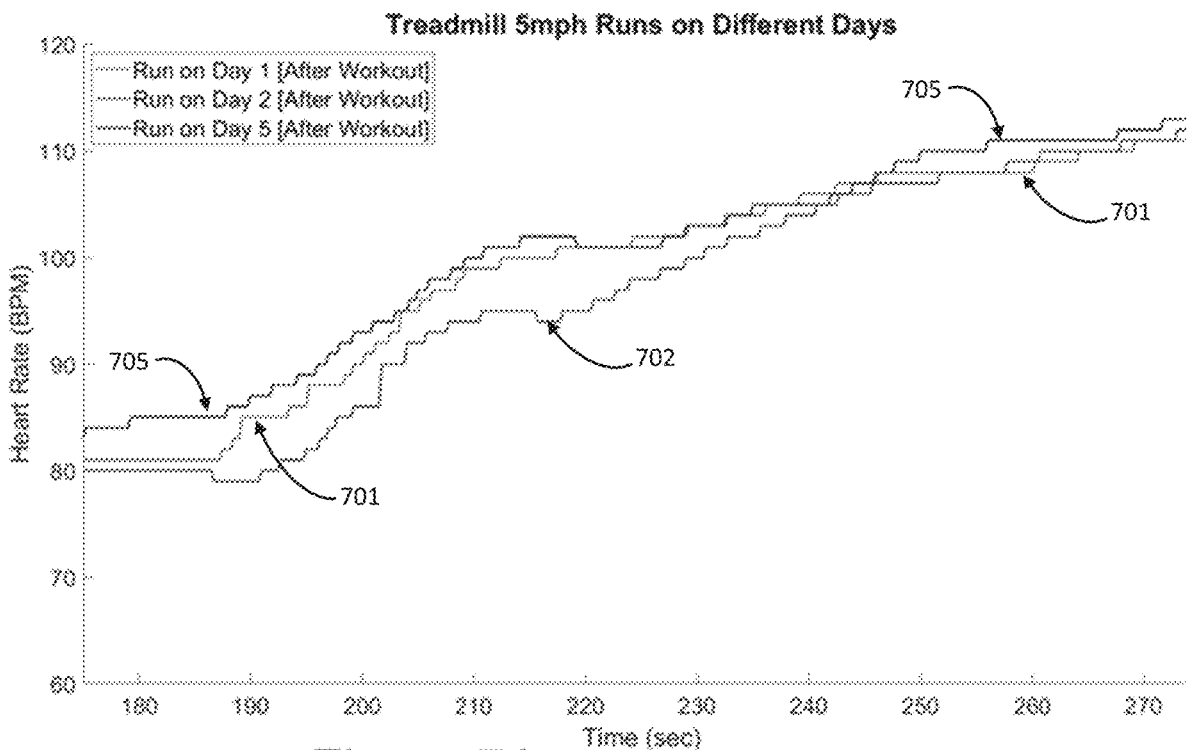
FIG. 7A illustrates heart rate signals for 5 mph runs after a workout for data collected on three different days.

FIGS. 7A-7D illustrate three additional data sets were collected using Treadmill_Protocol_1, but for these sets the subject had completed another cardio activity, immediately prior to the treadmill activity. FIG. 7A illustrates heart rate signals for 5 mph runs after a workout for data collected on three different days, Day 1 at 701, Day 2 at 702, and Day 5 at 705. The initial heart rate values also varied slightly in the range of 80 to 83 bpm, but the heart rate response to the 5 mph exertion task all again yielded similar, although not identical results. The results 705 on Day 5 show a slightly faster, consistent rise compared to the data 701 from Day 1, and both data sets show a comparably larger heart-rate rise response than the data 702 collected on Day 2.

Figure 7B:
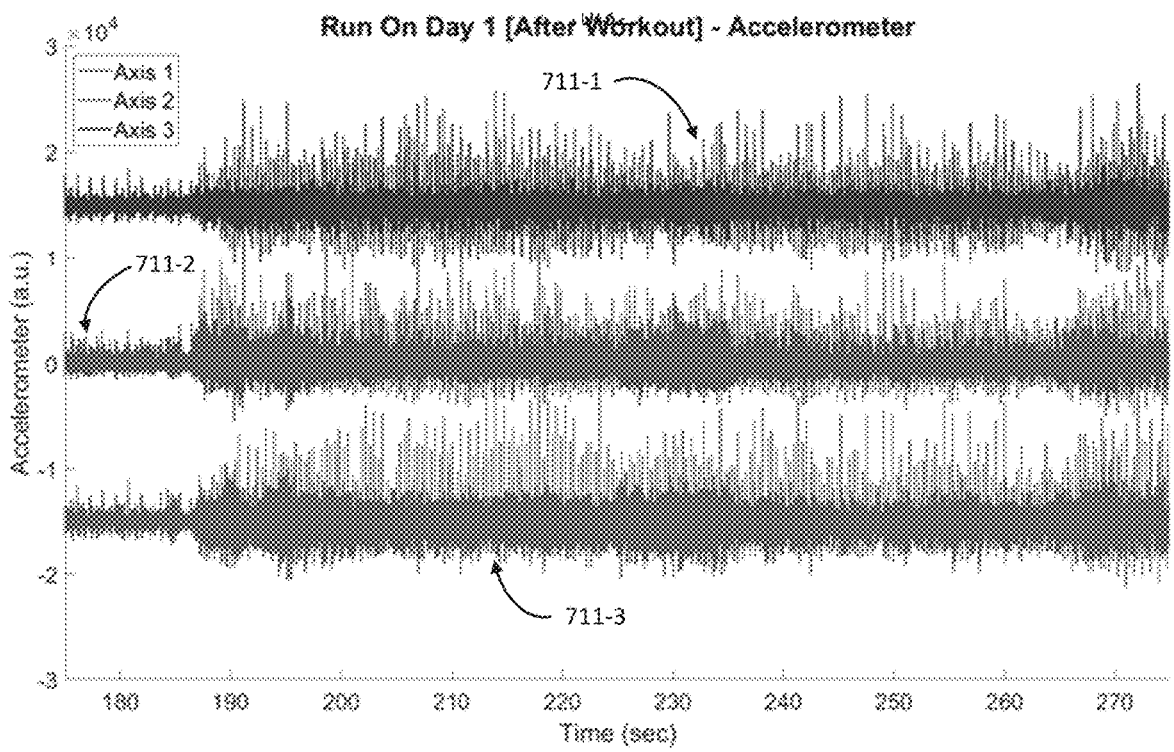
FIGS. 7B-7D illustrate accelerometer signals for 5 mph runs after a workout for data collected on three different days along with data shown in FIG. 7A.
Figure 7C:
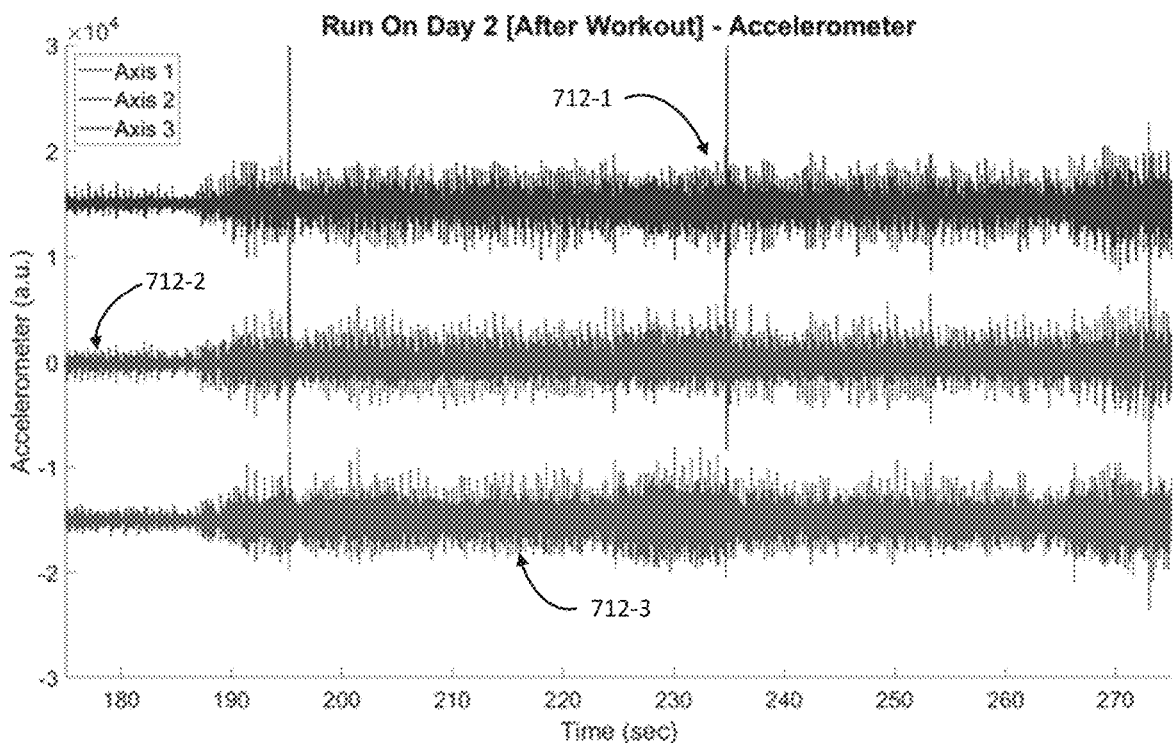
Figure 7D:
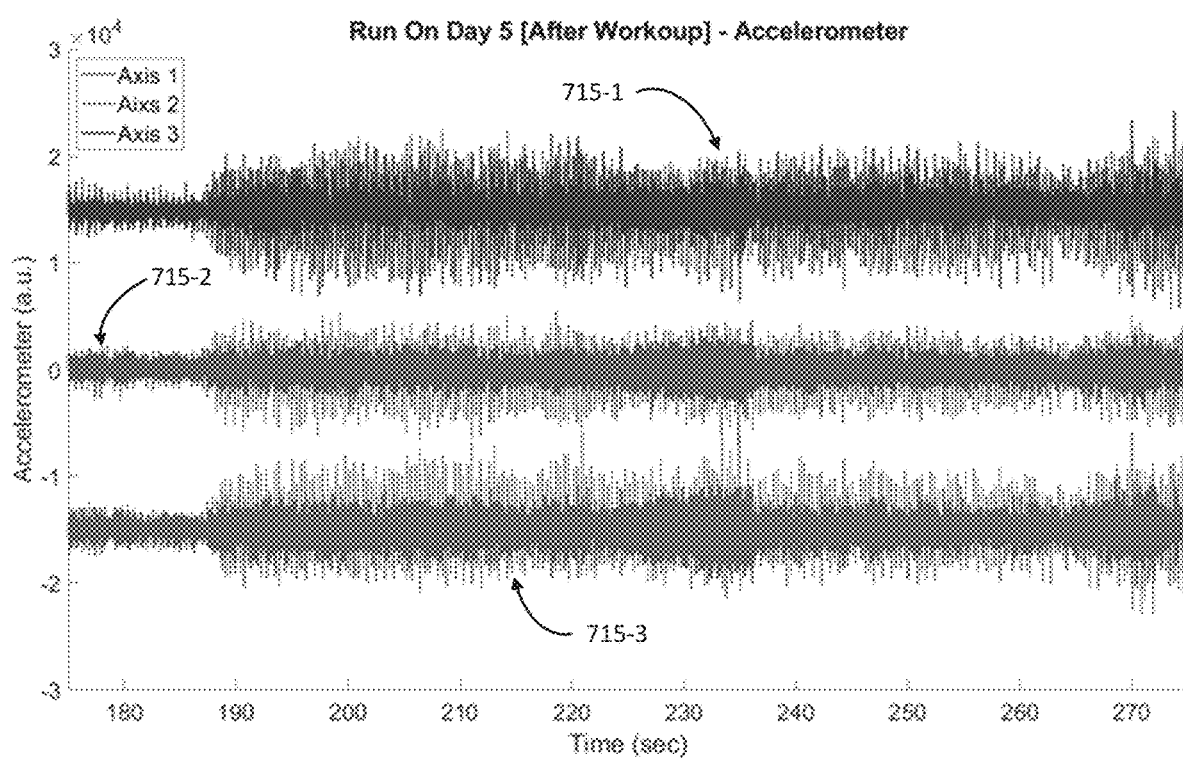

FIGS. 7B-7D show IMU accelerometer data for these runs, with the accelerometer again recording the data directly from the treadmill as in FIGS. 6B and 6C, where Day 1 data for accelerometer axes 1, 2, and 3 respectively as 711-1, 711-2, and 711-3; Day 2 data for accelerometer axes 1, 2, and 3 respectively as 712-1, 712-2, and 712-3; and Day 5 data for accelerometer axes 1, 2, and 3 respectively as 715-1, 715-2, and 715-3. The raw data sets shown indicate a slightly more intense response on the accelerometer on Day 5, compared with the data collected on Day 1, and both data sets show higher intensity signals than the data collected on Day 2. These results are again in agreement with the corresponding heart rate responses, shown in FIG. 7A.

Figure 8A:
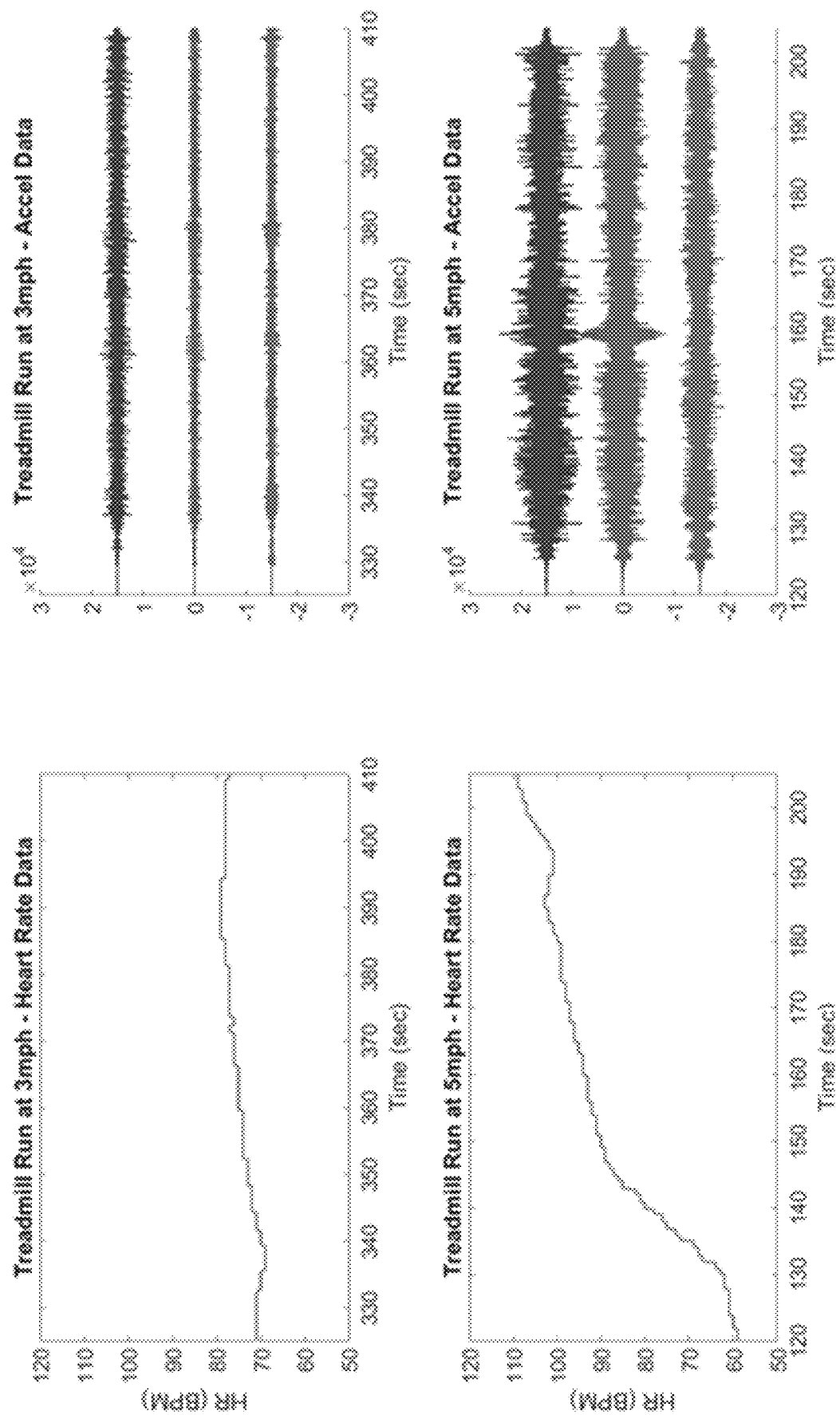
FIGS. 8A and 8B present examples of heart signals and corresponding accelerometer signals for runs after a progressive workout.

FIG. 8A illustrates a similar data set collected with the IMU mounted on the treadmill on an 85 second time window, during the transition from warm-up to the treadmill run. In this example, the exercise target speed was varied from warm-up to either 3 mph or 5 mph, where top left shows the 3 mph heart rate, top right the corresponding 3 mph accelerometer values, bottom left the 5 mph heart rate, and bottom right the corresponding 5 mph accelerometer values. As expected, the significant difference in level of effort targets is reflected in the small heart-rate rise response for the lower level of effort shown in FIG. 8A, top left, as well as the larger heart-rate rise response for the higher level of effort shown in FIG. 8A, bottom left. Correspondingly, the significantly smaller accelerometer signal in FIG. 8A, top right, when compared to the signal on FIG. 8A, bottom right, appears as expected.

Figure 8B:
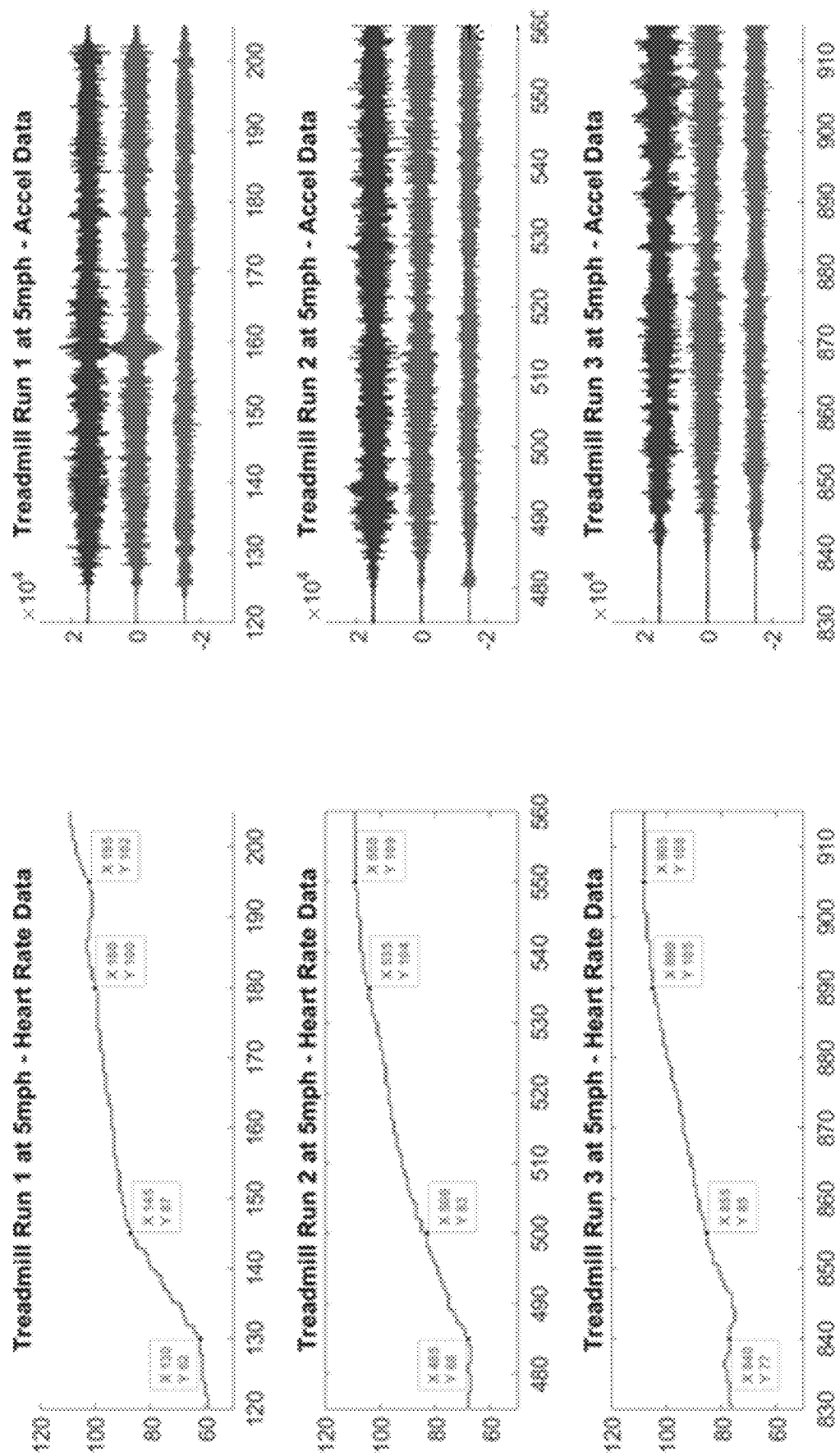

FIG. 8B shows additional runs using Treadmill_Protocol_1 conducted on the same day as that of FIG. 8A. At left, FIG. 8B shows heart rate signals for three 5 mph runs after a progressive workout conducted on the same data, with their corresponding accelerometer readings to the right. As shown in FIG. 8B at top left, center left, and bottom left, the heart rate signals for all three runs, are again similar but not identical. In the first half of the run, it can be seen that the highest heart-rate rise response occurs in the data set shown in FIG. 8B, top left, followed by the data set shown in FIG. 8B, center left, and concluding with the data set shown in FIG. 8B, bottom left.

A number of reference points are marked in the heart rate traces of FIG. 8B, where the X values is the time value (in seconds) and Y value the subject's heart rate. Numerically, as shown in FIG. 8B, the heart rate rise starting at 10 seconds after the beginning of the run and ending 15 seconds later could be computed as follows: top left data set=25 bpm (from 62 bpm at 130 s to 87 bpm at 145 s), center left data set=15 bpm (from 68 bpm at 485 s to 83 bpm at 500 s), and bottom left data set=8 bpm (from 77 bpm at 840 s to 85 bpm at 855 s). Correspondingly, it can be seen that the accelerometer data sets vary from most intense, to least intense as shown in FIG. 8B, from top right to bottom right, during the respective time periods.

In the second half of the run, it can be seen that the lowest heart-rate rise response occurs in the data set shown in FIG. 8B, top left, followed by the data set shown in FIG. 8B, bottom left, and concluding with the data set shown in FIG. 8B, center left. Numerically, the heart rate rise ending at 10 s before the end of the run, and starting 15 s earlier, could be computed as follows: top left data set=2 bpm (from 100 bpm at 180 s to 102 bpm at 195 s), center left data set=5 bpm (from 104 bpm at 535 s to 109 bpm at 550 s) and bottom left data set=3 bpm (from 105 bpm at 890 s to 108 bpm at 905 s). Correspondingly, it can be seen that the accelerometer data sets vary from least intense as shown in FIG. 8B from top right, to medium intense as shown in FIG. 8B on bottom right, to most intense as shown in FIG. 8B center right, during the respective time periods. The exertion data monitored via an accelerometer residing on a treadmill demonstrates the feasibility of the embodiments presented here to provide a high-resolution capability to correlate physiological response, as represented by the heart rate signal, to a subject's level of exertion.

The correlations presented in FIGS. 6A-6C, 7A-7D, and 8A-8B of accelerometer signal strength to heart rate illustrate the concepts presented in this disclosure. A variety of analytical techniques including statistical signal analysis as well as machine learning techniques, among others, could be used independently or jointly to correlate the level of effort during the performance of a physical activity or exercise with the corresponding subject's physiological response, such as the heart rate signal. Further, this disclosure introduces the concept of an exertion monitor, whereby a physical activity sensor, such as an IMU, is used in combination with these techniques to establish the correlation between a subject's level of effort and the corresponding physiological response. This concept is further developed in the following.

In other aspects, the systems presented here can also provide the capability to collect an initial stream of physiological data from the subject during a range of physical exertion activities that are representative of the events intended to be monitored with the proposed system and method. The system disclosed is equipped with a multi-modal heart rate monitoring capability. Depending on the embodiment, the system may include, for example, the use of wireless channels across 2.4G digital Bluetooth Low Energy (BLE) and ANT+ for wireless/wired devices, be equipped to receive heart rate signals from standard 5 kHz analog chest straps, and/or be able to receive on-demand, ECG-based contact heart rate signals. Thus, embodiments of the systems presented here can have a complete range of data acquisition capabilities providing the ability to serve a plurality of applications. This allows for the system to develop a physiological response model commensurate with a representative exertion protocol.

To create a physiological model, the physiological response to a given level of exertion is characterized based on data received from one or more physiological response (e.g., heart rate) monitors. The physiological response of the heart rhythm to an increase in a physical activity or exercise also tends to increase, following a particular trajectory that is related to two parameters. The resting heart rate of a subject, which represents the typical minimum value of the heart rhythm that a subject would experience while awake, and the maximum heart rate value, which is typically roughly estimated based on the subject's age. Whether a moderate-intensity physical activity or a vigorous-intensity physical activity is carried-out, the heart rate will increase more rapidly the closer the subject's initial heart rate is to the subject's resting heart rate, and it will increase less rapidly the closer the subject's initial heart rate is to the subject's maximal heart rate. During a physical activity at a given intensity, the heart rate trajectory will thus typically increase faster at the beginning of the activity. As the activity progresses, the level of increase in the trajectory will slow down, with further increases tending to reach a plateau value. This value will depend on the activity intensity, as perceived and experienced by the subject.

Thus, the trajectory can be mathematically modeled with various curve fitting methods, which will provide various levels of fitting quality. The methods could be based on polynomials of the form:

$$y=a_0+a_1*x+a_2*x^2+a_3*x^3+\ldots+a_N*x^N,$$

including a cubic spline interpolation variant; exponential fit of the form:

$$y=a_0*e(a_1*x);$$

logarithmic fit of the form:

$$y=a_0+a_1*\log(x);$$

power fit of the form:

$$y=a_0*x(a_1);$$

among others, where $a_0, a_1, \ldots$ are fitting parameters.

The model of the physiological response to a physical activity at a given intensity is thus expected to be somewhat similar for most individuals and, in particular, a general model could be construed for classes of individuals, with cohorts that could be related by age, athletic capabilities, cardiovascular fitness levels, and so on. Models, such as those described here, that are tuned or specifically created for a given individual, however, would naturally yield higher accuracy. Even for a single individual, the parameters of such a model would vary to some smaller or larger degree, depending on the state of equilibrium of the subject's body, state of readiness, and many other factors as described earlier. Once created, these models can be saved in a database for later access and enhancement. Thus, the continual updating or calibrating of these models would further support higher levels of accuracy. The mathematical models based on a plurality of methods, such as the ones highlighted above, are a component of the methodology of many of the embodiments presented in this disclosure.

In addition to using a combination of various mathematically-based physiological models, embodiments can also use machine learning techniques. These techniques can be used to create and train models to predict the physiological response to a given type and level of exertion. Regardless of the mathematical models, machine learning models and other analytical and statistical tools used, and given the availability of one or more existing models in the associated database, the system may, by virtue of analyzing exertion and corresponding physiological response data, be able to automatically identify, as well as authenticate, both the type of equipment or exercise setting, where the subject is conducting a physical activity or exercise, and the subject. Multiple data records created from the user on the given equipment or exercise setting can also be used to enable the system to track the user and the equipment over time and produce algorithmic outputs that can provide valuable information on the physiological adaptation to a given exertion protocol. Algorithmic outputs are reflective of, for example, an increased performance with time due to training routines, decreased or increased state of readiness as ascertained by an evolving historical profile created in the database, as well as other valuable physiological response parameters. These outputs could then be correlated with the specific historic exertion data and associated physiological response.

Embodiments described here present an exertion-physiological (EP) engine in support of the creation of an exertion monitor and the development and deployment of combined exertion-physiological models. The exertion-physiological engine enables the system to monitor the subject's level of exertion and corresponding physiological response, such as heart rate, associated with an exertion protocol. A method for the creation of an exertion protocol using the EP engine is shown in FIG. 9A.

Figure 9A:
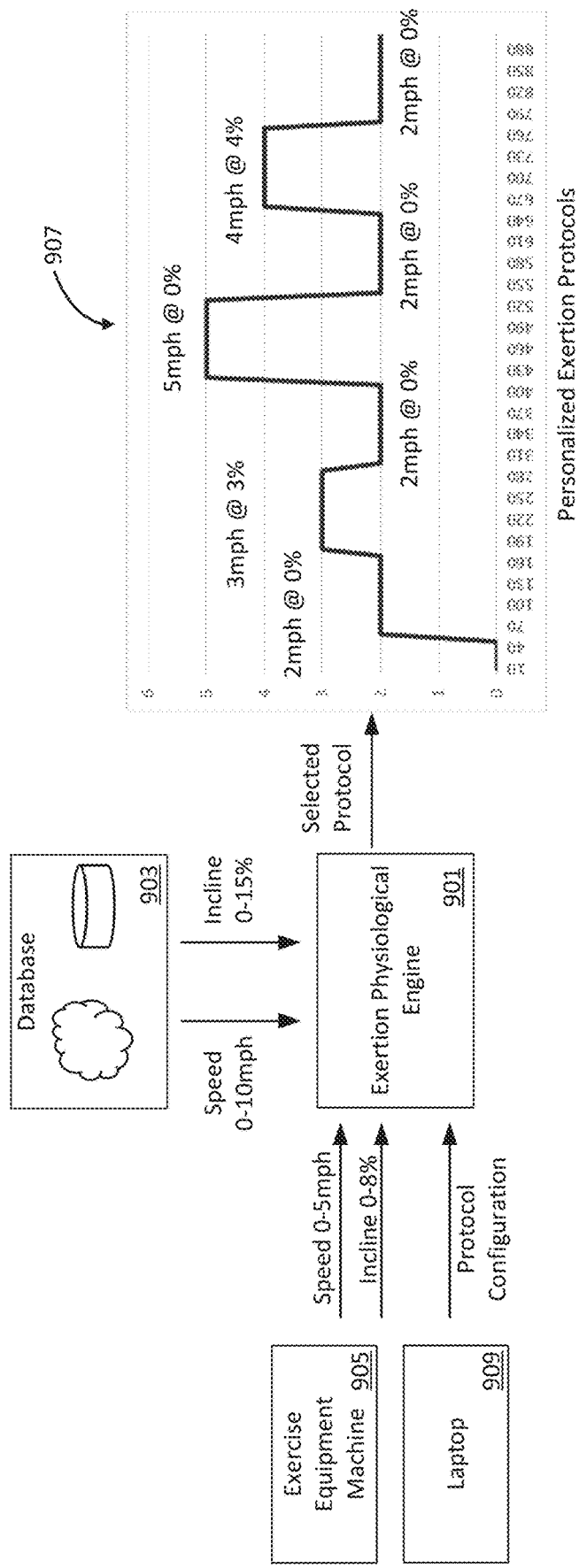
FIG. 9A is a schematic representation of a method for the creation of an exertion protocol using an exertion-physiological engine.

FIG. 9A is a schematic representation of a method for the creation of an exertion protocol using the EP engine. The exertion protocol of this embodiment is based on two components. Firstly, the intrinsic characteristics of the fitness equipment, such as a treadmill in this example, or alternative exercise setting that will be used to deploy the model. This information can be included either by entering the specification through a user interface of the exercise equipment machine 905, from a laptop 909, or by accessing the specification from a database 903, such as an available cloud or local database, based on the brand and model of the fitness equipment. In the case of a treadmill, for example, the maximum speed and maximum incline would be entered, or downloaded from an available database to the one or more processing circuits of the EP engine 901. The EP engine 901 can include one or more processors, including CPUs, GPUs, and other types of processing units, FPGAs, ASICs, integrated circuits, or other types of circuits to perform the processes described both above and in the subsequent discussion and perform these in hardware, software, firmware, or various combinations of these.

A second component is the subject's intended use of the equipment. This information is gathered by an interactive protocol configurator integrated into the EP engine 901. The configurator can be preloaded with standard protocols for a variety of supported types of fitness equipment. Once the specific parameters such as maximum speed and incline are entered, as in the case of a treadmill, such as from a range of 0-10 mph and 0-15%, respectively, the user would enter the specific personalized maximum speed and incline values for these parameters, such as from 0-5 mph and 0-8%, respectively. These personalized values may be updated at any time.

The EP engine 901 can then autogenerate a number of applicable protocols that will enable the exertion model to be created. The protocols are then made available to the user, who would then select and configure these protocols, such as the example shown at 907, based on the intended use of the fitness equipment, where every protocol step will include a duration, speed and incline within the preset limits, as well an initial warm-up period, optional cool-down periods during the protocol and an ending cool-down period. In some embodiments, an option to create smart protocols can also be available, wherein the created protocols, such as generated by algorithmic means or by using machine learning techniques, would yield protocols that are optimized to minimize the amount of time and data needed during a calibration routine, to obtain highly accurate models for the subject and the intended use of the machine.

In an example of a simple sequence of steps configured in a selected protocol 907, the protocol may start with a 2 mph, 2 minute warm-up period with incline level at 0%, followed by a 2 minute period with a light increase in speed to 3 mph with incline level at 3%, followed by a first 2 mph, 2 minute cool-down period with incline level at 0%, followed by a 2 minute period with a higher increase in speed to 5 mph with incline level at 0%, followed by a second 2 mph, 2 minute cool-down period with incline level at 0%, followed by a 2 minute period with a medium increase in speed to 4 mph and an incline of 4%, and completing with a final 2 mph, 2 minute cool-down period with incline level at 0%.

The embodiments presented so far use a method of monitoring physical exertion by using one or more signals obtained from an IMU located in a human wearable device or in a machine wearable device directly on a fitness equipment, which is mechanically coupled with a subject carrying out an exertion protocol. These monitors, based on using an IMU, can be referred to as mechanical exertion monitors. Other methods of monitoring physical exertion could be obtained by tracking the motion of the subject by monitors external to the subject and the exercise equipment, such as by using optical tracking monitors and using the EP engine to correlate the effort needed to move the subject's body based on the mass of the body, along with any additional weights or loads on the body, if any, and the acceleration imposed by conducting the specific physical activity or exercise being monitored. These systems can be referred to as optical exertion monitors. Yet other methods could include acoustic exertion monitors, similarly based on acoustic tracking systems, radio frequency exertion monitors, based on radio frequency motion tracking systems, or exertion monitors based on yet other tracking systems.

Yet other methods of monitoring physical exertion could include a combination of multiple monitors using the same modality. For instance, a multiplicity of IMU sensors could be placed on a single location or distributed across an exercise setting, such as on the treadmill used as one exemplary embodiment in this disclosure. Multiple co-located or distributed IMUs, for example, could then result in more robust and higher accuracy systems, also enabling corresponding higher fidelity model development. Yet other methods of monitoring physical exertion could include a combination of multiple monitors using multiple modalities; for instance, a multiplicity of exertion monitors operating based on tracking a subject with an optical tracking system, along with a mechanical system, could also result in a system and method with increased robustness and accuracy.

Further methods of monitoring physical exertion could include a combination of multiple monitors using multiple remote modalities. For instance, a multiplicity of exertion monitors could operate based on tracking a subject with an optical tracking system, along with an acoustic system or a radio frequency system. These monitors could be used remotely and may not require to be placed on a specific fitness equipment, or in the immediate location where the subject is conducting the physical activity or exercise. These systems and corresponding methods would also benefit from increased robustness and accuracy.

Yet other methods of monitoring physical exertion could include the use of any of the methods described above while additionally obtaining one or more metrics directly from the exercise setting itself. In the example of a treadmill, metrics such as speed and incline are typically computed and reported by the equipment manufacturers. In the example of a stationary/spin bike, these metrics can include cadence and power levels. Providing real-time feedback of this information into the EP engine could also be used to further enhance model development robustness. Metrics from exercise settings, if available, could be used by the EP engine. Clearly other combinations using any of these systems individually or combining a plurality of these systems or other systems that are able to monitor the subject's exertion could be used in the embodiments described herein.

The techniques described above provide for the creation of a personalized physiological model based on heart rate, given at least one or more configurable protocols that are created based on a specific exertion routine such as running on a treadmill, according with the specific personal exercise goals of a subject. The presented system can thus be designed to collect an initial stream of physiological data from a subject during a range of intended physical exertion activities according to the embodiment. In the following section, a methodology is presented to have the EP engine operate alongside a primary heart rate monitor for the creation and calibration of an exertion-physiological model during both a prescribed protocol and an unprescribed protocol scenario, in an implementation referred to as a "current-beat", or CB, modality. In a further methodology, the EP engine can operate alongside a primary heart rate monitor, available on-demand during an unprescribed protocol in an implementation referred to as a "next-beat", or NB, modality, where heart rate is predicted, in real-time, by the EP engine under a prescribed framework.

Figure 9B:
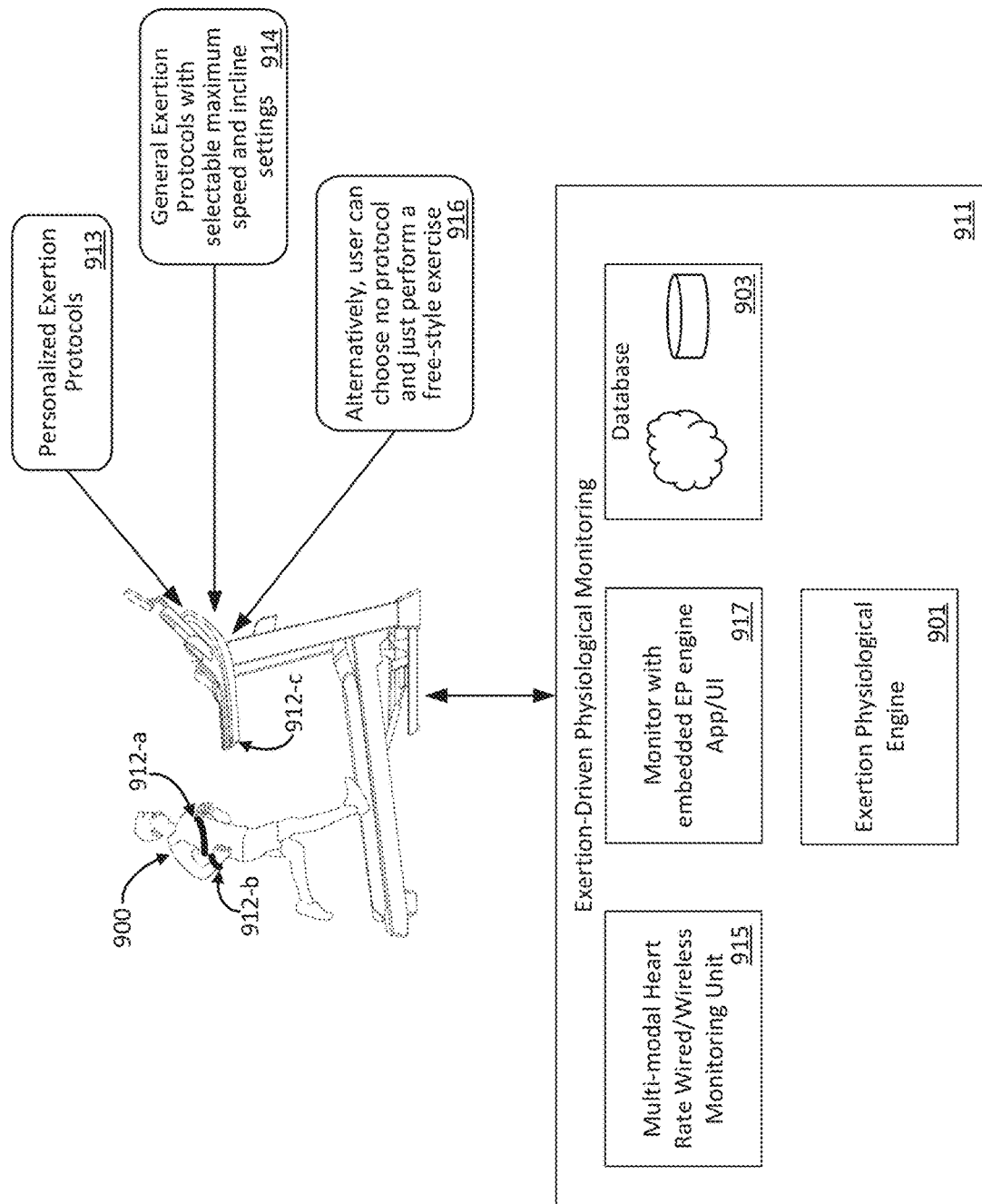
FIG. 9B shows an exemplary architecture of an exertion-driven physiological monitoring system based on the exertion-physiological engine.

FIG. 9B shows an exemplary architecture of an exertion-driven physiological monitoring system 911 based on the described EP engine 901. The system is shown using the current-beat modality with prescribed protocols to illustrate the creation/calibration routines. During this process, the subject 900 selects one of the one or more preconfigured exertion protocols 913 as described earlier. (914 and 916 will be discussed below with respect to embodiments for the EP engine with unprescribed or no protocols.) Once the protocol is selected, the user can choose a monitor with an embedded EP engine application or user interface 917 from one of various heart rate monitors operating in continuous mode such as by means of a chest strap 912a, an optical heart rate monitoring (OHRM) wearable 912b, or optionally, a contact heart monitor 912c while requiring the subject 900 to maintain contact during the entire protocol. The collected exertion-physiological data sets from the multi-modal heart rate monitoring unit 915 can then be used to create one of a plurality of personalized exertion protocol models for the subject. These models encompass a variety of possible exertion loads and corresponding physiological response outcomes for the subject on the selected fitness equipment.

Figure 9C:
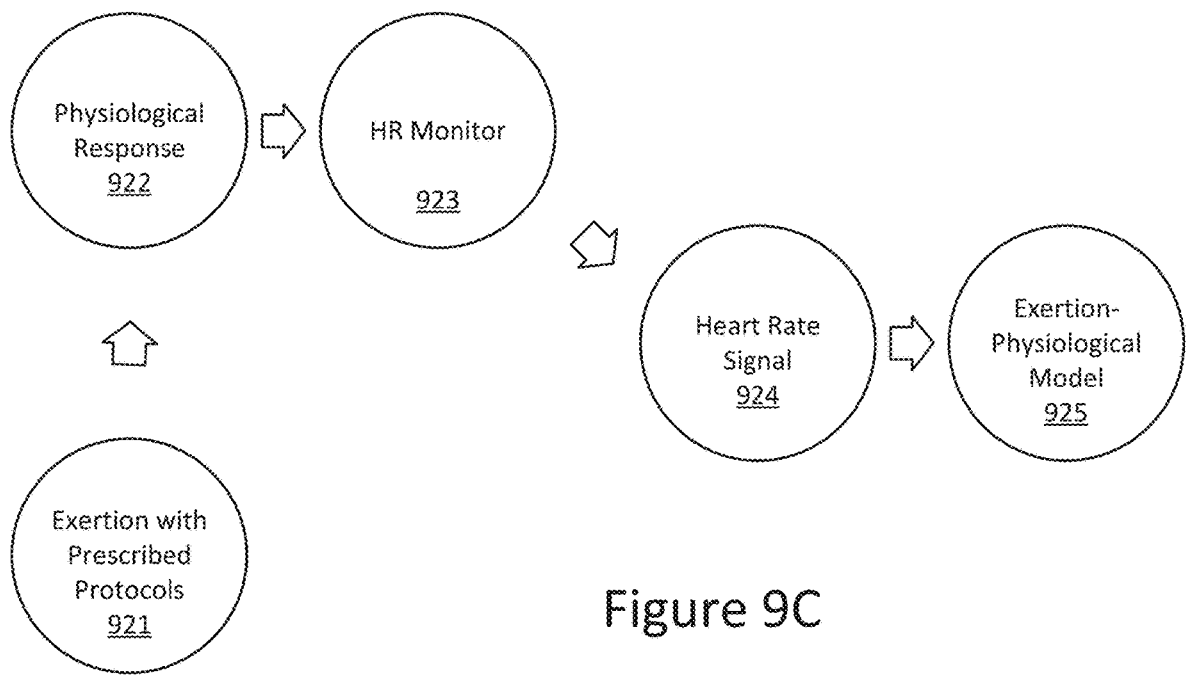
FIG. 9C presents a simplified description of an embodiment of a conceptual method for creating/calibrating models employing the exertion-driven physiological monitoring system in the current-beat modality using prescribed protocols.

FIG. 9C presents a simplified description of an embodiment of a conceptual method for creating/calibrating models employing the exertion-driven physiological monitoring system in the current-beat modality using prescribed protocols. Beginning at 921, the subject performs exertion corresponding with a prescribed protocol, generating the physical response of 922. The heart rate monitor or, more generally, one or more physiological response monitors (912a, 912b, or 912c, for example) determine the physiological response at 923 and provide a heart rate signal at step 924. The heart rate signal is then received at 925 by the exertion-physiological model for the creation and/or calibration of models for the subject. In some embodiments additional occasional protocol calibrations can be used as they may help tune existing models to variations that can occur in the subject or in the fitness equipment. Such variations may arise when the state of the subject has changed, such as when the subject's physiological response is improved due to training or diminished due to over-exertion, or when the fitness equipment, such as the treadmill in this example, is moved from a non-padded surface to a padded one, or vice versa, which could possibly impact the exertion motion signal.

Figure 9F:
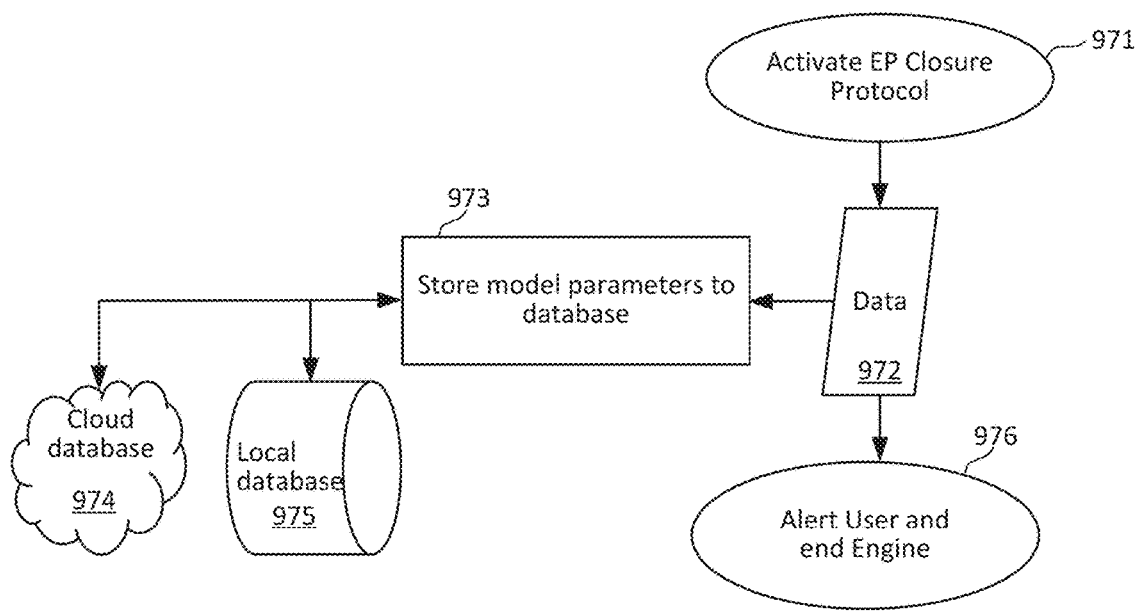
FIG. 9F presents one embodiment for a flow of a closure methodology process, which includes saving the exertion-physiological response data streams along with model parameters to the cloud or local database for later access.
Figure 9D:
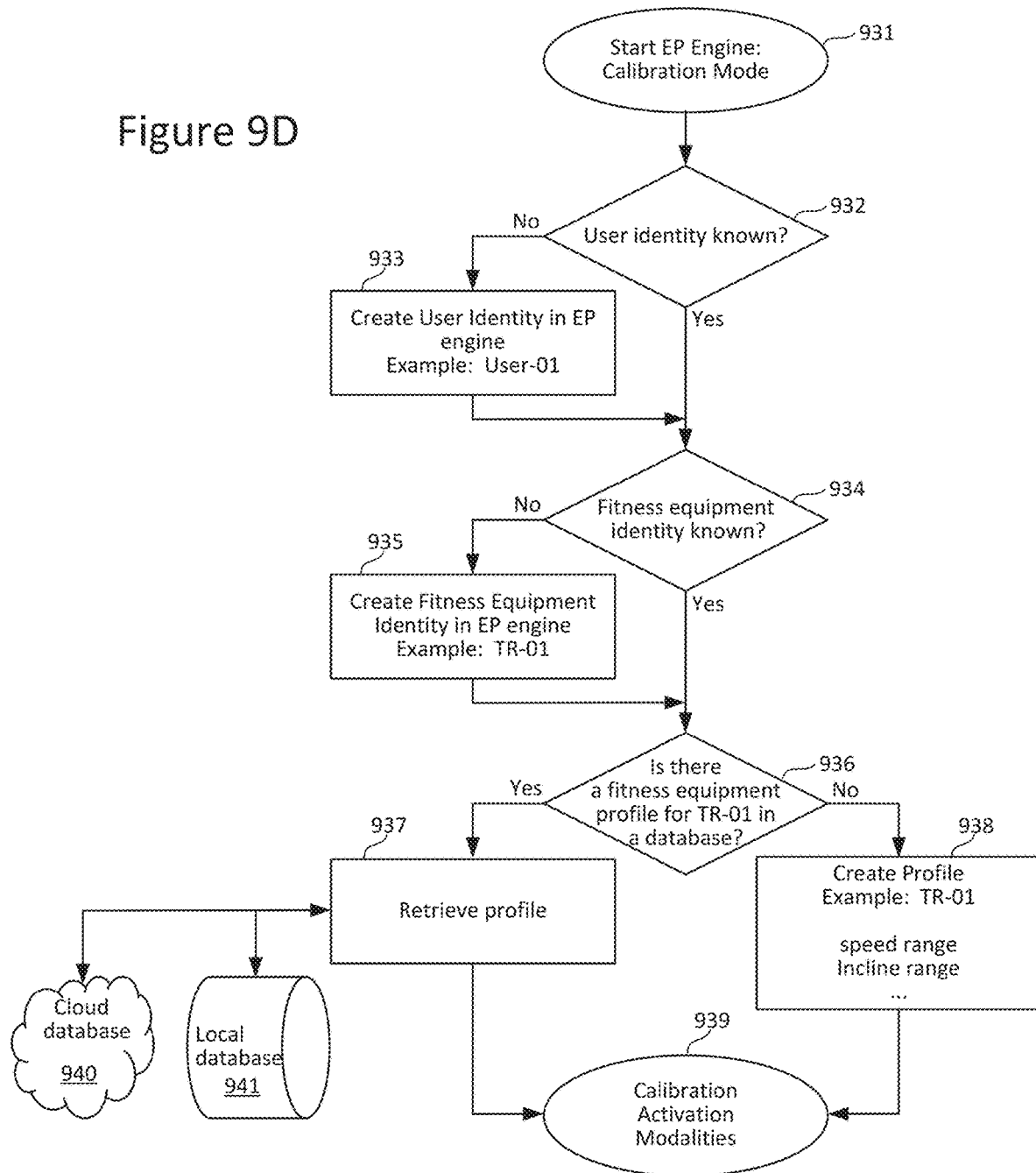
FIG. 9D illustrates an embodiment for the initialization methodology for the exertion-physiological (EP) engine while conducting a calibration routine.
Figure 9E:
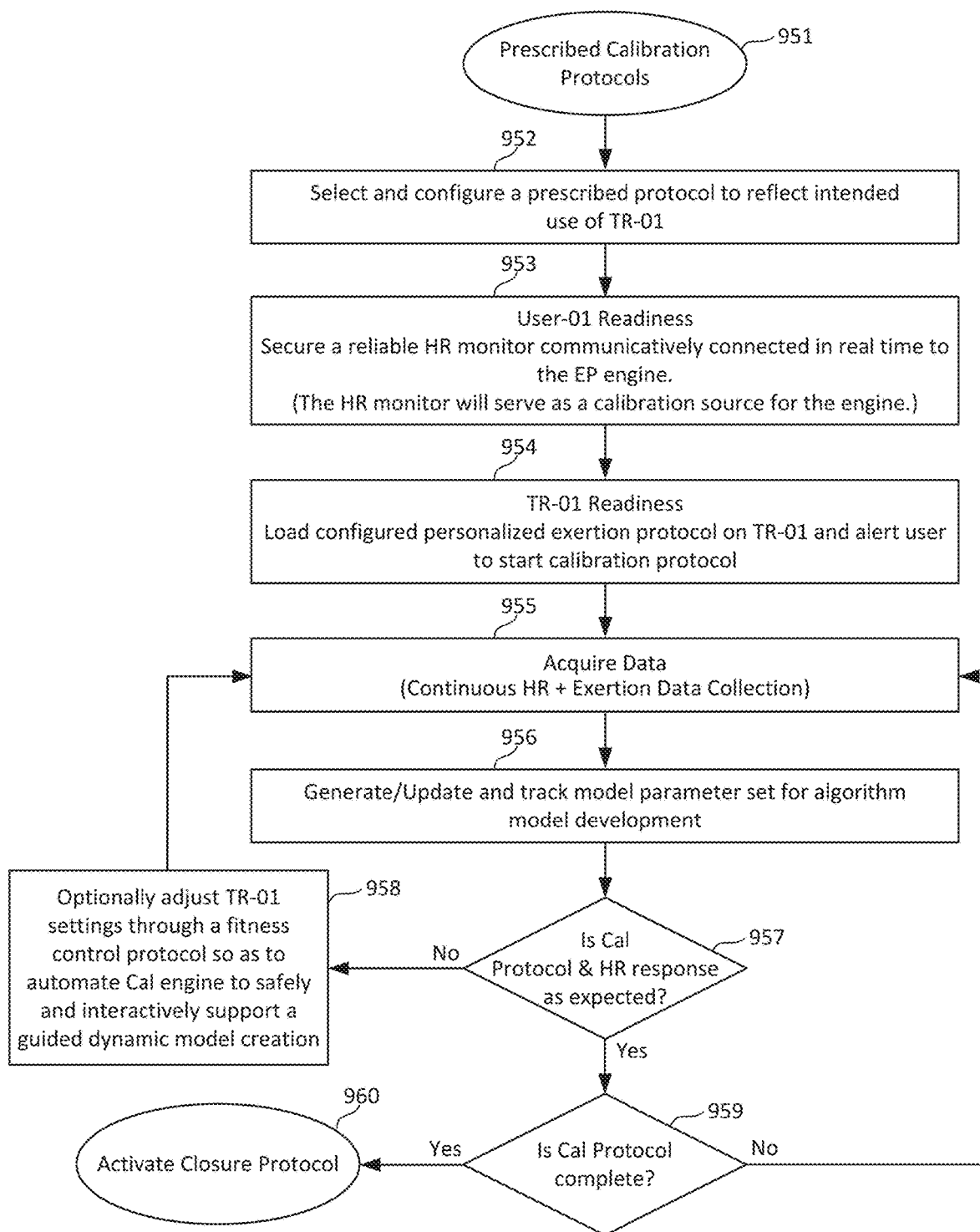
FIG. 9E is a flow for one embodiment of a more detailed operation methodology for creating/calibrating models employing the exertion-driven physiological monitoring system with prescribed protocols.

FIGS. 9D-9F are flows presenting a more detailed conceptual method of embodiments for creating/calibrating models employing the exertion-driven physiological monitoring system in the current-beat modality using prescribed protocols. Starting at 931, FIG. 9D illustrates an embodiment for the initialization methodology for the EP engine while conducting a calibration routine. At step 932 the EP engine flow determines whether the user identity is known to secure the user identity and, if so (Yes path), user information can be retrieved before the flow goes to step 934; and if the user identity is not known (No path), the flow goes to step 933 to create a user identity (such as User-01) before going on to step 934.

In the flow of FIG. 9D, the system secures or verifies the creation of a fitness equipment identity in the system. Step 934 determines whether the identity of the fitness equipment is known: if so, the flow continues on to step 936; and, if not, step 935 creates a profile for the fitness equipment identity in the system, such as TR-01, in the exemplary case of the fitness equipment being a treadmill before continuing to step 936. It should be noted that alternate embodiments could use different orders for the process of FIG. 9D, such as swapping the order of user identity (step 932 and related steps) and fitness equipment identity (step 934 and related steps), for example.

Step 936 determines whether there is a corresponding profile for the fitness equipment (TR-01 in the example) and, if so, procures the profile at step 937; and, if not, at step 938 guides the user in the creation of the profile for the equipment, which will specify the range of values for the operating parameters for the equipment. The parameters may be available from a database in the cloud 940 or from a local database 941, or can be entered into the system prior to conducting the calibration. In the case of a treadmill, for example, these parameters include the speed and incline settings for the system. Once the initialization is complete, the engine will guide the user to continue 939 with the specific calibration methodology the user would like to pursue. The first calibration option includes the ability for the subject to configure prescribed calibration protocols.

FIG. 9E is a flow for one embodiment of a more detailed operation methodology for creating/calibrating models employing the exertion-driven physiological monitoring system with prescribed protocols, starting at 951. The system can use the exertion protocol configurator to guide the user in the creation of a personalized exertion protocol. In this approach, the user is presented with a selection of one or more protocol templates that may be available in the EP engine at step 952. The user can then configure a selected protocol, including the number of steps and step duration. The selected protocol can operate within personalized preset limits as a subset of the fitness equipment operating parameters, such as the overall maximum speed and incline in the case of a treadmill. Further limits on combined parameters, such as specifying the use of lower incline settings for higher speeds, or lower speeds for higher incline settings, can also be configured during this process.

At step 953 the EP engine guides the user to securing a reliable, continuous heart rate monitor communicatively connected to the engine prior to beginning the exertion protocol. This physiological response monitor will serve as the calibration source for the process of creating the exertion-physiological model. This step is to ensure User-01 readiness. At step 954 the system then loads the exertion protocol and alerts the user that the system is ready to start the calibration protocol. Step 954 is to ensure TR-01 readiness and provide a start alert to the user.

The EP engine will then guide the user to commence the calibration process and gather the exertion data along with the physiological signal data at step 955. During this process, the EP engine will compute, in real time, key parameters for the creation of the algorithmic development of the exertion-physiological model at step 956. The system will continue by validating the physiological data collected during the deployment of the protocol to see it complete safely, looping back to the data acquisition of step 955. Within the loop, a step 957 can determine whether the heart rate is as expected, and step 959 determines whether the protocol has completed. Optionally, if enabled, the system may interact with the protocol to, for instance, alert the user to safely terminate the protocol if the user monitored response is not as expected at step 957. This could be a result of not receiving a reliable heart rate signal. Additionally, at step 958 a capability can also be made optionally available where the system can adjust TR-01 settings through a fitness control protocol so as to automate the EP Engine to safely and interactively support the deployment of a guided dynamic model creation. Once the calibration protocol is completed (Yes path from step 959), the system will proceed to activate the closure of the calibration process at 960.

FIG. 9F shows one embodiment for a flow of a closure methodology process, which includes saving the exertion-physiological response data streams along with model parameters to the cloud or local database for later access. Protocol closure is activated at 971, providing the exertion-physiological response data streams 972 generated during the subject's execution of the protocol. At step 973 the system stores the model parameters to a database, where this can include a local database 975, a cloud-based database 974, or some combination of these. The user is also alerted, and the EP engine's operation is ended at 976.

In an alternative set of embodiments, the user is enabled to utilize the EP engine without the creation of a prescribed protocol. In this mode, the EP engine will perform the calibration routine based on a general exertion protocol, or without the need for any protocol. These embodiments can again be illustrated with respect to FIG. 9B, which shows an exemplary architecture of an exertion-driven physiological monitoring system based on the proposed EP engine using the current-beat modality with unprescribed protocols to illustrate the creation/calibration routines. In this modality, the EP engine can use the contact heart rate monitor 912c, communicatively connected to the EP engine, as the calibration source for the process of creating the exertion-physiological model. In this embodiment, rather than use personalized exertion protocols 913, the system will instead load a general exertion protocol 914 and alert the user to select personalized maximum speed and incline settings applicable to the protocol. Alternately, the system also allows the user to select a free-style exercise 916 without imposing the use of a protocol. The exertion-driven physiological monitoring system thus offers the flexibility to create an exertion-physiological model without the requirement of using a prescribed protocol during the calibration routine. While developing a model might take longer using this method, this approach offers the advantage of being available for first-time users, as well as for occasional or frequent users without the requirement to perform a formal calibration routine.

Figure 10A:
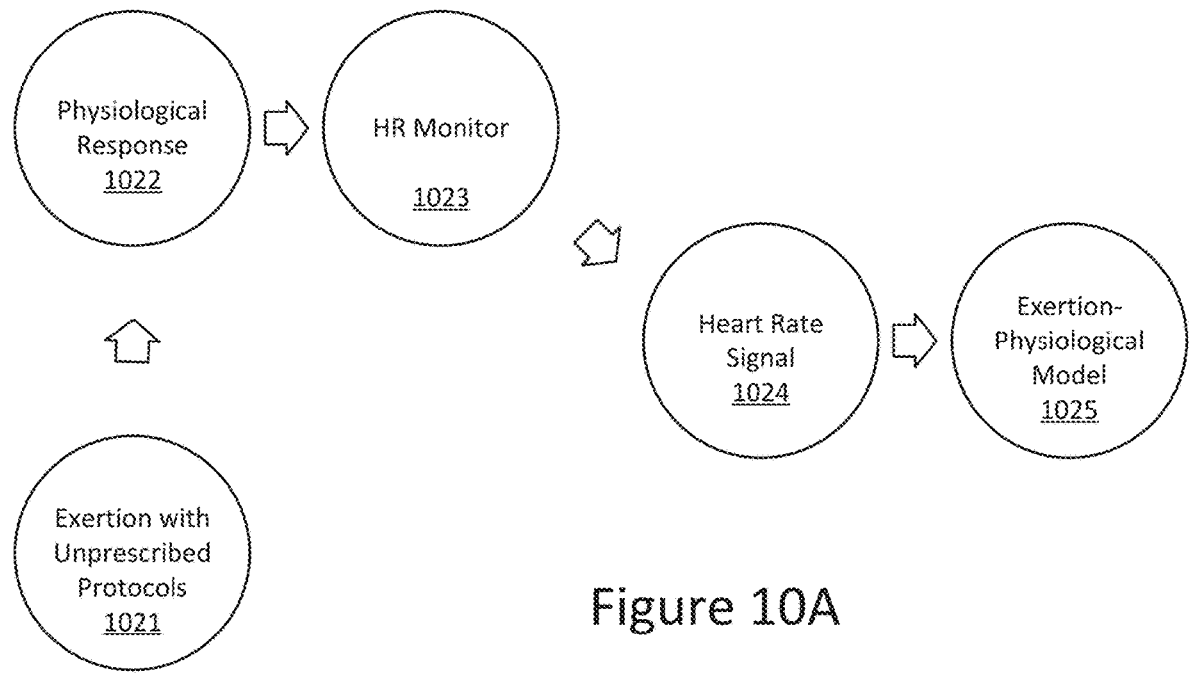
FIG. 10A shows a simplified conceptual method of creating/calibrating models employing the exertion-driven physiological monitoring system in the current-beat modality using unprescribed protocols or a protocol-free calibration process without the requiring the use of any protocol.

FIG. 10A shows a simplified conceptual method of creating/calibrating models employing the exertion-driven physiological monitoring system in the current-beat modality using unprescribed protocols or a protocol-free calibration process without the requiring the use of any protocol. FIG. 10A is arranged similarly to FIG. 9C, except that, beginning at 1021, the exertion-physiological model is created based on the data collected during the time periods when the contact heart rate monitor is in use, rather than using prescribed protocols as in 921 of FIG. 9C.

More specifically, beginning at 1021, the subject performs exertion corresponding with unprescribed protocols, generating the physical response of 1022. In the embodiment described here, the contact heart rate monitor 912c determines the physiological response at 1023 and provides this as a heart rate signal 1024. The heart rate signal is then received at 1025 by the exertion-physiological model for the creation and/or calibration of models for the subject based on the data collected during the time periods when the contact heart rate monitor is in use.

We can look in more detail at the creation/calibration of models employing the exertion-driven physiological monitoring system in the current-beat modality using unprescribed or no protocols. The initialization methodology for the EP engine while conducting a calibration routine can be performed in a similar fashion to the methodology used for the current-beat modality using prescribed protocols as described above with respect to FIG. 9D. As in that case, the system can first secure or verify the creation of both the user identity and the fitness equipment identity along with its corresponding operating parameters in the system, and then proceed to the calibration activation process.

Figure 10B:
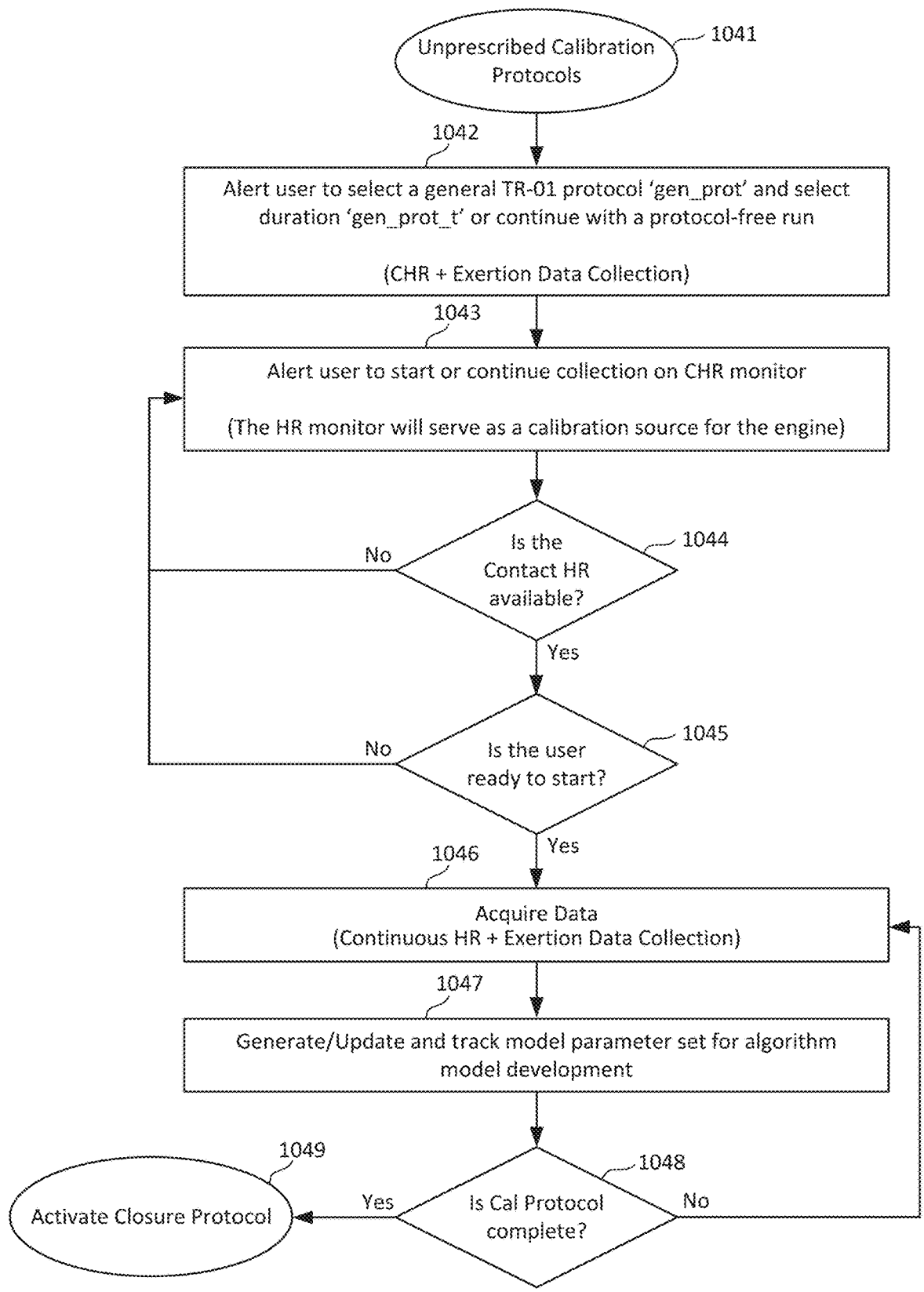
FIG. 10B shows the operation methodology of the EP engine using unprescribed or no protocols and corresponds to FIG. 9E for the prescribed protocol methodology.

FIG. 10B shows the operation methodology of the EP engine using unprescribed or no protocols and corresponds to FIG. 9E for the prescribed protocol methodology case. The unprescribed calibration protocol begins at 1041. In the unprescribed or no protocol modality, at 1042 the system will guide the user to select from one of one or more general protocols (gen_pro) for the exercise equipment (treadmill TR-01 again in this example) that are configured with selectable top speed and incline values, and designed to operate for a selectable time (gen_pro_t). The user can then customize those values and select the general protocol. Optionally, the user can also proceed with no protocol and instead perform a protocol-free exercise. The user is then alerted at step 1043 to start or continue collection of data on the contact heart rate (CHR) monitor, which serves as a calibration source for the EP engine. Step 1044 checks on whether the contact heart rate monitor is available and, if not, can continue to loop back until it is. If the contact heart rate monitor is available, step 1045 determines whether the user is ready to start, looping back to step 1043 to alert the user if not. If the user is ready, the flow moves on to step 1046 and the system will then continuously track the contact heart rate (CHR) monitor 912c, which will be communicatively connected with the EP engine.

Once a heart rate signal is detected, at step 1046 the EP engine will record both the exertion level of the user, alongside with the corresponding physiological response, for as long as the contact heart rate signal is present. During this process, the system can generate/update and track the model parameter set for algorithm model development at step 1047, with the flow looping back to step 1046 if step 1048 determines that the protocol is not completed. When the user stops holding onto the contact heart rate sensor, the engine can go back to step 1044 and wait until a new contact is made, if any, and heart rate signal is obtained again. This approach will be repeated throughout the workout session, and calibration routine updates will ensue. Future workouts in this machine will continue to feed into the model, enabling the exertion-physiological model to be continually updated. Once the calibration protocol is determined completed at step 1048, the system will proceed to activate the closure of the calibration process at 1049. The closure methodology process, which includes saving the exertion-physiological response data streams along with model parameters to the cloud or local database for later access, can be the same as described above with respect to FIG. 9F.

Once the creation/calibration protocol is complete, the system can process the calibration data and compute critical model parameters for the proper operation of the current-beat (CB) and next-beat (NB) modalities. In the CB modality, these parameters include the current-beat confidence-factor quality (CBQ), which correlates with the ability of the model to reproduce the expected value of the heart rate accurately during a subsequent protocol. The model can then be used by the EP engine to effectively synthesize a heart rate signal in real time, based on the exertion input. Thus, in the CB modality there is a concurrent operation of two heart rate monitors: The first one corresponds to the ECG-based contact heart rate monitor (or any other applicable source); and the second is the exertion-based synthetic heart rate monitor created by the EP engine, which is here denoted as "current-beat heart rate" (CB HR).

Figure 11A:
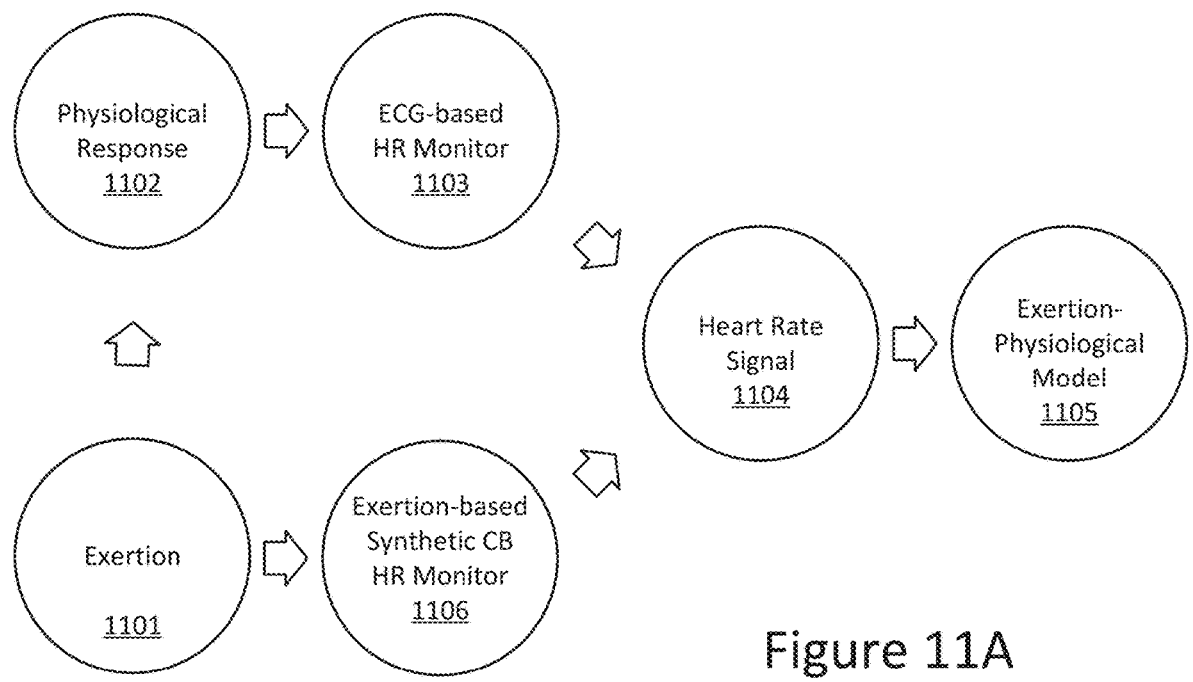
FIG. 11A illustrates a simplified view of an embodiment for the concurrent operation of the EP engine during the current-beat (CB) modality, where both an ECG-based heart rate monitor and an exertion-based synthetic heart rate monitor operate independently to generate a dual heart rate signal.

FIG. 11A illustrates a simplified view of an embodiment for the concurrent operation of the EP engine during the CB modality, where both an ECG-based heart rate monitor and an exertion-based synthetic heart rate monitor operate independently to generate a dual heart rate signal. FIG. 11A is presented similarly to FIGS. 9C and 10A for the creation/calibration protocols, except in addition to the exertion leading to a physiological response, it also is used to provide a synthetic current-beat heart rate monitor.

More specifically, beginning at 1101, the subject performs exertion generating the physical response of 1102. One or more physiological response monitors determine the physiological response at 1103 and provide a heart rate signal at 1104. The exertion level at 1101 is now also used by the exertion-based synthetic heart rate monitor at 1106, which also provides a synthetically generated heart rate signal at 1104. During the CB modality operation, the EP engine will compare both the ECG-based value of 1103 and the exertion-based value of 1106 for the heart rate signals and will compute a signal error. Concurrently, this error will be used as an additional input into the computation of the CBQ confidence factor. The heart rate signal from 1104 is then received at 1105 by the exertion-physiological model for the creation and/or calibration of models for the subject.

An EP engine algorithm can track the CBQ confidence factor, in real time, to achieve two separate goals. The first is to continually improve and update the model while this modality is in use. The second is to enable the model to optionally replace the actual monitored heart rate with the value predicted by the exertion monitor engine, provided that the confidence factor is high enough to take this action. Depending on the dynamic nature of the confidence factor, the heart rate value may optionally be selected between the contact heart rate monitor of 1103 and the exertion-based EP engine CB HR of 1106. This operation can use continuous heart rate acquisition using the contact heart rate monitor (or any other applicable source) along with the continuous CB HR prediction from the EP engine, as well as the dynamically computed CBQ confidence factor.

Figure 11B:
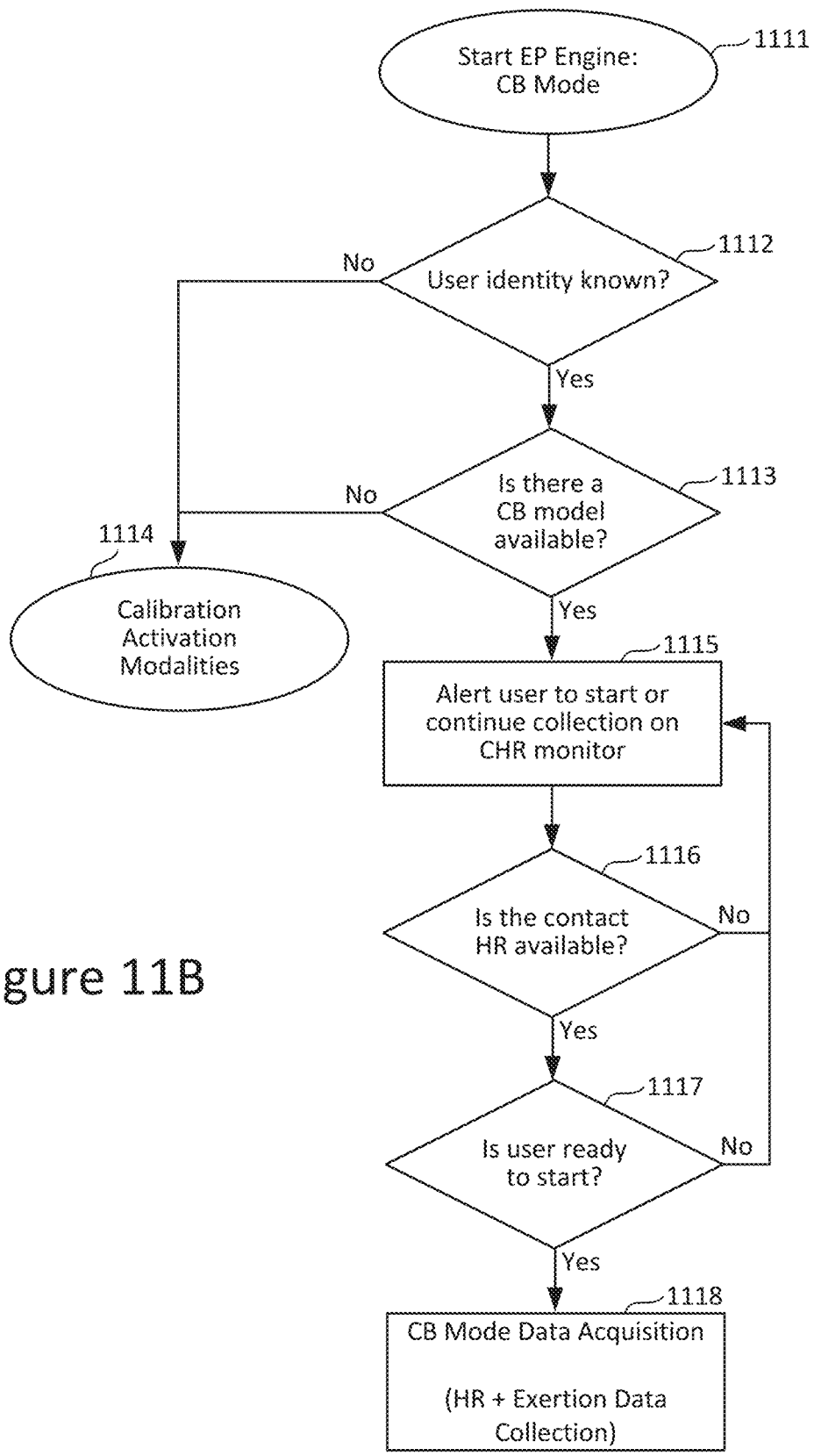
FIGS. 11B-11D present a detailed view for an embodiment of the conceptual method used by the exertion-driven physiological monitoring system to deploy the current-beat EP engine models.
Figure 11D:
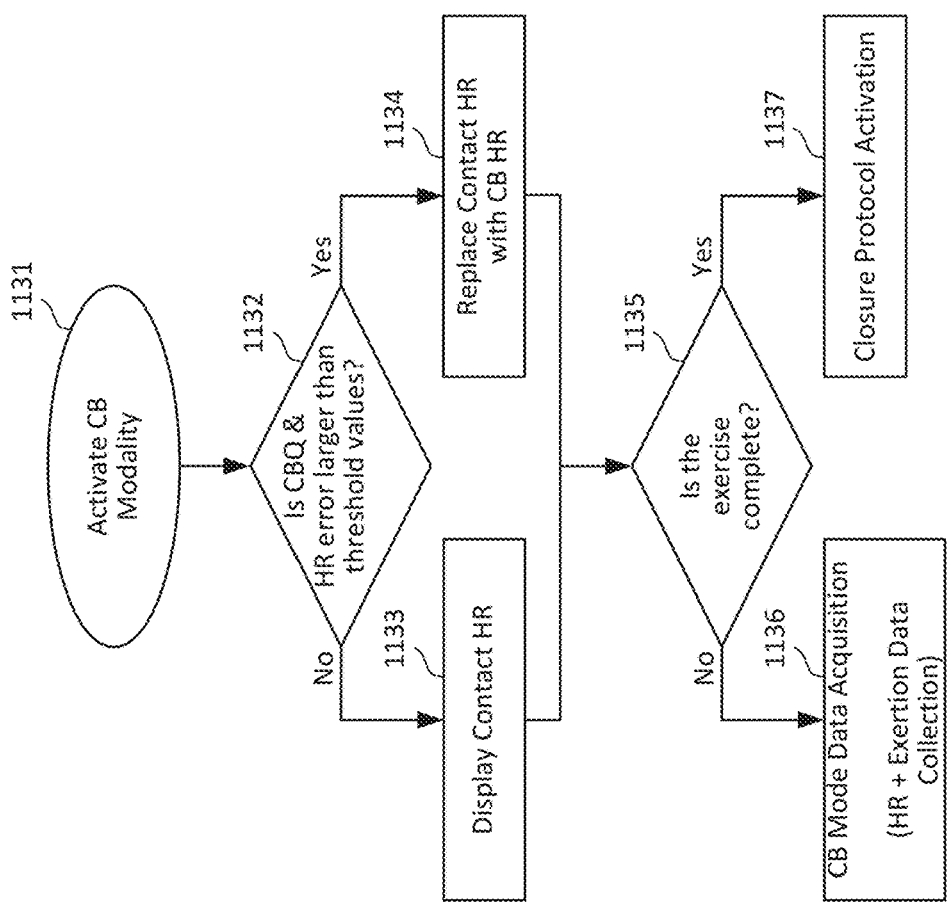
Figure 11C:
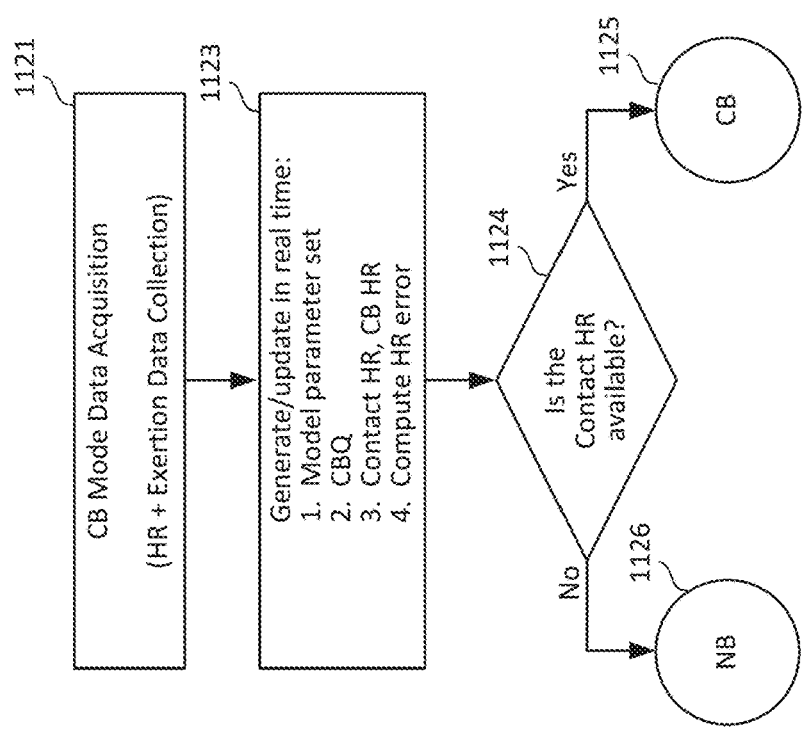

FIGS. 11B-11D present a detailed view for an embodiment of the conceptual method used by the exertion-driven physiological monitoring system to deploy the current-beat EP engine models. More specifically, FIG. 11B is a flowchart for an embodiment of the initialization methodology for the operation of the EP engine in the active CB modality, starting at 1111. In a similar fashion as to the methodology used for the creation of the calibration protocols (e.g., FIG. 9D), the system first verifies the user identity at step 1112 and inquires whether an exertion-physiological model (CB model) is available at step 1113, which is required to operate the system in the CB modality. If the user or associated CB model is not available, the EP engine redirects the user to proceed to the calibration process at 1114, so that a CB model may be created for the user. If a CB model is available, at step 1115 the system alerts the subject to use the contact heart rate monitor to provide an initial heart rate signal to the system and then proceed to start the operation of the system and commence acquiring data in the CB mode. Step 1116 determines whether a contact heart rate monitor is available and, if not, loops back to step 1115; if so, the flow goes to step 1117 to see whether the user is ready to start. If the user is not ready, the flow loops back to alert the user at step 1115. If the user is ready, the process can proceed to CB mode data acquisition at 1118.

FIG. 11C presents a flow chart for an embodiment of the next step in the process, the selection of an operational modality, which starts with the "CB mode Data Acquisition" step 1121. As the system gathers data from the exertion monitors and physiological response monitors, at step 1123 the EP engine will then compute a number of parameters from this data to support the algorithmic operation of the CB modality. It will also continue to compute and track, in real-time, the CBQ confidence factor. Additionally, it will compute the contact heart rate signal, as well as the synthetic CB HR signal. Step 1124 can again verify whether there is a contact heart signal available, and if so, it will proceed to activate the deployment of the CB modality at 1125. Otherwise, it will direct the EP engine to operate in the NB modality at 1126, which is described below beginning with FIG. 12A.

FIG. 11D illustrates an embodiment for the CB modality activation, starting at 1131. In this operation, the EP engine compares the confidence coefficient CBQ to a preset threshold value that has been algorithmically determined to ensure that for the current user and current activity, there is a high likelihood of computing, in real time, a synthetic CB HR with significant accuracy. The EP engine will ensure that during this operation, both the heart rate signal proceeding from the contact heart rate monitor (or other applicable monitor) and the CB HR signals are continuously available. The EP engine will then compute, also in real time, the relative error between both heart rate data streams (HR_error) at step 1132.

If CBQ is smaller than an appropriate preset value (No path from step 1132), it will be concluded that the heart rate generated by the contact heart rate monitor (or other applicable monitor) is more accurate. The only action taken would then be to display the contact heart rate at step 1133. If CBQ is larger than an appropriate preset value and the HR_error is smaller than a corresponding preset error threshold, it will be concluded that both heart rate signals are accurate. The only action taken would then be to continue to display the contact heart rate. If CBQ is larger than an appropriate preset value and the HR_error is also larger than a corresponding preset error threshold (Yes path from step 1132), however, it will be concluded that the heart rate generated by the EP engine model will be more accurate than the value obtained from the contact heart rate monitor, and the reported ECG-based heart rate could be optionally replaced with the synthetic CB HR data stream at 1134.

The EP engine operates in real time, and thus the assessment as to which heart rate source is more accurate will be re-evaluated continuously during the workout, where step 1135 monitors whether the exercise is complete. If not complete, CB mode data acquisition continues at step 1136. Once the exercise is completed, the EP engine proceeds to the closure of the protocol at 1137. The protocol closure activation process, which includes saving the exertion and corresponding physiological response data streams to the cloud or local database for later access, can be as described above with respect to the flow of FIG. 9F.

The presence of the combined exertion and corresponding physiological response data streams represents unique individual information about the user conducting the monitored physical activity and thus provides the opportunity to identify the subject being monitored. If the subject is identified, the EP engine will then jointly monitor these data streams and the CBQ confidence factor. If CBQ is larger than an appropriate preset value, the EP engine will confirm the identity of the user and proceed to authenticate it. While the motion data, as collected by any motion tracking system, inclusive of data collected with an IMU system, may yield patterns that may temporarily be unique to a subject under the conducting of a specific physical activity or exercise and thus could potentially be used as a user identification metric, the main embodiments presented here focus on the combined exertion and corresponding physiological response of the subject. Thus, the system identification is based on the functional dynamic nature of the individual's exertion load and corresponding physiological response. Conversely, while the heart rate data, as collected by any heart rate monitoring system, inclusive of data collected with ECG-based or PPG-based (or other) systems, may yield patterns that may temporarily be unique to a subject under the conducting of a specific physical activity or exercise and thus could potentially be used as a user identification metric, the embodiments presented here are based on the functional dynamic nature of the individual's exertion load and corresponding physiological response. Furthermore, the functional dynamic nature of the presented system identification aspect is applicable regardless of whether the data is collected with human wearables or machine wearables, as defined in this disclosure.

Figure 11E:
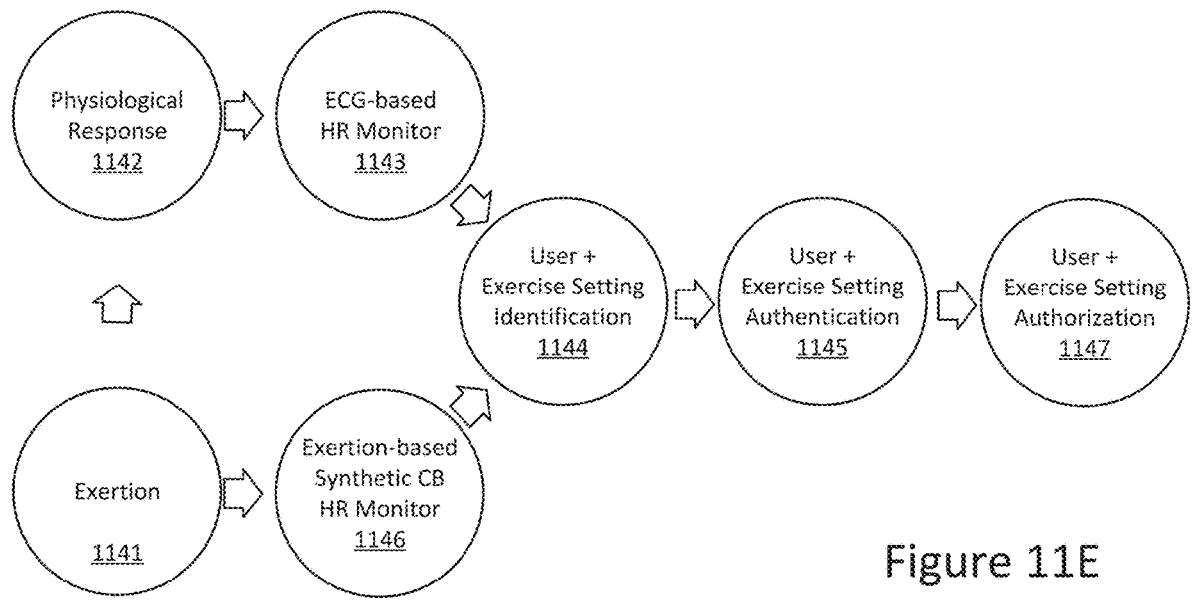
FIG. 11E presents a simplified view of the identification and authentication process and FIG. 11F presents a flowchart for one embodiment of the initialization of the CB Modality with an auto-identification feature in place.

FIG. 11E presents a simplified view of the identification and authentication process, whereby the combined data streams are used to first identify and then authenticate the user, provided the required value of CBQ is attained or exceeded. FIG. 11E is arranged similarly to FIG. 11A and 1141, 1142, 1143, and 1146 of FIG. 11E can respectively correspond to 1101, 1102, 1103, and 1106 of FIG. 11A. The physiological response monitor base data from 1143 and the exertion monitor based data 1146 are then combined at 1144 to perform user and exercise setting identification, which can then be used at 1145 for user and exercise setting authentication. Authentication is followed by user and exercise setting authorization at 1147, which can be a policy decision based on the identification of step 1144 and authentication of step 1145.

Figure 11F:
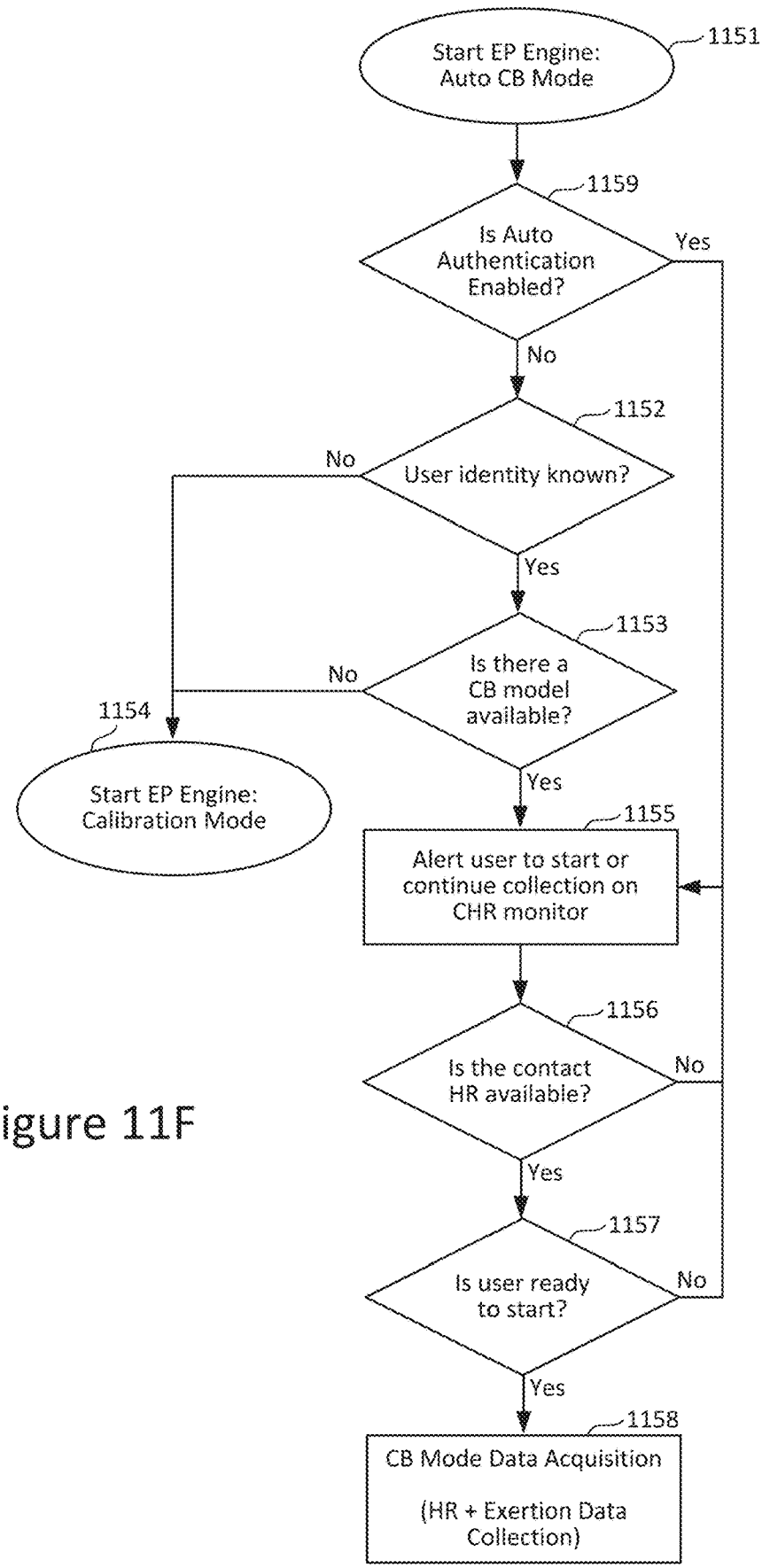

FIG. 11F presents a flowchart for one embodiment of the initialization of the CB Modality with an auto-identification feature in place. Starting the engine in the Auto CB Modality at 1151 enables the EP engine to automate the process of identification of both the user and the exercise setting. Thus, once the user commences the physical activity in the CB modality, and the "authentication feature" is enabled, the dual exertion/physiological data streams will be used to identify and authenticate both the exercise setting as well as the user, provided the required value of CBQ is attained or exceeded. Once the authentication is completed, the EP engine will associate the existing exertion-physiological model to the current exertion-setting/user pair. If the Auto CB modality 'authentication feature' is not enabled, the EP engine will operate in the manner described earlier in the standard CB Modality of FIG. 11B.

More specifically, relative to FIG. 11B, FIG. 11F includes an initial step 1159 for the determination of whether auto-authentication is enabled. If so, the flow goes to step 1155 to alert the user. If auto-authentication is not available, the flow can then instead go to step 1152. The other steps in FIG. 11F can then correspond to those of FIG. 11B, with steps 1152, 1153, 1154, 1155, 1156, 1157, and 1158 respectively corresponding to steps 1112, 1113, 1114, 1115, 1116, 1117, and 1118 as described above with respect to FIG. 11B.

The embodiments presented here thus offer a significant value for physical activities, such as highlighted with the exemplary exercise on a treadmill used to illustrate these concepts, including the ability to provide an alternative method to improve heart rate accuracy while actively gathering heart rate signal from an ECG-based contact heart rate monitor (or other applicable heart rate signal sources). It will also facilitate the operation of the system through the automated authentication feature.

An important parameter for the proper operation of the NB modality can include the next-beat confidence-factor quality NBQ, which correlates with the ability of the model to reproduce the expected value of the heart rate accurately during a subsequent protocol. The model is then used by the EP engine to effectively synthesize a heart rate signal in real time, based on the exertion input. An additional parameter of importance computed by the model is the expected length of time NBT, where NBQ is high-enough as to be able to predict the heart rate in the absence of an alternative heart rate monitoring source. This exertion-based, synthetic heart rate signal is here denoted as the "next-beat heart rate", or NB HR. The next-beat prediction engine can use a prescribed framework, whereby in addition to the existence of a CB model for the subject, an initial "current-beat" heart rate signal trajectory is tracked alongside with the subject's level of exertion, which is then used to build a next-beat model (NB model). The NB model will represent a more robust version of the CB model. Once the computed NBQ is deemed sufficiently high, the EP engine is armed and ready to operate in the NB modality autonomously.

In the example of a treadmill, a subject may hold onto the contact heart rate monitor until the EP engine operating in the NB modality is armed. Once the EP engine is armed, the subject is alerted. The subject may then release the grip. Upon releasing the grip, the exertion engine is triggered and the subject's heart rate can then be predicted by the engine for a length of time indicated by the computed NBT.

Figure 12A:
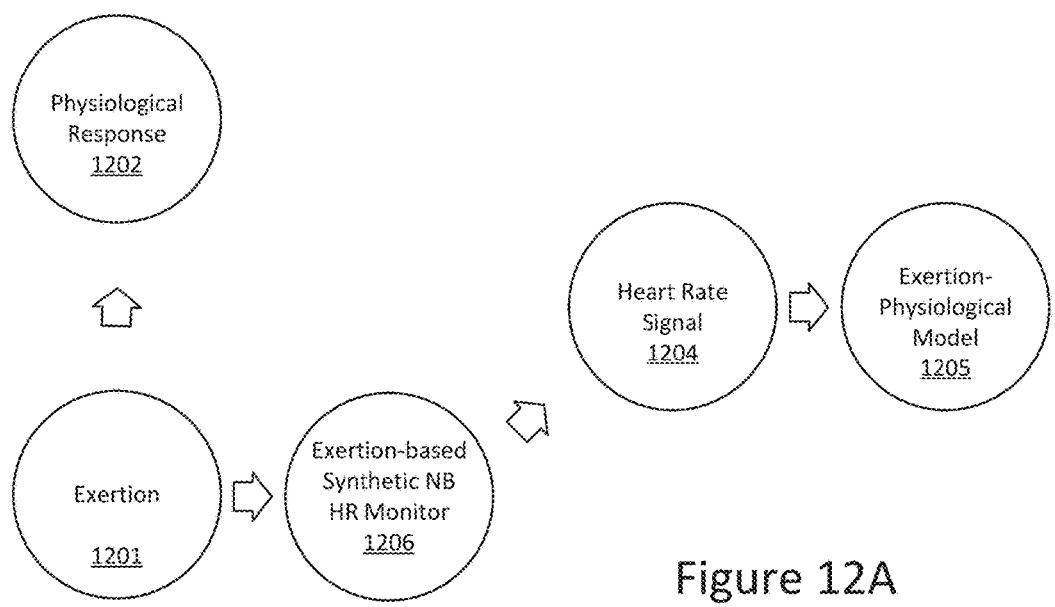
FIG. 12A illustrates a simplified view of the concurrent operation of the EP engine operating in the next-beat (NB) modality, where once triggered and for a period time given by the next-beat time window (NBT), the EP engine will autonomously generate a heart rate signal.

FIG. 12A illustrates a simplified view of the concurrent operation of the EP engine operating in the NB modality, where once triggered and for a period time given by NBT the EP engine will autonomously generate a heart rate signal. Relative to FIG. 11A, the subject's exertion at 1201 again produces both the physiological response of the subject at 1202 and also the exertion-based synthetic next-beat heart rate monitor determination at 1206. Unlike in FIG. 11A, only the exertion-based synthetic data from 1206 is used to generate a heart rate signal at 1204; and thus, FIG. 12A lacks the equivalent of 1103 from FIG. 11A. The heart rate signal generated in 1204 is then used to update the exertion-physiological model 1205.

Figure 12B:
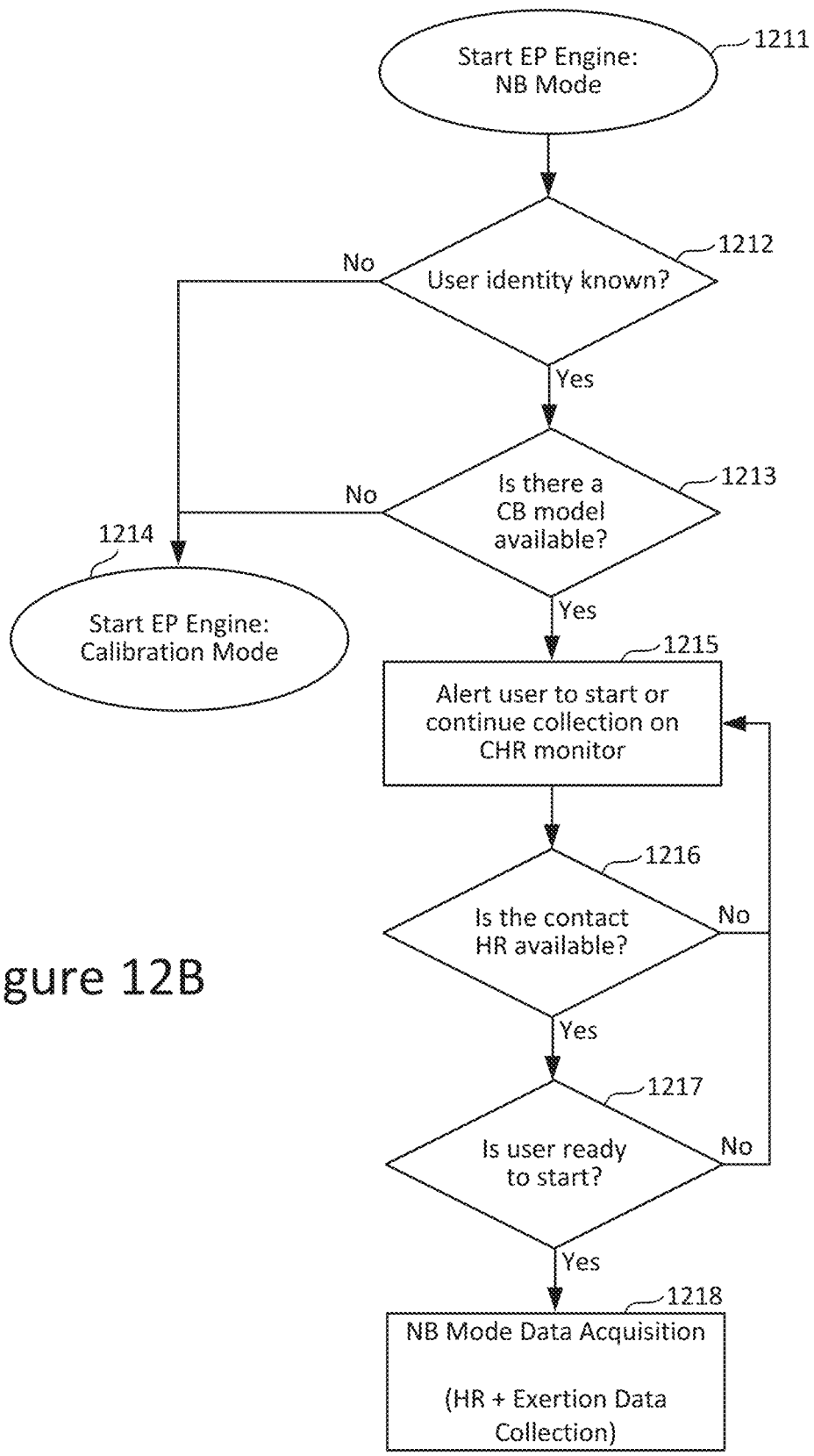
FIGS. 12B-12E provide a more detailed view for one embodiment of a conceptual method that can be used by the exertion-driven physiological monitoring system to deploy the next-beat EP engine models.

FIGS. 12B-12E provide a more detailed view for one embodiment of a conceptual method that can be used by the exertion-driven physiological monitoring system to deploy the next-beat EP engine models. FIG. 12B is a flow chart for an embodiment of the initialization methodology for the operation of the EP engine in the active NB modality. Starting at 1211, and in a similar fashion as to the methodology used for the creation of the calibration protocols, at step 1212 the system first verifies the user identity and at step 1213 inquires whether an exertion-physiological model (CB model) is available, which is also required to operate the system in the NB modality. If the user or associated CB model is not available, at step 1214 the EP engine redirects the user to proceed to the calibration process, so that a CB model may be created for the user. If a CB model is available, at step 1215 the system alerts the subject to use the contact heart rate monitor to provide an initial heart rate signal to the system and then proceed to start the operation of the system and commence gathering data in the NB mode at step 1218, as shown in the last process step in FIG. 12B. Before going to step 1218, the system checks whether a contact heart rate is available at 1216 and whether the user is ready to start at 1217, where a No at either of 1216 or 1217 loops back to the user alert of 1215 and a Yes at both leads to the data acquisition of step 1218.

The presence of the combined exertion and corresponding physiological response data streams as the NB modality is initiated represents again unique individual information about the user conducting the monitored physical activity and thus provides the opportunity to identify the subject being monitored. If the subject is identified, the EP engine can then jointly monitor these data streams and the NBQ confidence factor. If NBQ is larger than an appropriate preset value the EP engine will then confirm the identity of the user and proceed to authenticate it. This process is thus similar to the Identification/Authentication process described with the EP engine operating the CB modality as in FIG. 11F.

Figure 12C:
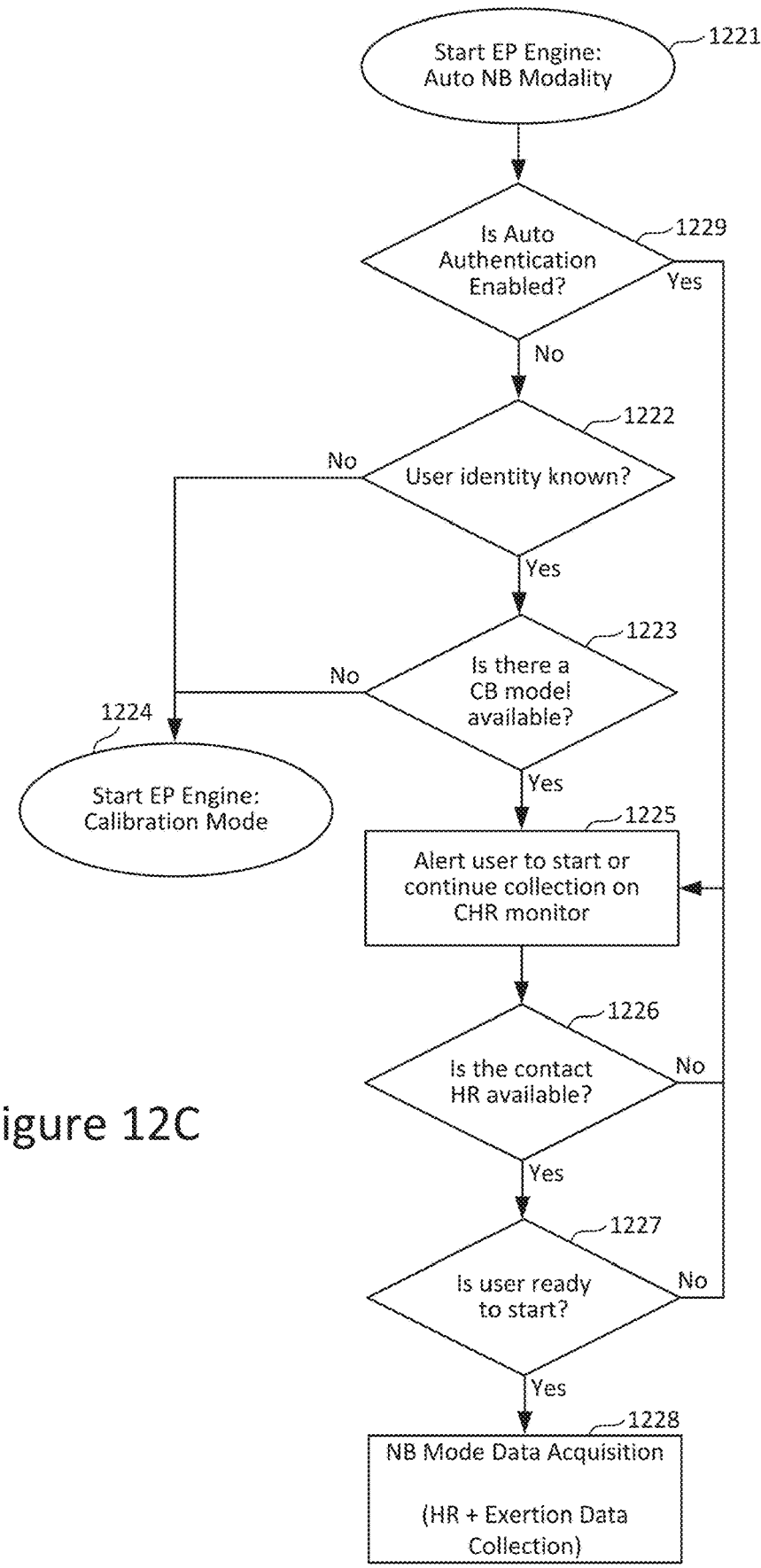

FIG. 12C is a flow chart for an embodiment for an initialization methodology for the operation of the EP engine in the active Auto NB modality with the "authentication feature" feature in place, starting at 1221. The flow of FIG. 12C is similar to that of FIG. 12B, but now includes a first step to determine whether or not auto-authentication is enabled at step 1229. If auto-authentication is enabled, the flow goes directly to step 1225; if not, the flow goes to step 1222. In the embodiment of FIG. 12C, aside from the initial step 1229, the other steps can correspond to those of FIG. 12B, with steps 1222-1228 respectively corresponding to steps 1212-1218.

Figure 12E:
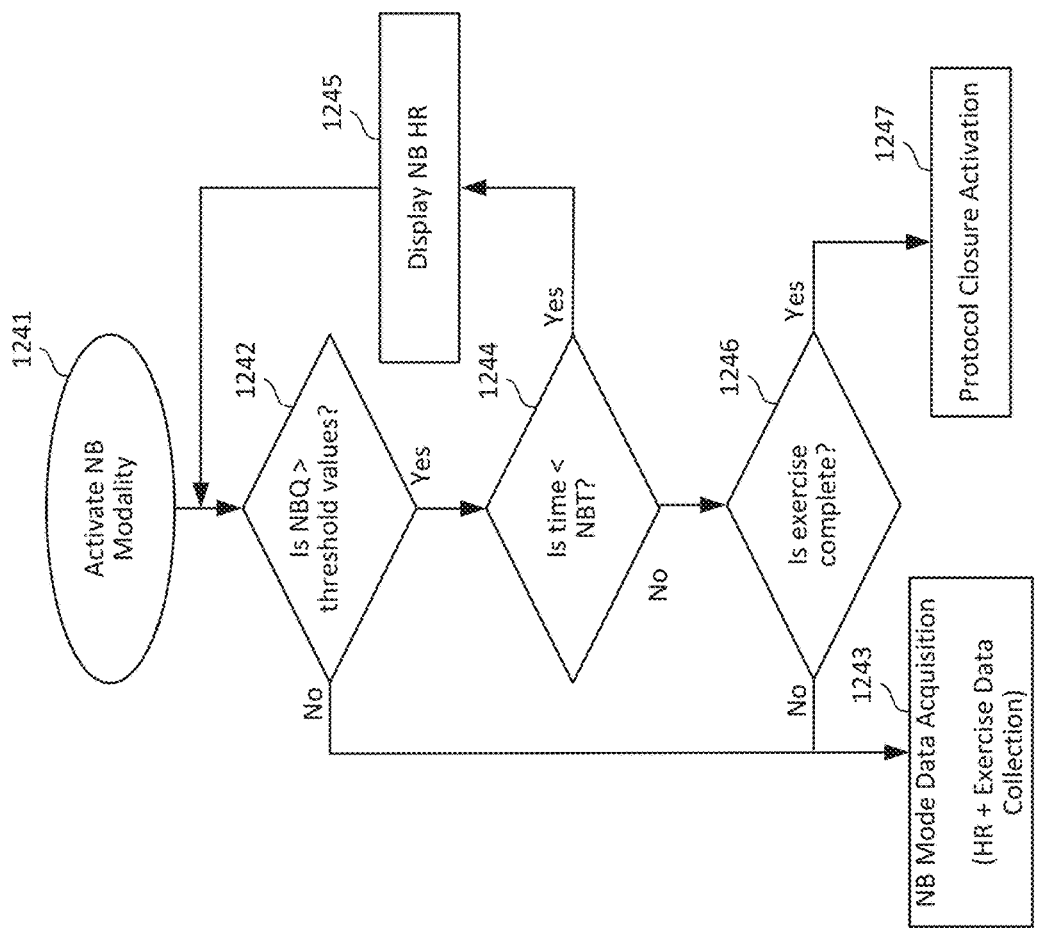
Figure 12D:
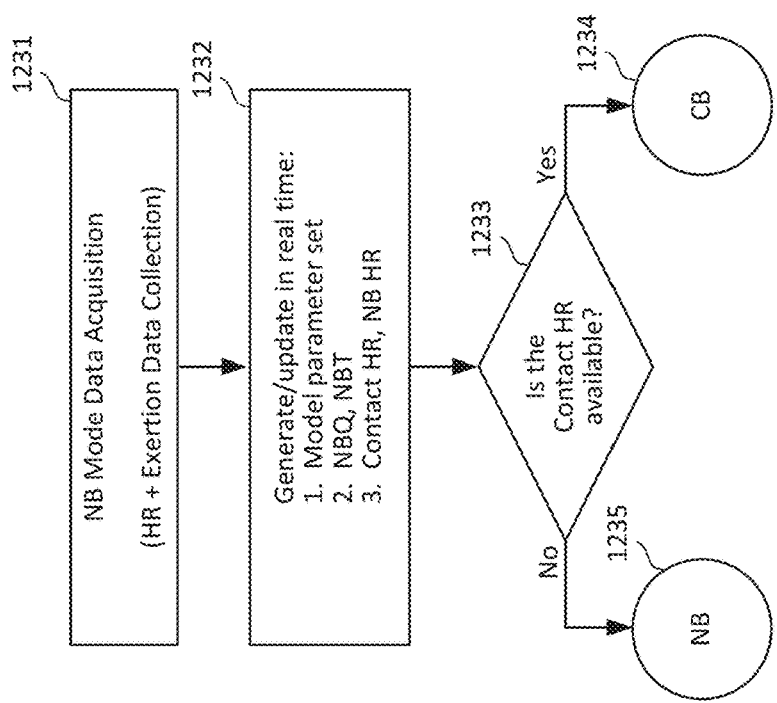

FIG. 12D is a flow chart to illustrate an embodiment for a switch methodology for the operation of the EP engine in the NB active mode, where the engine directs operation to either the CB or the NB modalities. This can follow the flow of FIG. 12C or 12B and starts with the "NB mode Data Acquisition" step 1231. As the system gathers data at step 1232, the EP engine will then compute a number of parameters to support the algorithmic operation of the NB modality. It will also compute and track, in real-time, the confidence factor NBQ, along with the corresponding NBT time window. Additionally, it will compute the contact heart rate signal, as well as the synthetic NB HR signal. Step 1233 again verifies whether there is a contact heart signal available, and if so, it will proceed to activate the deployment of the CB modality 1234. Otherwise, it will direct the EP engine to operate in the NB modality 1235, described with respect to FIG. 12E.

FIG. 12E is a flow chart illustrating an embodiment for the NB modality activation, starting at 1241. In this operation, at step 1242 the EP engine compares the confidence coefficient NBQ to a preset threshold value that has been algorithmically determined to ensure that, for the current user and current activity, there is a high likelihood of computing a synthetic NB HR with significant accuracy. If the NBQ value is below the threshold value (No path from step 1242), the flow goes to step 1243 for NB mode data acquisition, which can include heart rate data and exertion data collection. If the NBQ value is over the threshold values, at step 1244 the EP engine will then inquire whether the NBT time window is valid, and if so, the engine will proceed to start or continue to compute and display the NB HR signal at 1245 and loop back to step 1242.

Once NBT expires (No path from step 1244), the engine will disarm the EP engine, alert the user, and stop displaying the heart rate at step 1245. Upon the presence of a new contact heart signal the EP engine will resume in the CB modality and operate accordingly. Nonetheless, as the user alternates between holding onto the contact heart rate monitor and releasing the grip, the EP engine will alternate between the CB and NB modalities, and will provide the corresponding synthetic CB HR and NB HR signals, as long as the required criteria are met, respectively.

Step 1246 determines whether the exercise is complete. While the exercise is not complete, and NBQ and NBT become again higher than corresponding preset threshold values, the EP engine will be armed for NB operation once more. Thus, for as long as the contact heart rate is present, the NB engine will operate in the CB modality. Once the contact grip is removed, and if armed, the EP engine will be again triggered and the exertion-based computed heart rate, NB HR, will once more be computed and made available for the duration indicated by the new NBT. Upon completion of the exercise, the EP engine proceeds to the closure of the protocol at step 1247. The protocol closure activation process can again be as described in FIG. 9F, which includes saving the exertion and corresponding physiological response data streams to the cloud or local database for later access.

Figure 13:
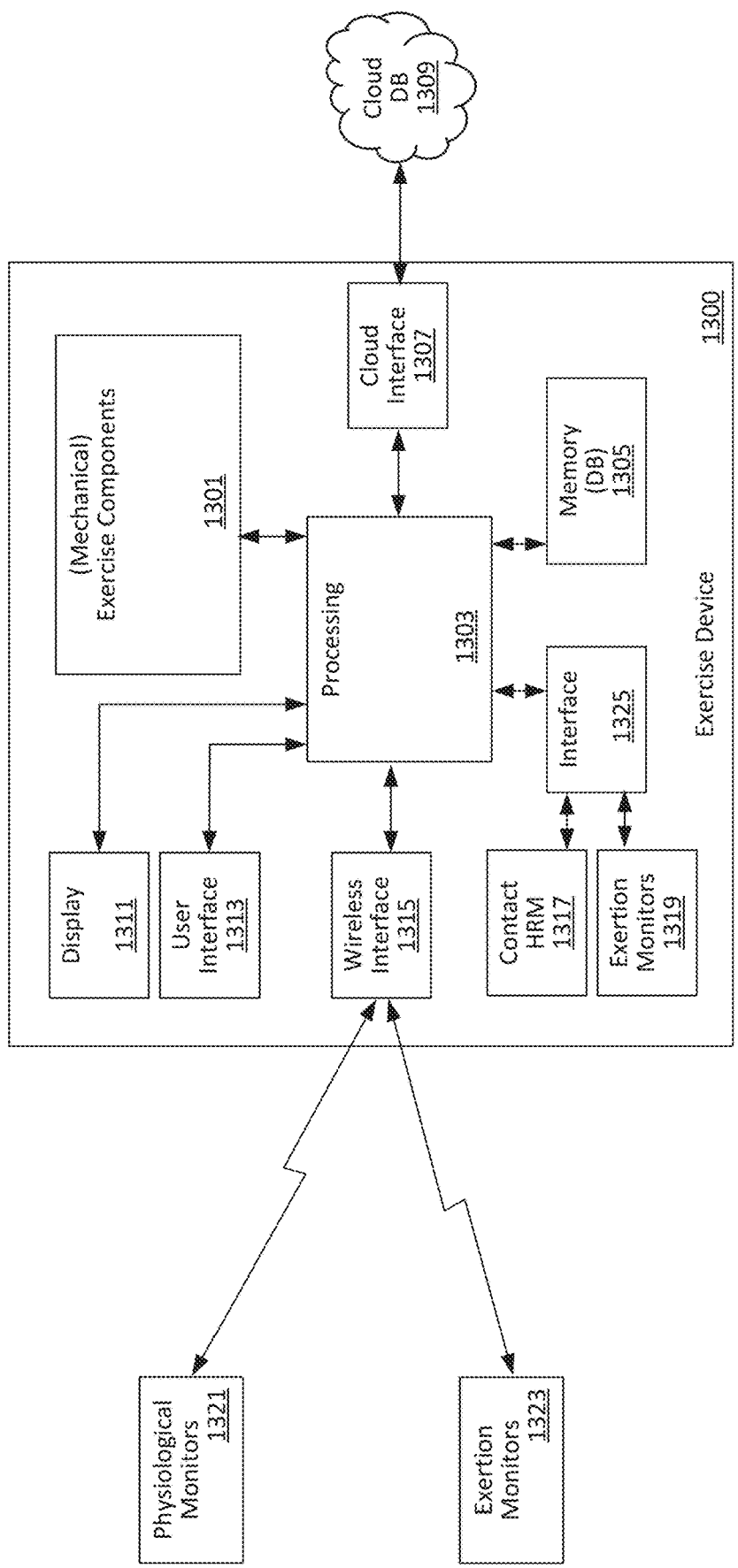
FIG. 13 is a block diagram for an embodiment of an exertion-driven physiological monitoring and prediction system as incorporated into exercise equipment.

FIG. 13 is a block diagram for an embodiment of an exertion-driven physiological monitoring and prediction system as incorporated into exercise equipment. The embodiment of FIG. 13 can again be the example of a treadmill or other exercise equipment, such as spin bike, and incorporates a number of functionalities and components that may not be included in other embodiments.

The exercise equipment 1300 includes the exercise components 1301 on which the fitness activity is actually performed, which would include the mechanical and electrical components of the treadmill, spin bike, or other fitness equipment commonly included in exercise without the additional features described here for exertion-driven physiological monitoring and prediction. For this discussion, elements such as the display 1311 and processing 1303 are shown as separated blocks, although many typical exercise equipment devices include such components combined. For example, a treadmill will commonly have some form of display, user interface, and processing related to its operation (i.e., to adjust incline in response a user input), but these are represented separately here as these can include the additional capabilities presented here.

Heart rate data for a subject can be provided by physiological exertion monitors 1317 incorporated into the exercise equipment 1300, such as contact heart rate monitors incorporated into the hand holds of a treadmill or handlebars of a spin bike, external physiological exertion monitors 1321, such as wearable devices illustrated with respect to FIG. 4 or optically based or other external devices, or some combination of external and incorporated physiological exertion monitors. Motion related metrics of a subject can similarly be computed from one or both of exertion signals provided by external exertion monitors 1323 and exertion monitors 1319 incorporated into the exercise equipment 1300. Examples of external exertion monitors 1323 include inertial measurement units or other measurement devices incorporated into wearables, optical sensors, or examples described above. Exertion monitors 1319 incorporated into exercise equipment can include devices such as accelerometers or sensors to determine factors such as treadmill incline, treadmill speed, rotational speed of a spin bike wheel, and so on. The IMUs or other exertion monitors 1323 and exertion monitors 1319 can provide the signals that can then be processed as described herein to determine an exertion level. As with the other tracking systems described, some confirmation/calibration against a true metric of exertion, such as any physiological marker that correlates with exertion, inclusive of heart rate is used. Exertion through any of these monitors could also be obtained with the aid of other related direct or indirect metrics that may even include the load the subject is holding, pushing, pulling and so forth, as long as it relates to the level of effort of the subject being monitored.

FIG. 13 also explicitly includes a wireless interface 1315 configured to receive the data signals from the external physiological monitors 1321 and exertion monitors 1323. The wireless interface 1315 can then be used to exchange data between these external monitors and the exercise equipment's processing 1303. Similarly, an interface 1325 is also explicitly shown for the contact heart rate monitor or other internal physiological monitors 1317 and internal exertion monitors 1319 that can be used to exchange data between these internal monitors and the exercise equipment's processing 1303. Although shown separately, the interfaces 1315 and 1325 and the processing 1303 can be part of the same circuitry components.

The embodiment for the exercise equipment 1300 also includes a display 1311 and user interface 1313 to provide and receive feedback from the subject. The display 1311 can be, or be part of, the user interface, such as in the case of a touch screen. The display 1311 can include the information commonly provided to a user of a given exercise device 1300 (e.g., incline or speed for a treadmill; resistance level, cadence, power for a spin bike) and the user interface 1313 can similarly provide the common user inputs for the exercise device 1300 (e.g., incline for a treadmill, resistance level for a spin bike). In the embodiments presented here, the display 1311 also provide a subject with information such as a protocol to follow, directly determined and/or synthetic exertion-based synthetic heart rate, and motion related exertion data. The user interface 1313 can be used by the subject to select between protocols.

The exercise equipment 1300 can also include a memory 1305 for storing and accessing databases including model parameters for protocols and user profiles for the processing circuitry of processing block 1303 and/or an interface 1307 that can be used for cloud databases 1309. The processing block 1303 can include one or more processors, including CPUs, GPUs, and other types of processing units, FPGAs, ASICs, integrated circuits, or other types of circuits to perform the processes described both above and in the subsequent discussion and perform these in hardware, software, firmware, or various combinations of these.

The embodiment of FIG. 13 is based on an example of exercise equipment 1300 that incorporates many of the elements of the system beyond the basic device of the exercise equipment 1301. In other embodiments, the system may lack the internal physiological monitors 1317 and exertion monitors 1319 (and corresponding interfaces 1325) and rely on external monitors. In some embodiments the processing block 1303 and other elements may be separate from the exercise equipment 1301, where this can include examples such as those described below when the fitness equipment involves free weights, for example. In still other examples discussed below, the subject may not be using exercise equipment, as such, but involved in an activity such as playing a field sport.

Figure 14:
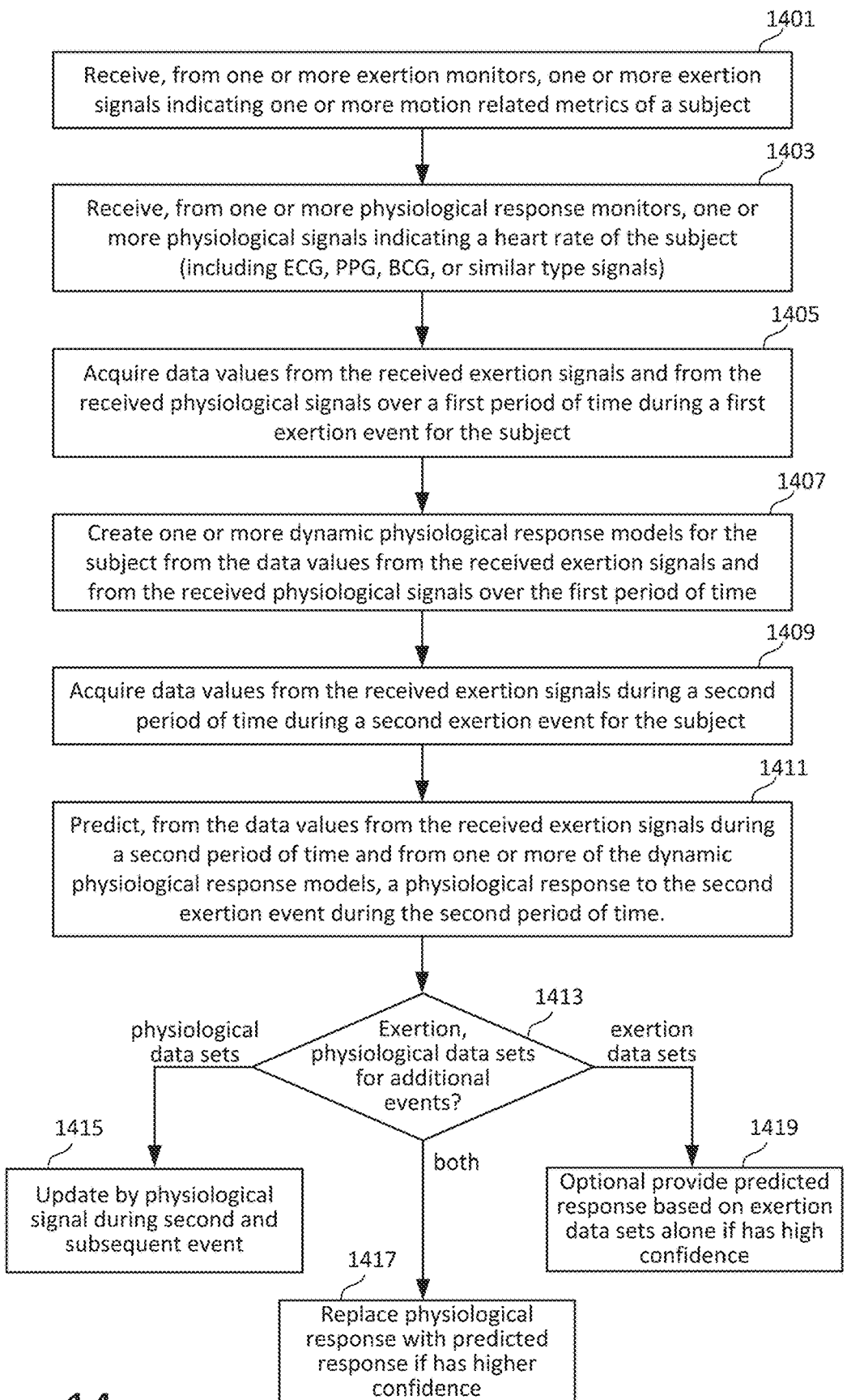
FIG. 14 is a flowchart for one embodiment of a method of exertion-driven physiological monitoring and prediction using the system of FIG. 13.

FIG. 14 is a flowchart for one embodiment of a method of exertion-driven physiological monitoring and prediction using the system of FIG. 13. The flow of FIG. 14 is a high level representation combining many of the features described in the various embodiments presented in earlier figures. The flow of FIG. 14 includes both the determination of a physiological response model (steps up to 1407) and also the subsequent steps (1409 and later steps) that use this response model. Depending on the implementation, these may be quite distinct processes and determined using differing exercise equipment. For example, the physiological response model for a subject may be determined according to a protocol and then stored into a database, and then being accessed on multiple occasions when the subject exercises.

Beginning at step 1401, signals are received from one or more exertion monitors that indicate one or more motion related metrics of a subject. The signals can be from exertion monitors 1319 incorporated into the exercise equipment 1300 or external exertion monitors 1323, either incorporated into wearable devices or other devices (e.g., monitors based on optical, acoustic, RF signals, or other technology). At step 1403, one or more physiological signals indicating the subject's heart rate are received, where these can be from an internal physiological monitor 1317 (such as a contact heart rate monitor, or ECG, PPG, BCG, or similar type signals) or a physiological monitor 1321 external to the exercise equipment such as a wearable device or other device, such as an optical heart rate monitor. The signals from steps 1401 and 1403 are received at the interfaces 1315, 1325, or both depending on the monitors, allowing the data values to be acquired by the system at step 1405, where they can then be stored and processed to create one or more dynamic physiological response models for the subject at step 1407. The data values can be stored in memory 1305 of the exercise equipment 1300 or memory external to the exercise equipment, such as the database 1309, from where they can be downloaded over the interface 1307 and stored in the memory 1305 to supply the dynamic physiological response models for a subject. The dynamic physiological response models for the subject can be determined by the processing 1303 of the exercise equipment 1300 or by external processing, such as in the cloud. The flow of FIG. 14 presents the steps in a particular order, but other orders can be used and typically steps 1401, 1403, and 1405 will be occurring concurrently or in an overlapping manner.

Once a dynamic physiological response model or models are established for a user, these can be used during an exercise activity. If previously established, the subject can select a model for use during a fitness activity that can then be retrieved, such as from a database in the memory 1305 of the exercise equipment or from an external database 1309, for use during a subsequent exertion event. Once the exertion event begins, at step 1409 the system can acquire data for exertion signals, from either the same exertion monitors as in step 1401, one or more different exertion monitors, or both. Based on the physiological response model or models of step 1407 and the received exertion signals at step 1409, at step 1411 the processing circuits 1303 can predict a physiological response for the synthetic heart rate values discussed above.

Upon completion of the first creation of a set of dynamic physiological response models resulting from collecting both exertion and physiological data sets from the first exertion event, step 1411 provides the capability of predicting response models by combining information from the existing models. Additionally, it provides the capability of updating the response models by combining information from the existing models and new physiological signals possibly available during a second or further additional events. This occurs at steps 1413, 1415, 1417, and 1419.

Step 1413 determines exertion data sets, physiological data sets, or both are available for a second or further additional events. If physiological data sets are available, the synthetic heart rate values of step 1411 can also be updated in some embodiments at step 1415 based upon data from one or more physiological response monitors during a second even, if available, providing an indication of the subject's directly measured heart rate. For a second or more additional events after the first event where both exertion and physiological data sets are collected, if the predicted physiological response has a higher confidence than the organic response from a physiological monitor, then the predicted response could optionally be used to replace the physiological response at step 1417, so as to provide a net higher accuracy response. If only exertion data sets are collected for additional events after the first event, if the predicted physiological response has a sufficiently high confidence, then the predicted response could optionally be made available based on exertion data sets alone at step 1419.

The embodiment presented above consequently offer a significant value for the monitoring of physical activities, such as the exemplary exercise on a treadmill used to illustrate these concepts, by providing an alternative method to generate a synthetic heart rate signal, for a defined period of time, in the absence of a signal generated by a physiological-based heart rate monitor. Furthermore, as more data are collected for a given subject, the current-beat and next-beat models are expected to become stronger and the corresponding current-beat confidence factor, CBQ, and the next-beat confidence factor, NBQ, and associated next-beat time window, NBT, will tend to converge to higher values, providing increased benefits. It should be noted that the synthetic CB HR and NB HR signals are not expected to follow any particular heart rate behavior; that is, as long as there are adequate models with corresponding qualified parameters CBQ, NBQ, and NBT, the synthetic heart rate signals should be computed within the expected preset accuracy levels, regardless of whether the exertion load increases, decreases, or stays at a given level.

The ability to provide an alternative method to generate a synthetic heart rate signal, either in the presence of a physiological heart rate monitor (CB modality) or for a defined period of time in the absence of a signal generated by a physiological heart rate monitor (NB modality), can apply not only to other fitness equipment machines, but also to other exercise settings, where a physical activity or an exercise is conducted. In the case of the fitness-equipment setting, the exertion is constrained within the normal functionality of the equipment, as well as the range of its operating parameters. In addition to the example of a treadmill, the fitness-equipment setting may include exercise equipment such as an elliptical trainer, a stair or a step climber, a stationary bike, a rowing machine, a spin bike, a bike trainer, among other fitness machines.

Exercise settings may also include a field or outdoor-type sports setting, where the exertion is constrained by the specific sport activity and the terrain or location where it is conducted. The outdoor-sports setting may include fitness activities such as walking, running, hiking, cycling, swimming, skiing, among other physical activities. Exercise settings may also include an indoor-cardio setting, with no use of a fitness equipment as detailed in the fitness-equipment setting, and where the exertion is constrained primarily by the specific cardio activity being conducted. The indoor-cardio setting may include aerobics, plyometrics, cross training, among other cardio activities. Exercise settings may also include a strength training setting, where the exertion is constrained by the type of equipment used or type of exercise conducted. The strength training setting may include circuit training equipment, free weights, resistance training, among other training activities. Exercise settings may also include yet other frameworks and corresponding setting profiles representative of the range of operational parameters of the settings.

In all of these cases, a system can monitor the exertion of a subject performing the activity through the use of at least one of a plurality of appropriate exertion monitors, including signals obtained from an IMU, as well as by using motion tracking monitors based on optical, acoustic, RF signals, or yet other sources. Using the EP engine and appropriate algorithms on these signals, these motion tracking monitors can effectively be rendered into exertion tracking monitors.

Additionally, the ability to provide an alternative method to generate a synthetic heart rate signal could also apply not only to single individuals, but also to groups of subjects in any of the mentioned exercise settings, who might not naturally want to use a continuous heart rate source such as a chest strap or other human wearable devices. Thus, individuals or groups of individuals can benefit by using a combination of a locally available contact heart rate monitor for initiating and periodically reactivating the CB and NB modalities, and the predicted synthetic heart rate signals described above. Personalized CB and NB metrics computed for each individual within a group of individuals or a subgroup thereof, along with aggregate sub-group and group metrics may then be used for a number of purposes including the tracking of a group and subgroups thereof for the purposes of training effectiveness, performance over time, and yet other purposes.

Monitoring exertion can be more readily implemented in some exercise settings, while potentially more challenging in others. In the case of the treadmill exemplary embodiment within the fitness-equipment setting, it is clear that using one of at least one or more exertion monitors, such as the exemplary IMU detailed in the examples presented earlier, may be employed not only to monitor the exertion of a subject carrying out a protocol on the treadmill, but also to predict a synthetic heart rate signal based on exertion-physiological models using the methods presented in this disclosure. This allows the techniques described here to be readily available in this embodiment, as a subject can use the contact heart rate sensors typically available on treadmills to monitor the subject's heart rate, while also benefitting from the presence of the concurrent synthetic CB HR signal. The subject can also benefit from the presence of the NB HR signal for the duration established by NBT, when the subject does not make contact with the heart rate sensors where, again, with the current-beat and next-beat models expected to become stronger as more data are collected.

Considering other cases, such as free weights as an exemplary embodiment within the strength training setting, contact heart rate is not typically available. The techniques presented here may be deployed in this setting by first conducting a calibration process as detailed in this disclosure. One example may include a subject wearing a chest strap monitor to record the heart rate signal while lifting various sets of free weights representative of the range of weights and lifting protocols to be monitored in the embodiment. In this example, the subject may use a human wearable device with an embedded IMU to track the body lifting motion while carrying out the lifting protocol. Once the calibration protocol is completed and an exertion-physiological model is created for the intended range to be monitored, the subject may commence the operation in the current-beat and next-beat modalities.

Some differences, however, may be noted when comparing the application of these techniques to examples such as free weights in contrast with the treadmill example. The current-beat approach uses a dual heart rate signal to be generated. In the exemplary case of the treadmill, one heart signal source was obtained using a contact heart rate monitor, with the second source obtained synthetically (CB HR) from the exertion signal and the current-beat exertion-physiological models. In the case of free weights, an exemplary embodiment may include an ECG-based chest strap used as a source to obtain a first heart rate signal, along with two human wearables with embedded IMUS worn on the left and right wrists, respectively. The corresponding exertion signals are then monitored and the synthetic second heart rate (CB HR) signal is generated. This method is effective but not very attractive, as the subject would be required to wear a chest strap and two separate human wearables. In some embodiments, this requirement may be somewhat relaxed by using two wrist-based human wearables with built-in photoplethysmography (PPG) based heart rate monitors and IMUs. Note that this approach enables a single free weight, such by the left or right hand, to be lifted at a time, while still monitoring an exertion signal and a heart rate signal. If both left and right free weights are lifted concurrently, then a single heart signal is computed based on the combination of the two individual heart rate signals, which in the absence of noise should provide the same heart rate. In the presence of some noise, one of the signals may dominate and still enable the computation of the heart rate. In this case there will also be two individual IMU signals, which will be processed algorithmically to compute an appropriate representation of the subject's level of exertion.

The synthetically generated CB HR can then be used to further improve the robustness of the PPG signals, should the PPG signals be temporarily affected by noise. If the quality of the CB HR is suitable, it can be used to replace the potentially degraded PPG signals. This approach, however, would still require using two human wearable devices. In another exemplary embodiment, the need for human wearables can be further reduced by replacing them with machine wearables, as detailed earlier in the present disclosure. In the case of free weights, one example may deploy at least one of one or more PPG heart rate monitors with built-in IMUs in every free weight to be used on any protocol intended to be monitored. It should be clear that the intent of the machine wearable is to monitor the subject's exertion. Thus, whether the exertion monitor is truly a machine wearable, as in the case of a sensor-instrumented cover that gets ported and placed on any free weight used, or is embedded or affixed to the free weights, it is equally applicable to the intent of exertion monitoring. In this exemplary embodiment, the data would be collected in the current-beat mode, and the synthetic CB HR would be available once the requirements of this modality are met.

The next-beat modality uses a dual heart rate signal to be generated at the beginning of the monitoring. In the example presented above, where one or more PPG heart rate monitors with built-in IMUs are deployed in the free weights, the next-beat modality could again provide the benefit of availing a qualified synthetic heart rate (NB HR) during a period of time established by NBT. NB HR could then provide a synthetic heart rate in the case when the PPG signals are not present due to motion artifacts or other noise sources.

The exertion monitor, as described in the examples presented, provides a method to continually monitor the exertion of a subject conducting a prescribed physical activity. When appropriate, the monitor is also able to provide qualified synthetic heart rate CB HR and NB HR signals. The current-beat and next-beat modalities, however, require the presence of first heart rate signal to be collected. In the case of the current-beat modality, the heart rate signal needs to be collected concurrently, while in the case of the next-beat signal the heart rate signal needs to be collected immediately prior to providing a qualified synthetic signal. In the absence of a first heart rate signal, however, the exertion monitor is still able to monitor the subject's exertion which has been calibrated following the methods presented here. Thus, in the case of a physical activity conducted on a treadmill, where no contact heart monitoring or any other heart rate monitoring method is utilized, the embodiments presented here still provide the benefit of providing the subject with a real-time exertion signal, which is representative of the level of physical effort associated with the activity. This value is a result of having initially calibrated the exertion monitor and developed corresponding exertion-physiological models, as described in this disclosure.

Similarly, in the case of free weights instrumented with IMU-based exertion monitors without PPG-based heart rate monitors, a real-time exertion signal may also be obtained, which is representative of the level of physical effort associated with the weight-lifting activity. Thus, the system can still provide significant value to a subject, even when a first heart rate signal source is not available, and consequently no synthetic heart rate is provided. This value is particularly significant in exercise settings, where in the absence of a heart-rate monitor human wearable, the notion of "machine wearables" may be more challenging to deploy. In the case of free weights, for example, a contact heart rate monitor could be mounted in a plurality of locations in the weight rack. In one embodiment, contact heart rate monitoring could be made available near, next to or under every weight, so that the subject's heart rate could be monitored before and after every weight-lifting activity. These heart rate pre-exercise and post-exercise data sets would still be used to enhance the robustness of the exertion-physiological models.

In the case of free weights, for example, in one set of embodiments individual free weights, such as dumbbells or weight bars, could incorporate built-in IMUs. Thus, the free weights with built-in IMUS will continually provide an exertion signal. Contact heart rate monitors can be located in the near vicinity of the subjects, such as part of a weight rack, which could be used to monitor heart rate immediately before and after every free weight drill. If the free weights are instrumented with additional PPG-based heart signal monitors, then CB HR and NB HR signals may also be provided. In other embodiments for lifting free weights, handles for a contact heart rate monitor can be on the sides of the weight bench, such as handles previously incorporated without this capability that are often already on weight benches.

In the case of an outdoor-sports setting, as for example a soccer game, contact heart rate is not typically available. In this type of setting, embodiments for the techniques presented here can be deployed by first conducting a calibration process as described above. One example may include one or more team players wearing a chest strap to monitor the heart rate signal while playing one or more soccer games representative of the range of physical activities to be monitored. In this example, the subjects may use a human wearable, such as those described above with respect to FIG. 4, with an embedded IMU that could simply be placed on top or built-in a shoe, or soccer uniform or garment, and which would eliminate the burden of a wrist-based or other typical human wearable. Optionally, an optical exertion monitor could be implemented by using an optical tracking system in conjunction with the calibration methods presented in this disclosure, and which produce exertion-physiological models. The soccer players could benefit from the exertion signal not only as a metric of the level of effort of their physical activity, but also as a component to inform their training and game related performance.

The aspects described above highlight the value of knowing the physiological response, such as a heart rate, to physical exertion. The use of a physiological response such as heart rate is familiar, as is the concept of heart rate and the value of exercising with a certain frequency and intensity in order to stay healthy, such as recommended by the CDC. The preceding discussion further presents the concept of an exertion monitor, that, once calibrated, is able to produce a synthetic heart rate signal that can provide an equivalent to the physiological heart rate signal under the framework described. Thus, once calibrated, knowing the exertion signal within the existing framework provides a signal that can be as valuable as heart rate, so that CDC and similar recommendations could be translated into exertion metrics that could match, one-to-one, the moderate-intensity and high-intensity protocols they promote.

Consequently, the presented techniques describe the creation of an exertion signal, resulting from an exertion monitor that has been pre-calibrated on a prior event with a corresponding physiological monitor. In the absence of a physiological monitor, an exertion monitor can compute and provide an exertion metric, which would vary based on the exertion setting, be it a treadmill, a soccer game or a swim lap. But since the exertion metric in each of these activities is also tied to a common physiological exertion metric such as heart rate, they would all provide equivalent metrics and thus a user could accumulate, for example, 10 exertion units during a treadmill protocol, 20 exertion units playing a soccer game and 8 exertion units during a number of swim laps and at the end of the day end up with a cumulative 10+20+8 units of exertion.

Figure 15:
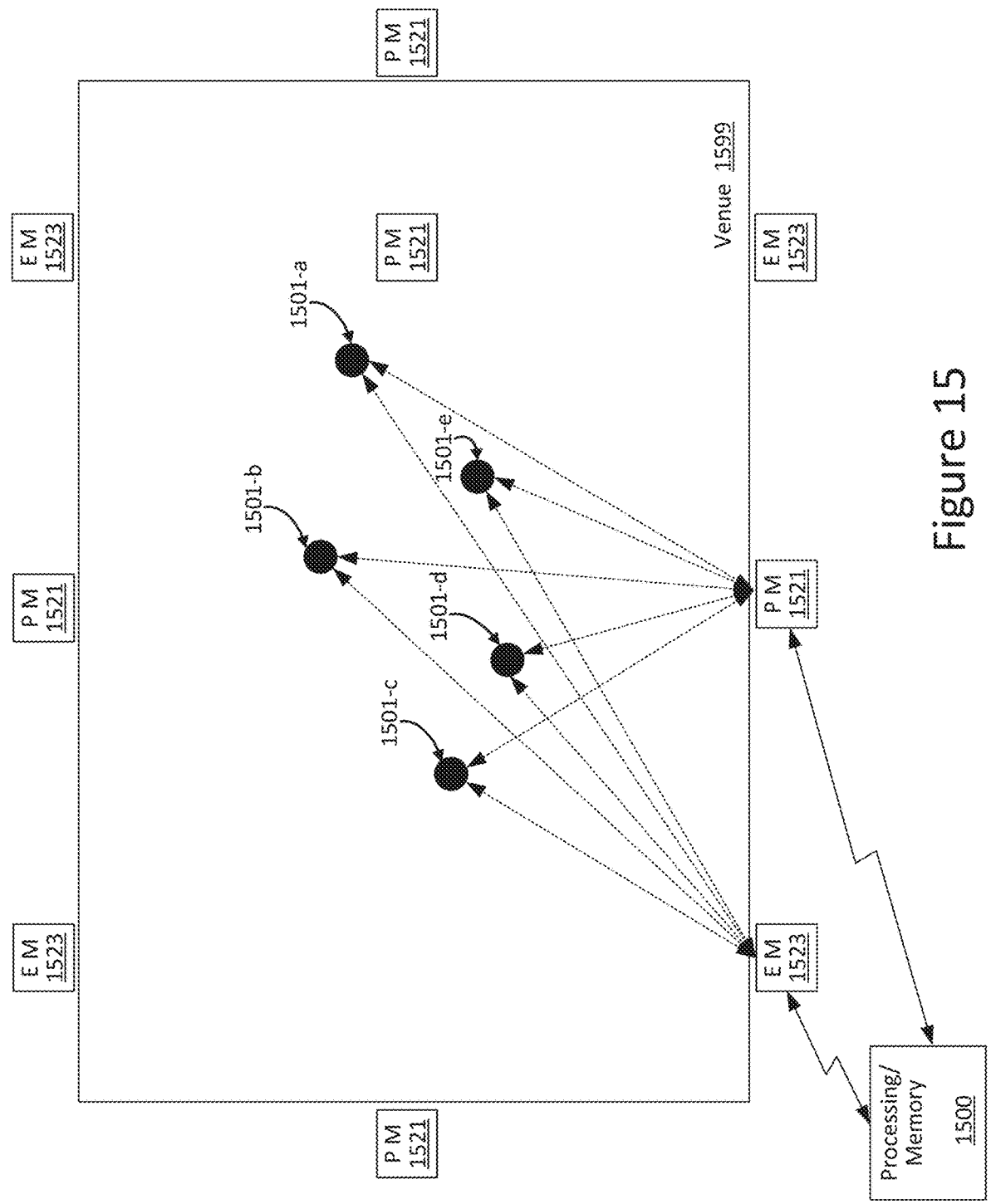
FIG. 15 looks at the application of the described exertion-driven physiological monitoring and prediction method and system to a venue in which one or more subjects are exercising.

FIG. 15 looks at the application of the described exertion-driven physiological monitoring and prediction method and system to a venue in which one or more subjects are exercising. The venue 1599 can be one of the indoor settings described above, such as gymnasium or weight room, or one of one or the outdoor setting described above, such as a soccer or other playing field, a location for walking, running, hiking, cycling, swimming, skiing, or venue for other physical activities. The five, in this example, shown subjects 1501-*a*, 1501-*b*, 1501-*c*, 1501-*d*, 1501-*e* could be members of an aerobics class or players in a game of soccer or other sport, for example. One or more of the subjects 1501-*a*, 1501-*b*, 1501-*c*, 1501-*d*, 1501-*e* could also be using exercise equipment.

In or around the venue are a number of exertion monitors E M 1523 to provide exertion signals corresponding to the individual subjects exercising at the venue. Depending on the embodiment, the exertion monitors E M 1523 could be used remotely and could operate based on tracking the subjects 1501-*a*, 1501-*b*, 1501-*c*, 1501-*d*, 1501-*e* with one or more of an optical tracking system, an acoustic system or a radio frequency system, for example. In some embodiments, exertion monitors E M 1523 could alternately or additionally be receivers for wearable exertion monitors or exertion monitors built into exercise equipment being used by the subjects 1501-*a*, 1501-*b*, 1501-*c*, 1501-*d*, 1501-*e* within the venue 1599. To avoid the drawing becoming overly cluttered, only one of the exertion monitors E M 1523 is shown monitoring the subjects 1501-*a*, 1501-*b*, 1501-*c*, 1501-*d*, 1501-*e* as represented by the broken line arrows. More generally, on or more of the exertion monitors E M 1523 can monitors each of the subjects and each of the subjects can be monitored by one or more of the exertion monitors E M 1523. In some embodiments one or more physiological monitors PM 1521 can also be located in or around the venue 1599, where these can use remote sensing and may also be receivers for physiological monitors incorporated into wearables worn by the subjects or incorporated into exercise equipment used by the subjects. For example, the physiological monitor PM 1521 could be a contact heart monitor incorporated into a weight rack, as described above.

The exertion monitors EM 1523 can provide exertion signals for the users to one or more processors and associated memory 1500, such as through a wireless or wired connection. The structure of the one or more processors and associated memory 1500 can be similar to that described with respect to the FIG. 13. Based on the exertion signals from the subjects 1501-*a*, 1501-*b*, 1501-*c*, 1501-*d*, 1501-*e*, the processing circuits 1500 can identify the subjects and, for each of the subjects, retrieve one or more dynamic physiological response models for each of the identified subjects, acquire data values from the received exertion signals during an exertion event, and individually predict a physiological response from the data values from the received exertion signals during the exertion event and from the dynamic physiological response models, where this process can be as described in the various embodiments presented above. Based on the exertion signals, in some embodiments the processing circuits 1500 can also identify and authorize the type of exercise equipment being used in the venue and identify activities performed by the identified subjects. For embodiments also incorporating physiological monitors PM 1521, the physiological signals from one or more of the identified subjects 1501-*a*, 1501-*b*, 1501-*c*, 1501-*d*, 1501-*e* during the exertion event and used to update the predictions of the physiological response for the identified subjects.

Figure 16:
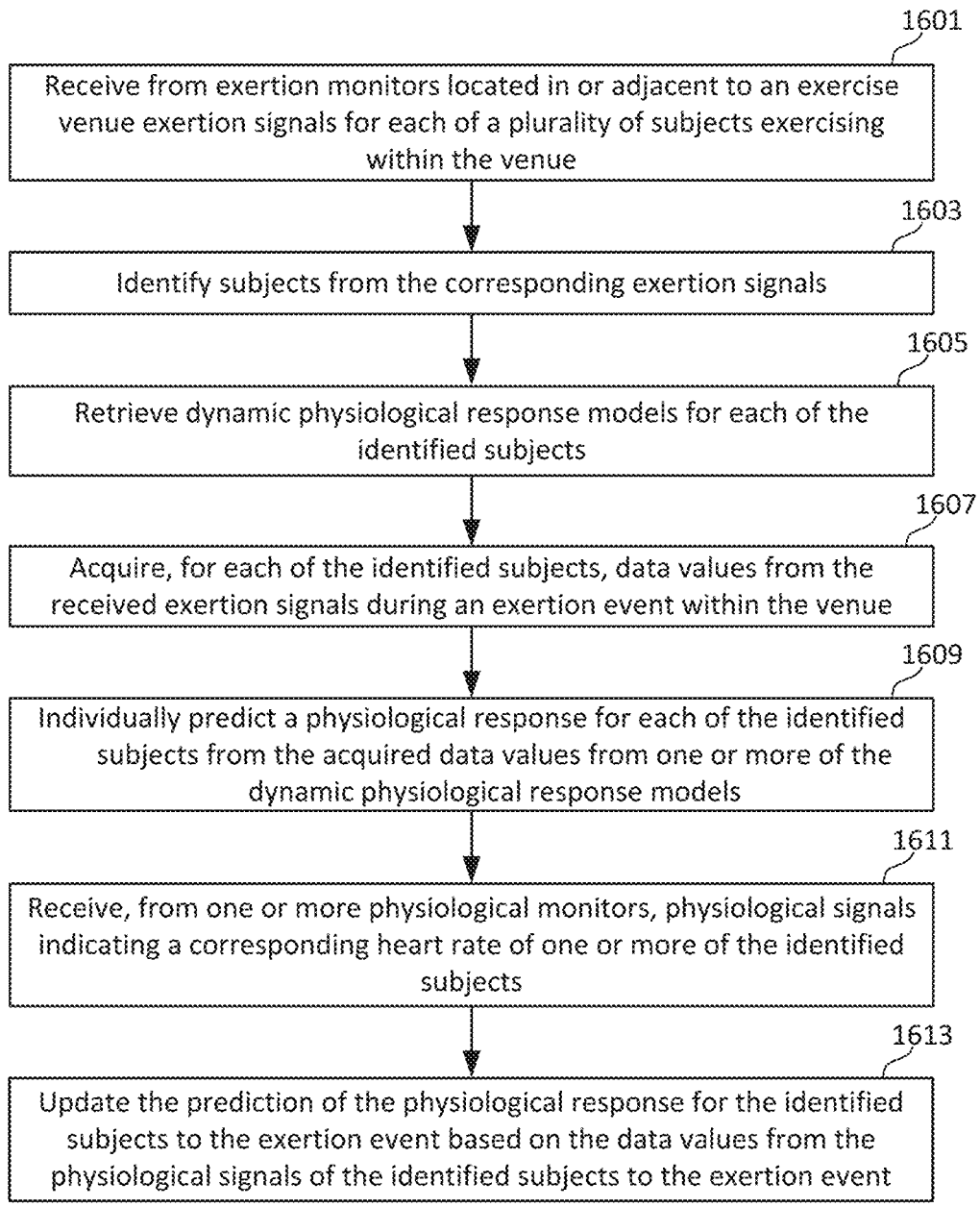
FIG. 16 is a flowchart for one embodiment of a method of exertion-driven physiological monitoring and prediction using the system of FIG. 15.

FIG. 16 is a flowchart for one embodiment of a method of exertion-driven physiological monitoring and prediction using the system of FIG. 15. Starting at step 1601, exertion signals indicating one or more motion related metrics for each of a plurality of subjects exercising within the venue 1599 are received at the processing circuits of the one or more processors and associated memory 1500 for the exertion monitors E M 1523. The exertion monitors E M 1523 may already be present at the venue or located there before the subjects begin the exercising. In step 1603, the one or more processors and associated memory 1500 can perform an identification of the subjects from the corresponding exertion signals and, at step 1605, retrieve one or more dynamic physiological response models for each of the identified subjects. Similar to the process of FIG. 14, for each of the identified subjects, the one or more processors and associated memory 1500 acquires data values from the received exertion signals during an exertion event within the venue 1599 at step 1607. At step 1609, the one or more processors and associated memory 1500 can then individually predict a physiological response for each of the identified subjects from the data values from the received exertion signals during the exertion event and from one or more of the dynamic physiological response models.

If physiological monitors P M 1521 are also being incorporated, at step 1611 the one or more processors and associated memory 1500 receive physiological signals indicating a corresponding heart rate of one or more of the identified subjects. Although the flow of FIG. 16 has step 1611 following 1609, the one or more processors and associated memory 1500 can begin receiving the physiological signals at the same time that they begin the exertion signals at step 1601. At 1613, the one or more processors and associated memory 1500 can then update the prediction of the physiological response for the identified subjects to the exertion event based on the data values from the physiological signals of the identified subjects to the exertion event.

The exertion monitor, as described in the examples presented, thus provides a method to monitor the exertion of a subject conducting a wide variety of prescribed physical activities. Subjects monitored with the techniques presented herein may extend beyond human subjects and include suitable non-human animal subjects. For example, the equine industry has an interest in the general fitness and conditioning of their horses in both recreational and competitive disciplines. In some embodiments, equine heart rate monitoring can be based on ECG chest straps typically designed to communicate the heart rate via Bluetooth to the rider.

Figure 17A:
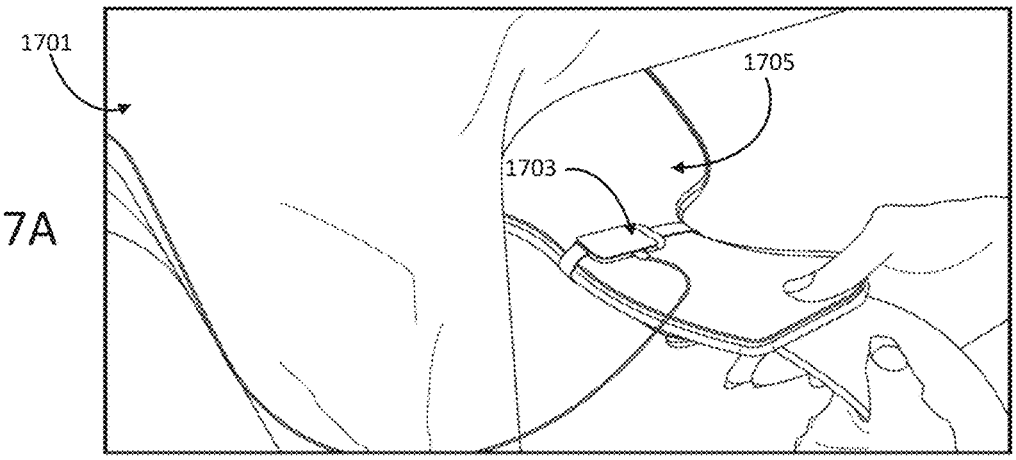
FIGS. 17A-17C illustrate embodiments for physiological response monitors and exertion monitors for a horse subject.
Figure 17B:
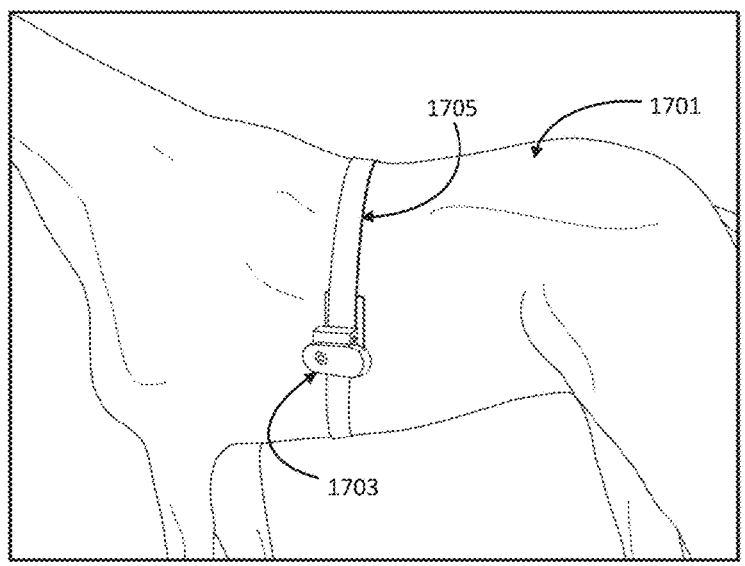
Figure 17C:
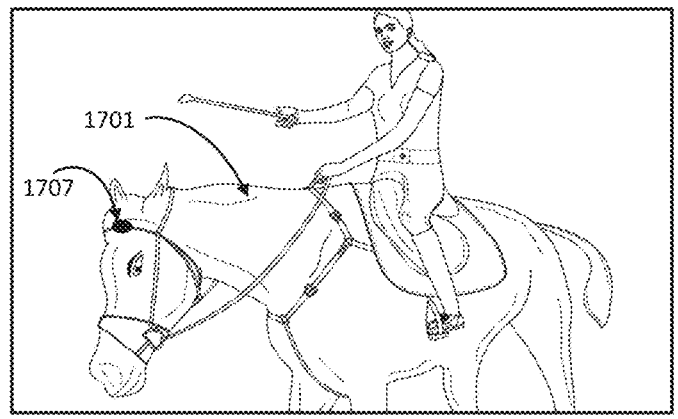

FIGS. 17A-17C illustrate embodiments for physiological response monitors and exertion monitors for a horse subject. As shown in FIG. 17A, a horse 1701 is shown while being outfitted with a chest strap 1705 including a heart rate monitor 1703. FIG. 17B shows the horse 1701 with the HRM strap 1705 in place. FIG. 17B illustrates a separate strap, but in some embodiments a HRM could be incorporated into cinch or girth used to keep a saddle in place. FIG. 17C shows a horse 1701 during a training routine where heart rate is being monitored. An IMU 1707, along with exertion-physiological models managed by the EP engine, illustrates the use of an exertion monitor. In this example, the IMU 1707 is mounted on the head of the horse 1701, such as mounted on or incorporated into the horse's halter or headgear. This monitor 1707 can be used in conjunction with the chest-strap 1705 as shown to deploy the current-beat and next-beat modalities. While monitoring heart rate alone may provide valuable information on the health and wellness of the horse, the use of the methodology presented above in the human subject context can provide further value in monitoring the level of exertion of horses and other non-human animals in various types of physical activities, and particularly in training and competitive activities.

As with a human subject, once exertion-physiological models are created using the methods described above, the current-beat and next-beat modalities may be applied, should the heart-rate monitor fail to provide a valid heart rate, or have periods due to signal noise where no heart rate is provided. Heart rate monitoring alone does not provide the rider with the level of exertion that created the heart rate signal, which is a component of embodiments presented here. The information on the real-time correlation of exertion and heart rate provides a unique value to monitoring the wellness and fitness level of the horse subject. Furthermore, in the absence of fitting a horse with a chest strap or other heart-rate monitors, it is still valuable to create exertion-physiological models and to monitor exertion during various physical activities. Exertion could be monitored by attaching an IMU-based exertion monitor to the horse in one or more body locations. While a trainer could obtain the data from the IMU while riding the horse, other means of obtaining the data may be deployed, so the data could be retrieved without the need to riding the horse. Further, for settings where the location of the horse is constrained, such as in a racetrack or other venues, an optical exertion tracking system could be used to monitor the exertion of one or more horses, without the need to use the "animal wearable" IMU-based exertion monitor, in similar ways as described earlier in this disclosure. Other exertion tracking methods may also be used.

Subjects monitored with the techniques and systems presented here may also include animals used in animal research and animal clinical studies. Mice, for example, are commonly used in studying the effect of targeted therapies using combinations of various drugs and regimes as well as other mouse clinical trials. Other studies using mice have focused on the impact of physical activity in preventing heart disease. Heart rate monitoring in mice has been developed using ECG-based contact heart rate, where the mice are placed on a plate containing ECG electrodes. The various techniques described above can also be applied to monitor exertion in mice, including by use of IMUs mounted on the mice bodies, or other methods not requiring the use of "animal wearables", such as using remote exertion tracking monitors. Mice cages may also be instrumented with IMUs, using similar methodologies as described when mounting IMUs on a fitness equipment, while tracking the physical activity of the subject.

The ability to create an extended heart rate signal by using the predicted synthetic heart rate signal described opens up the possibility for a single user or groups of users, who do not use a chest strap or other human wearable devices, to access both exertion and physiological information about their physical activity just by virtue of conducting the activity on a properly instrumented exercise setting. Thus, for social interacting groups in social media or other platforms, the techniques described can create individual or group metrics that can be shared and potentially promote further fitness activities within the group.

For any of the embodiments presented here, the methods and systems introduced the concept of utilizing a subset of the present system, whereby once the models created by the EP engine are deemed to have accurate values, there will be a high correlation between the exertion and corresponding physiological response. This subsystem would include the EP engine and the exertion monitors, but would not require the physiological monitors. The subsystem would then provide the ability to monitor the exertion of the subject or group of subjects in different exercise settings for which models have been created. This subsystem thus becomes a personal exertion monitor. It could also be "portable" in a physical sense, where the exertion sensors could be carried from one of one or more similar exercise settings to the next, such as in the sense of "machine wearable devices", which can evolve to "exercise setting wearable devices", or simply be portable in the digital sense, where every exercise setting has a dedicated exertion monitor, and thus the subject could simply access the localized exertion data digitally.

According to a first set of aspects, a method includes: receiving, from one or more exertion monitors, one or more exertion signals indicating one or more motion related metrics of a subject; receiving, from one or more physiological response monitors, one of more physiological signals indicating a heart rate of the subject; and acquiring data values from the received exertion signals and from the received physiological signals over a first period of time during a first exertion event for the subject. The method also includes: creating, by one or more processing circuits, one or more dynamic physiological response models for the subject from a combination of the data values from the received exertion signals and the received physiological signals over the first period of time; acquiring data values from the received exertion signals during a second period of time during a second exertion event for the subject; and predicting, by the one or more processing circuits, from the data values from the received exertion signals during a second period of time and from one or more of the dynamic physiological response models, a physiological response of the subject to the second exertion event during the second period of time.

In additional aspects, a system includes: one or more interfaces configured to receive, from one or more exertion monitors, one or more exertion signals indicating one or more motion related metrics of a subject; a memory; and one or more processing circuits connected to the one or more interfaces and to the memory. The one or more processing circuits are configured to: retrieve, from the memory, one or more dynamic physiological response models for a subject; acquire data values from the received exertion signals during an exertion event for the subject; and predict, from the data values from the received exertion signals during the exertion event and from one or more of the dynamic physiological response models, a physiological response for the subject to the exertion event.

In other aspects, a method includes: receiving, from one or more exertion monitors, one or more exertion signals indicating one or more motion related metrics of a subject; retrieving one or more dynamic physiological response models for the subject; acquiring data values from the received exertion signals during an exertion event for the subject; and predicting, from the data values from the received exertion signals during the exertion event and from one or more of the dynamic physiological response models, a physiological response for the subject to the exertion event.

In another set of aspects, an exercise equipment includes: one or more exercise components; one or more physiological response monitors, including a contact heart monitor, configured to provide heart rate data of a subject during an exertion event using the one or more exercise components; one or more exertion monitors configured to indicate one or more motion related metrics of a subject during an exertion event; a memory configured to store one or more dynamic physiological response models for the subject; and one or more processing circuits connected to the one or more physiological response monitors, to the one or more exertion monitors, and to the memory. The one or more processing circuits configured to: retrieve, from the memory, one or more dynamic physiological response models for the subject; receive, from the one or more exertion monitors, the one or more motion related metrics of a subject during the exertion event; predict, from the one or more motion related metrics of a subject during the exertion event and from one or more of the dynamic physiological response models, a physiological response for the subject to the exertion event; receive, from the one or more physiological response monitors, the heart rate data of the subject during an exertion event using the one or more exercise components; and during the exertion event, update the prediction of the physiological response of the subject to the exertion event based on the heart rate data of the subject to the exertion event.

In other aspects, a method includes calibrating one or more exertion monitors by, for each of the one or more exertion monitors: receiving, from the exertion monitor, exertion signals indicating one or more motion related metrics of a subject during one or more exertion events in a corresponding exercise setting; receiving, from one or more physiological response monitors, physiological signals indicating a heart rate of the subject during the one or more exertion events in the corresponding exercise setting; and determining a correspondence between the motion related metrics and the heart rate for the subject during the one or more exertion events in the corresponding exercise setting. Subsequent to calibrating the one or more exertion monitors, the method also includes for each of the one or more calibrated exertion monitors: monitoring exertion signals for the subject during one or more subsequent exertion events in the corresponding exercise setting; determining motion related metrics for subject during the one or more subsequent exertion events in the corresponding exercise setting from the monitored exertion signals; and generating a synthetic heart rate value for the subject during the one or more subsequent exertion events in the corresponding exercise setting from the determined motion related metrics and the correspondence between the motion related metrics and the heart rate for the subject.

Additional aspects include a system of one or more exertion monitors. Each of the one or more exertion monitors are configured to: provide exertion signals indicating one or more motion related metrics of a subject during one or more exertion events in a corresponding exercise setting; receive calibration information providing a correspondence between the motion related metrics and a heart rate for the subject during the one or more exertion events in the corresponding exercise setting; subsequent to receiving the calibration information, monitoring exertion signals for the subject during one or more subsequent exertion events in the corresponding exercise setting; determining motion related metrics for the subject during the one or more subsequent exertion events in the corresponding exercise setting from the monitored exertion signals; and generating a synthetic heart rate value for the subject during the one or more subsequent exertion events in the corresponding exercise setting from the calibration information.

In further aspects, a system includes a plurality of exertion monitors configured to be located in or adjacent to an exercise venue, a memory, and one or more processing circuits. The plurality of exertion monitors is configured to provide corresponding exertion signals indicating one or more motion related metrics of a subject for each of a plurality of subjects exercising within the venue. The one or more processing circuits are connected to the memory and configured to: receive from the exertion monitors the corresponding exertion signals for each of a plurality of subjects exercising within the venue; identify the subjects from the corresponding exertion signals; retrieve, from the memory, one or more dynamic physiological response models for each of the identified subjects; acquire, for each of the subjects, data values from the received exertion signals during an exertion event within the venue; and individually predict for each of the subjects a physiological response from the data values from the received exertion signals during the exertion event and from one or more of the dynamic physiological response models.

In other aspects, a method includes receiving from a plurality of exertion monitors located in or adjacent to an exercise venue corresponding exertion signals indicating one or more motion related metrics of a subject for each of a plurality of subjects exercising within the venue and identifying the subjects from the corresponding exertion signals. The method also includes: retrieving from a memory one or more dynamic physiological response models for each of the identified subjects; acquiring, for each of the identified subjects, data values from the received exertion signals during an exertion event within the venue; and individually predicting a physiological response for each of the identified subjects from the data values acquired from the received exertion signals during the exertion event and from one or more of the dynamic physiological response models.

For purposes of this document, reference in the specification to "an embodiment," "one embodiment," "some embodiments," or "another embodiment" may be used to describe different embodiments or the same embodiment.

For purposes of this document, a connection may be a direct connection or an indirect connection (e.g., via one or more other parts). In some cases, when an element is referred to as being connected or coupled to another element, the element may be directly connected to the other element or indirectly connected to the other element via intervening elements. When an element is referred to as being directly connected to another element, then there are no intervening elements between the element and the other element. Two devices are "in communication" if they are directly or indirectly connected so that they can communicate electronic signals between them.

For purposes of this document, the term "based on" may be read as "based at least in part on."

For purposes of this document, without additional context, use of numerical terms such as a "first" object, a "second" object, and a "third" object may not imply an ordering of objects, but may instead be used for identification purposes to identify different objects.

For purposes of this document, the term "set" of objects may refer to a "set" of one or more of the objects.

The foregoing detailed description has been presented for purposes of illustration and description. It is not intended to be exhaustive or to limit to the precise form disclosed. Many modifications and variations are possible in light of the above teaching. The described embodiments were chosen in order to best explain the principles of the proposed technology and its practical application, to thereby enable others skilled in the art to best utilize it in various embodiments and with various modifications as are suited to the particular use contemplated. It is intended that the scope be defined by the claims appended hereto.

I claim:

1. An exercise equipment, comprising:
   one or more exercise components;
   one or more physiological response monitors incorporated into the one or more exercise components, including a contact heart monitor configured to be gripped by hands of a subject, the physiological response monitors configured to provide heart rate data of the subject during an exertion event using the one or more exercise components;

one or more exertion monitors and configured to indicate one or more motion related metrics of a subject during the exertion event;

a memory configured to store one or more previously determined dynamic physiological response models for the subject, each of the dynamic physiological response models configured to provide a synthetically generated heart rate signal for the subject in real time from data values received from the exertion monitors in an absence of the one or more physiological signals, including the absence of the measured heart rate signal, indicating a heart rate value of the subject during a subsequent exertion event that corresponds to the subject's actual heart rate with a confidence level above a threshold value; and one or more processing circuits connected to the one or more physiological response monitors, to the one or more exertion monitors, and to the memory, one or more processing circuits configured to:
retrieve, from the memory, one or more of the dynamic physiological response models for the subject;
receive, from the one or more exertion monitors, the one or more motion related metrics of the subject during the exertion event;
in absence of the heart rate data of the subject from the physiological response monitors, providing the physiological response, including the synthetically generated heart rate signal, and the corresponding heart rate value for the subject, in real time, during the exertion event and from the retrieved one or more of the dynamic physiological response models for the subject;
subsequent to predicting the physiological response for the subject to the exertion event, and upon a renewed presence of heart rate data, receive, from the one or more physiological response monitors, the heart rate data of the subject during an exertion event using the one or more exercise components; and
during the exertion event, update the provided physiological response of the subject to the exertion event based on the received heart rate data of the subject to the exertion event.

2. The exercise equipment of claim 1, wherein the exercise equipment includes one or more of a treadmill, elliptical trainer, stair/step climber, a stationary/spin bike, and a rowing machine.

3. The exercise equipment of claim 1, wherein the one or more of the exertion monitors are incorporated into the one or more exercise components.

4. The exercise equipment of claim 3, wherein the exercise equipment includes a treadmill, and the exertion monitors include one or more of treadmill speed and treadmill incline.

5. The exercise equipment of claim 3, wherein the exercise equipment includes a spin bike, and the exertion monitors include one or more of cadence and power.

6. The exercise equipment of claim 1, wherein the exertion monitors provide the one or more motion related metrics in real time, and
the one or more processing circuits are configured to receive the one or more motion related metrics, predict the physiological response for the subject to the exertion event and update the prediction of the physiological response of the subject in real time.

7. The exercise equipment of claim 1, wherein the one or more processing circuits are further configured to:
receive, from a user wearable physiological response monitor, additional heart rate data of the subject during the exertion event using the one or more exercise components, and
further update the prediction of the physiological response of the subject to the exertion event based on the additional heart rate data of the subject to the exertion event.

8. A method, comprising:
calibrating one or more exertion monitors by, for each of the one or more exertion monitors:
receiving, from the exertion monitor, exertion signals indicating one or more motion related metrics of a subject during one or more exertion events in a corresponding exercise setting;
receiving, from one or more physiological response monitors, physiological signals indicating a heart rate of the subject during the one or more exertion events in the corresponding exercise setting; and
determining one or more dynamic physiological response models for the subject from a combination of data values from the received one or more exertion signals and data values from the received one or more physiological signals, including the measured heart rate signal, during the one or more exertion events in the corresponding exercise setting, the one or more dynamic physiological response models configured to synthetically generate a heart rate signal for the subject in real time from the data values received from the exertion monitors in an absence of the one or more physiological signals, including the absence of the measured heart rate signal, indicating a heart rate value of the subject during a subsequent exertion event that corresponds to the subject's actual heart rate with a confidence level above a threshold value; and
subsequent to calibrating the one or more exertion monitors, for each of the one or more calibrated exertion monitors:
monitoring exertion signals for the subject during one or more subsequent exertion events in the corresponding exercise setting;
determining motion related metrics for the subject during the one or more subsequent exertion events in the corresponding exercise setting from the monitored exertion signals; and
in absence of the heart rate data of the subject from the physiological response monitors, providing the synthetically generated heart rate signal, including the heart rate value, for the subject in real time during the one or more subsequent exertion events in the corresponding exercise setting from the determined motion related metrics and from one or more of the dynamic physiological response models for the subject.

9. The method of claim 8, wherein a first of the one or more exertion monitors is configured to monitor the subject during one or more exertion events on an exercise equipment in an indoor exercise setting.

10. The method of claim 9, where the first exertion monitor is incorporated into the exercise equipment.

11. The method of claim 8, wherein a first of the one or more exertion monitors is configured to monitor the subject during one or more exertion events in an outdoor exercise setting.

12. The method of claim 8, wherein the one or more of the exertion monitors include an exertion monitor incorporated into a user wearable device.

13. The method of claim 8, wherein the one or more of the exertion monitors include an inertial measurement unit.

14. The method of claim 8, wherein the one or more of the exertion monitors include one or more of an optical tracking monitor, an acoustical tracking monitor, or a radio frequency (RF) signal monitor.

15. A system, comprising:
one or more exertion monitors, each configured to:
provide exertion signals indicating one or more motion related metrics of a subject during one or more exertion events in a corresponding exercise setting; and
one or more processors configured, for each of the one or more exertion monitors to:
receive the exertion signals indicating the one or more motion related metrics of the subject during the one or more exertion events in the corresponding exercise setting;
receive, from one or more physiological response monitors, physiological signals indicating the heart rate of the subject during the one or more exertion events in the corresponding exercise setting;
determine, from the motion related metrics and the heart rate for the subject during the one or more exertion events in the corresponding exercise setting, calibration information providing one or more dynamic physiological response models for the subject from a combination of data values from the received one or more exertion signals and data values from the received one or more physiological signals, including the measured heart rate signal, during the one or more exertion events in the corresponding exercise setting, the one or more dynamic physiological response models configured to synthetically generate a heart rate signal for the subject in real time from the data values received from the exertion monitors in an absence of the one or more physiological signals, including the absence of the measured heart rate signal, indicating a heart rate value of the subject during a subsequent exertion event that corresponds to the subject's actual heart rate with a confidence level above a threshold value;
subsequent to determining the calibration information, monitor exertion signals for the subject during one or more subsequent exertion events in the corresponding exercise setting;
receive motion related metrics for the subject during the one or more subsequent exertion events in the corresponding exercise setting from the monitored exertion signals; and
in absence of the heart rate of the subject from the physiological response monitors, provide the synthetically generated heart rate signal, including the heart rate value, for the subject in real time during the one or more subsequent exertion events in the corresponding exercise setting from the determined motion related metrics and from one or more of the dynamic physiological response models for the subject.

16. The system of claim 15, wherein a first of the one or more exertion monitors is configured to monitor the subject during one or more exertion events on an exercise equipment in an indoor exercise setting.

17. The system of claim 16, where the first exertion monitor is incorporated into the exercise equipment.

18. The system of claim 15, wherein a first of the one or more exertion monitors is configured to monitor the subject during one or more exertion events in an outdoor exercise setting.

19. The system of claim 15, wherein the one or more of the exertion monitors include one or more of an optical tracking monitor, an acoustical tracking monitor, or a radio frequency (RF) signal monitor.

* * * * *